(12) United States Patent
Gera et al.

(10) Patent No.: US 12,044,856 B2
(45) Date of Patent: *Jul. 23, 2024

(54) CONFIGURABLE AUGMENTED REALITY EYEWEAR FOR IMAGE-GUIDED MEDICAL INTERVENTION

(71) Applicant: AUGMEDICS LTD., Yokneam Illit (IL)

(72) Inventors: Tomer Gera, Kfar Tavor (IL); Yaacov Hillel Rothschild, Kiryat Yearim (IL); Boris Nemirovsky, Ramat Ishay (IL)

(73) Assignee: AUGMEDICS LTD., Yokneam Illit (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/399,433

(22) Filed: Dec. 28, 2023

(65) Prior Publication Data

US 2024/0126087 A1    Apr. 18, 2024

Related U.S. Application Data

(63) Continuation of application No. 18/398,837, filed on Dec. 28, 2023, which is a continuation of application No. PCT/IB2023/059049, filed on Sep. 12, 2023.
(Continued)

(51) Int. Cl.
*G02B 27/01* (2006.01)
*A61B 90/00* (2016.01)
(Continued)

(52) U.S. Cl.
CPC .......... *G02B 27/0172* (2013.01); *A61B 90/37* (2016.02); *G02B 6/003* (2013.01);
(Continued)

(58) Field of Classification Search
CPC .... A61B 90/37; A61B 2090/372; G02B 7/14; G02B 7/022; G02B 27/0176;
(Continued)

(56) References Cited

U.S. PATENT DOCUMENTS 3,101,715 A    8/1963  Glassman
3,690,776 A    9/1972  Zaporoshan
(Continued)

FOREIGN PATENT DOCUMENTS

CA    3022448 A1    2/2018
CA    3034314 A1    2/2018
(Continued)

OTHER PUBLICATIONS

U.S. Appl. No. 16/159,740 U.S. Pat. No. 10,382,748, filed Oct. 15, 2018 Aug. 13, 2019, Combining Video-Based and Optic-Based Augmented Reality in a Near Eye Display.
(Continued)

*Primary Examiner* — Chineyere D Wills-Burns
*Assistant Examiner* — Cory A Almeida
(74) *Attorney, Agent, or Firm* — KNOBBE, MARTENS, OLSON & BEAR, LLP

(57) ABSTRACT

A head-mounted display device includes a frame; a head mounting assembly; and a see-through display assembly coupled to the frame; the see-through display assembly including a display assembly frame; a waveguide lens coupled to the display assembly frame; an anterior lens affixed to the waveguide lens or to the display assembly frame in front of the waveguide lens; a posterior lens frame detachably coupled to the display assembly frame using at least one of: a snap fit, a friction fit, or a clip; and a posterior lens affixed to the posterior lens frame.

20 Claims, 54 Drawing Sheets

Related U.S. Application Data

(60) Provisional application No. 63/405,901, filed on Sep. 13, 2022.

(51) Int. Cl.
*F21V 8/00* (2006.01)
*G02B 7/02* (2021.01)
*G02B 7/14* (2021.01)

(52) U.S. Cl.
CPC .............. *G02B 6/005* (2013.01); *G02B 7/022* (2013.01); *G02B 7/14* (2013.01); *A61B 2090/372* (2016.02); *G02B 2027/0159* (2013.01)

(58) Field of Classification Search
CPC ........ G02B 27/0172; G02B 2027/0152; G02B 6/003; G02B 6/005
See application file for complete search history.

(56) References Cited

U.S. PATENT DOCUMENTS

| | | |
|---|---|---|
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,147,365 A | 9/1992 | Whitlock et al. |
| 5,357,292 A | 10/1994 | Wiedner |
| 5,441,042 A | 8/1995 | Putman |
| 5,442,146 A | 8/1995 | Bell et al. |
| 5,510,832 A | 4/1996 | Garcia |
| D370,309 S | 5/1996 | Stucky |
| 5,636,255 A | 6/1997 | Ellis |
| 5,665,092 A | 9/1997 | Mangiardi et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Mlsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Stefan |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,657,075 B2 | 2/2010 | Viswanathan |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |
| D617,825 S | 6/2010 | Chang |

(56) References Cited

U.S. PATENT DOCUMENTS

| | | |
|---|---|---|
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | Jens |
| 8,644,907 B2 | 2/2014 | Hartmann et al. |
| 8,674,902 B2 | 3/2014 | Park et al. |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,965,583 B2 | 2/2015 | Ortmaier et al. |
| 8,969,829 B2 | 3/2015 | Wollenweber et al. |
| 8,989,349 B2 | 3/2015 | Thomson et al. |
| 8,992,580 B2 | 3/2015 | Bar et al. |
| 8,994,729 B2 | 3/2015 | Nakamura |

(56) References Cited

U.S. PATENT DOCUMENTS

| | | |
|---|---|---|
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |
| 9,085,643 B2 | 7/2015 | Svanborg et al. |
| 9,087,471 B2 | 7/2015 | Miao |
| 9,100,643 B2 | 8/2015 | McDowall et al. |
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Rodriguez Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,310,591 B2 | 4/2016 | Hua et al. |
| 9,320,474 B2 | 4/2016 | Demri et al. |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard et al. |
| 9,344,686 B2 | 5/2016 | Moharir |
| 9,349,066 B2 | 5/2016 | Koo et al. |
| 9,349,520 B2 | 5/2016 | Demetriou et al. |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Zhou |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,629,595 B2 | 4/2017 | Walker et al. |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque et al. |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,927,611 B2 | 3/2018 | Rudy et al. |
| 9,928,629 B2 | 3/2018 | Benishti et al. |
| 9,940,750 B2 | 4/2018 | Dillavou et al. |

(56) References Cited

U.S. PATENT DOCUMENTS

| | | |
|---|---|---|
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,046,165 B2 | 8/2018 | Frewin et al. |
| 10,055,838 B2 | 8/2018 | Elenbaas et al. |
| 10,066,816 B2 | 9/2018 | Chang |
| 10,067,359 B1 * | 9/2018 | Ushakov ............ G02B 27/0176 |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,212,517 B1 * | 2/2019 | Beltran ............ G02B 27/0101 |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca et al. |
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,398,514 B2 | 9/2019 | Ryan et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 * | 12/2019 | Edwards ................ F16M 13/04 |
| 10,504,231 B2 | 12/2019 | Fiala |
| 10,507,066 B2 | 12/2019 | Dimaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,087 B2 | 2/2020 | Gallop et al. |
| 10,577,630 B2 | 3/2020 | Zhang et al. |
| 10,586,400 B2 | 3/2020 | Douglas |
| 10,591,737 B2 | 3/2020 | Yildiz et al. |
| 10,592,748 B1 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |
| 10,634,921 B2 | 4/2020 | Blum et al. |
| 10,638,080 B2 | 4/2020 | Ovchinnikov et al. |

(56) References Cited

U.S. PATENT DOCUMENTS

| | | |
|---|---|---|
| 10,646,285 B2 | 5/2020 | Siemionow et al. |
| 10,650,513 B2 | 5/2020 | Penney et al. |
| 10,650,594 B2 | 5/2020 | Jones et al. |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik et al. |
| 10,672,145 B2 | 6/2020 | Albiol et al. |
| 10,682,112 B2 | 6/2020 | Pizaine et al. |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori et al. |
| 10,706,540 B2 | 7/2020 | Merlet |
| 10,709,398 B2 | 7/2020 | Schweizer |
| 10,713,801 B2 | 7/2020 | Jordan et al. |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare et al. |
| 10,748,319 B1 | 8/2020 | Tao et al. |
| 10,758,315 B2 | 9/2020 | Johnson et al. |
| 10,777,094 B1 | 9/2020 | Rao et al. |
| 10,777,315 B2 | 9/2020 | Zehavi et al. |
| 10,781,482 B2 | 9/2020 | Gubatayao et al. |
| 10,792,110 B2 | 10/2020 | Leung et al. |
| 10,799,145 B2 | 10/2020 | West et al. |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat et al. |
| 10,818,101 B2 | 10/2020 | Gallop et al. |
| 10,818,199 B2 | 10/2020 | Buras et al. |
| 10,825,563 B2 | 11/2020 | Gibby et al. |
| 10,831,943 B2 | 11/2020 | Santarone et al. |
| 10,835,296 B2 | 11/2020 | Elimelech et al. |
| 10,838,206 B2 | 11/2020 | Fortin-Deschnes et al. |
| 10,839,629 B2 | 11/2020 | Jones et al. |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker et al. |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino et al. |
| 10,869,517 B1 | 12/2020 | Halpern |
| 10,869,727 B2 | 12/2020 | Yanof et al. |
| 10,872,472 B2 | 12/2020 | Watola et al. |
| 10,877,262 B1 | 12/2020 | Luxembourg |
| 10,877,296 B2 | 12/2020 | Lindsey et al. |
| 10,878,639 B2 | 12/2020 | Douglas et al. |
| 10,893,260 B2 | 1/2021 | Trail et al. |
| 10,895,742 B2 | 1/2021 | Schneider et al. |
| 10,895,743 B2 | 1/2021 | Dausmann |
| 10,895,906 B2 | 1/2021 | West et al. |
| 10,898,151 B2 | 1/2021 | Harding et al. |
| 10,921,595 B2 | 2/2021 | Rakshit et al. |
| 10,921,613 B2 | 2/2021 | Gupta et al. |
| 10,928,321 B2 | 2/2021 | Rawle |
| 10,928,638 B2 | 2/2021 | Ninan et al. |
| 10,929,670 B1 | 2/2021 | Troy et al. |
| 10,935,815 B1 | 3/2021 | Castaeda |
| 10,935,816 B2 | 3/2021 | Ban et al. |
| 10,936,537 B2 | 3/2021 | Huston |
| 10,939,973 B2 | 3/2021 | Dimaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,993,754 B2 | 5/2021 | Kuntz et al. |
| 11,000,335 B2 | 5/2021 | Dorman |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,019,988 B2 | 6/2021 | Fiebel et al. |
| 11,027,027 B2 | 6/2021 | Manning et al. |
| 11,029,147 B2 | 6/2021 | Abovitz et al. |
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | Leboeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,202,682 B2 | 12/2021 | Staunton et al. |
| 11,207,150 B2 | 12/2021 | Healy et al. |
| 11,217,028 B2 | 1/2022 | Jones et al. |
| 11,224,483 B2 | 1/2022 | Steinberg et al. |
| 11,224,763 B2 | 1/2022 | Takahashi et al. |
| 11,227,417 B2 | 1/2022 | Berlinger et al. |
| 11,231,787 B2 | 1/2022 | Isaacs et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao et al. |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |

(56) References Cited

U.S. PATENT DOCUMENTS

| | | |
|---|---|---|
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,423,554 B2 | 8/2022 | Borsdorf et al. |
| 11,432,828 B1 | 9/2022 | Lang |
| 11,432,931 B2 | 9/2022 | Lang |
| 11,452,568 B2 | 9/2022 | Lang |
| 11,460,915 B2 | 10/2022 | Frielinghaus et al. |
| 11,461,983 B2 | 10/2022 | Jones et al. |
| 11,464,581 B2 | 10/2022 | Calloway |
| 11,478,214 B2 | 10/2022 | Siewerdsen et al. |
| 11,483,532 B2 | 10/2022 | Quiles Casas |
| 11,490,986 B2 | 11/2022 | Ben-Yishai |
| 11,527,002 B2 | 12/2022 | Govari |
| 11,528,393 B2 | 12/2022 | Garofolo et al. |
| 11,627,924 B2 | 4/2023 | Alexandroni et al. |
| 11,648,016 B2 | 5/2023 | Hathaway et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,712,582 B2 | 8/2023 | Miyazaki et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,826,111 B2 | 11/2023 | Mahfouz |
| 11,839,501 B2 | 12/2023 | Takahashi et al. |
| 11,885,752 B2 | 1/2024 | St-Aubin et al. |
| 11,896,445 B2 | 2/2024 | Gera et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0238732 A1 | 12/2004 | State et al. |
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2006/0072124 A1 | 4/2006 | Smetak et al. |
| 2006/0134198 A1 | 6/2006 | Tawa et al. |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0183041 A1 | 8/2007 | McCloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0018437 A1 | 1/2009 | Cooke |
| 2009/0024127 A1 | 1/2009 | Lechner et al. |
| 2009/0036902 A1 | 2/2009 | Dimaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1* | 9/2012 | Healy ............... G02C 5/10 359/464 |
| 2012/0238609 A1 | 9/2012 | Srivastava et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |

(56) References Cited

U.S. PATENT DOCUMENTS

| | | |
|---|---|---|
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1* | 11/2015 | Lim .................... G06F 3/04812 345/158 |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1* | 6/2016 | Casas ................. G02B 27/0172 348/47 |
| 2016/0223822 A1 | 8/2016 | Harrison et al. |
| 2016/0228033 A1 | 8/2016 | Rossner |
| 2016/0246059 A1* | 8/2016 | Halpin ............... G02B 27/0176 |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1* | 2/2017 | Greenhalgh ....... G02B 27/0081 |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0164919 A1 | 6/2017 | Lavallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0117150 A1 | 5/2018 | O'Dwyer et al. |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1* | 2/2019 | Abele .................... G09G 3/001 |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192230 A1 | 6/2019 | Siemionow et al. |
| 2019/0200894 A1 | 7/2019 | Jung et al. |

(56) References Cited

U.S. PATENT DOCUMENTS

| | | |
|---|---|---|
| 2019/0201106 A1 | 7/2019 | Siemionow et al. |
| 2019/0216537 A1 | 7/2019 | Eltorai et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1* | 12/2019 | Wen .................. G06F 1/163 |
| 2019/0369717 A1 | 12/2019 | Frielinghaus et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0286222 A1 | 9/2020 | Essenreiter et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0375666 A1 | 12/2020 | Murphy |
| 2020/0377493 A1 | 12/2020 | Heiser et al. |
| 2020/0377956 A1 | 12/2020 | Vogelstein et al. |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1* | 7/2021 | Bristol ............... G02B 27/0176 |
| 2021/0223577 A1 | 7/2021 | Zhang et al. |
| 2021/0227791 A1 | 7/2021 | De et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295512 A1 | 9/2021 | Knoplioch et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1* | 11/2021 | Cakmakci ............... G02C 7/086 |
| 2021/0341740 A1* | 11/2021 | Cakmakci .......... G02B 27/0025 |
| 2021/0346115 A1 | 11/2021 | Dulin et al. |
| 2021/0349677 A1 | 11/2021 | Baldev et al. |
| 2021/0364802 A1* | 11/2021 | Uchiyama .............. G02C 9/04 |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0386482 A1 | 12/2021 | Gera et al. |

(56) References Cited

U.S. PATENT DOCUMENTS

| | | |
|---|---|---|
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0269077 A1* | 8/2022 | Adema ............. G02B 27/0172 |
| 2022/0270263 A1 | 8/2022 | Junio |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0304768 A1 | 9/2022 | Elimelech et al. |
| 2022/0351385 A1 | 11/2022 | Finley et al. |
| 2022/0358759 A1 | 11/2022 | Cork et al. |
| 2022/0392085 A1 | 12/2022 | Finley et al. |
| 2022/0405935 A1 | 12/2022 | Flossmann et al. |
| 2023/0009793 A1 | 1/2023 | Gera et al. |
| 2023/0027801 A1 | 1/2023 | Qian et al. |
| 2023/0034189 A1 | 2/2023 | Gera et al. |
| 2023/0073041 A1 | 3/2023 | Samadani et al. |
| 2023/0149083 A1 | 5/2023 | Lin et al. |
| 2023/0290037 A1 | 9/2023 | Tasse et al. |
| 2023/0295302 A1 | 9/2023 | Bhagavatheeswaran et al. |
| 2023/0316550 A1 | 10/2023 | Hiasa |
| 2023/0329799 A1 | 10/2023 | Gera et al. |
| 2023/0329801 A1 | 10/2023 | Elimelech et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386153 A1 | 11/2023 | Rybnikov et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041558 A1 | 2/2024 | Siewerdsen et al. |

FOREIGN PATENT DOCUMENTS

| | | |
|---|---|---|
| CN | 101379412 A | 3/2009 |
| CN | 103106348 A | 5/2013 |
| CN | 111915696 A | 11/2020 |
| CN | 112489047 A | 3/2021 |
| DE | 202004011567 U1 | 11/2004 |
| DE | 102004011567 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2134847 A2 | 12/2009 |
| EP | 2557998 A1 | 2/2013 |
| EP | 2823463 A1 | 1/2015 |
| EP | 2868277 A1 | 5/2015 |
| EP | 2891966 A1 | 7/2015 |
| EP | 2963616 A2 | 1/2016 |
| EP | 3028258 A1 | 6/2016 |
| EP | 3034607 A1 | 6/2016 |
| EP | 3037038 A1 | 6/2016 |
| EP | 3069318 A1 | 9/2016 |
| EP | 3076660 A1 | 10/2016 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3256213 A1 | 12/2017 |
| EP | 3306567 A1 | 4/2018 |
| EP | 2030193 B1 | 7/2018 |
| EP | 2225723 B1 | 2/2019 |
| EP | 2892558 B1 | 4/2019 |
| EP | 2635299 B1 | 7/2019 |
| EP | 3505050 A1 | 7/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 3711700 A1 | 9/2020 |
| EP | 2625845 B1 | 3/2021 |
| EP | 3789965 A1 | 3/2021 |
| EP | 3858280 A1 | 8/2021 |
| EP | 3913423 A1 | 11/2021 |
| EP | 3952331 A1 | 2/2022 |
| EP | 3960235 A1 | 3/2022 |
| EP | 4173590 A1 | 5/2023 |
| EP | 4252695 A1 | 10/2023 |
| EP | 4270313 A1 | 11/2023 |
| EP | 4287120 A1 | 12/2023 |
| GB | 2507314 A | 4/2014 |
| KR | 10-2014-0120155 A | 10/2014 |
| WO | 03/34705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019/083431 A1 | 5/2019 |
| WO | 2019/135209 A1 | 7/2019 |
| WO | 2019/161477 A1 | 8/2019 |

(56) References Cited

FOREIGN PATENT DOCUMENTS

| | | |
|---|---|---|
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |
| WO | 2022/009233 A1 | 1/2022 |
| WO | 2022/053923 A1 | 3/2022 |
| WO | 2022/079565 A1 | 4/2022 |
| WO | 2023/281395 A1 | 1/2023 |
| WO | 2023/007418 A1 | 2/2023 |
| WO | 2023/011924 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |
| WO | 2023/047355 A1 | 3/2023 |
| WO | 2023/072887 A1 | 5/2023 |
| WO | 2023/088986 A1 | 5/2023 |
| WO | 2023/163933 A1 | 8/2023 |
| WO | 2023/186996 A1 | 10/2023 |
| WO | 2023/205212 A1 | 10/2023 |
| WO | 2023/209014 A1 | 11/2023 |
| WO | 2023/232492 A1 | 12/2023 |
| WO | 2023/240912 A1 | 12/2023 |
| WO | 2024/013642 A2 | 1/2024 |
| WO | 2024/018368 A2 | 1/2024 |

OTHER PUBLICATIONS

U.S. Appl. No. 16/419,023 U.S. Pat. No. 11,750,794, filed May 22, 2019 Sep. 5, 2023, Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643, filed Aug. 4, 2023, Head-Mounted Augmented Reality Near Eye Display Device.
U.S. Appl. No. 18/365,650, filed Aug. 4, 2023, Systems for Facilitating Augmented Reality-Assisted Medical Procedures.
U.S. Appl. No. 15/127,423 U.S. Pat. No. 9,928,629, filed Sep. 20, 2016 Mar. 27, 2018, Combining Video-Based and Optic-Based Augmented Reality in a Near Eye Display.
U.S. Appl. No. 16/120,480 U.S. Pat. No. 10,835,296, filed Sep. 4, 2018 Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590, filed Aug. 4, 2023, Registration of a Fiducial Marker for an Augmented Reality System.
U.S. Appl. No. 18/365,571, filed Aug. 4, 2023, Registration Marker for an Augmented Reality System.
U.S. Appl. No. 17/045,766, filed Oct. 7, 2020, Registration of a Fiducial Marker for an Augmented Reality System.
U.S. Appl. No. 16/199,281 U.S. Pat. No. 10,939,977, filed Nov. 26, 2018 Mar. 9, 2021, Positioning Marker.
U.S. Appl. No. 16/524,258, filed Jul. 29, 2019, Fiducial Marker.
U.S. Appl. No. 17/585,629, filed Jan. 27, 2022, Fiducial Marker.
U.S. Appl. No. 16/724,297 U.S. Pat. No. 11,382,712, filed Dec. 22, 2019 Jul. 12, 2022, Mirroring in Image Guided Surgery.
U.S. Appl. No. 17/827,710 U.S. Pat. No. 11,801,115, filed May 29, 2022 Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 16/200,144 U.S. Pat. No. 11,766,296, filed Nov. 26, 2018 Sep. 26, 2023, Tracking System for Image-Guided Surgery.
U.S. Appl. No. 18/470,809, filed Sep. 20, 2023, Tracking Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-Guided Surgery.
U.S. Appl. No. 16/901,026 U.S. Pat. No. 11,389,252, filed Jun. 15, 2020 Jul. 19, 2022, Rotating Marker for Image Guided Surgery.
U.S. Appl. No. 18/008,980, filed Dec. 8, 2022, Rotating Marker.
U.S. Appl. No. 17/368,859 U.S. Pat. No. 11,896,445, filed Jul. 7, 2021 Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/398,837, filed Dec. 28, 2023, Adjustable Augmented Reality Eyewear for Image-Guided Medical Intervention.
U.S. Appl. No. 35/508,942 U.S. Pat. No. D. 930,162, filed Feb. 13, 2020 Sep. 7, 2021, Medical Headset.
U.S. Appl. No. 15/896,102 U.S. Pat. No. 10,134,166, filed Feb. 14, 2018 Nov. 20, 2018, Combining Video-Based and Optic-Based Augmented Reality in a Near Eye Display.
U.S. Appl. No. 18/693,338, filed Mar. 19, 2024, Surgical Planning and Display.
International Search Report and Written Opinion received for PCT Patent Application No. PCT/IB2023/059049, mailed on Feb. 8, 2024, 24 pages.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Vuzix Blades, Prescription Lens Installation Guide, copyright 2020.
Frames Direct, InSpatialRx Prescription Insert, Prescription Insert for Magic Leap 1, accessed Mar. 8, 2024 at https://www.framesdirect.com/inspatialrx-prescription-insert.html.
Everysight, Installing your RX Adaptor, accessed Mar. 13, 2024 at https://support.everysight.com/hc/en-us/articles/115000984571-Installing-your-RX-Adaptor.

(56) References Cited

OTHER PUBLICATIONS

Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Everysight, Raptor User Manual, copyright 2017, in 46 pages.

* cited by examiner

CONFIGURABLE AUGMENTED REALITY EYEWEAR FOR IMAGE-GUIDED MEDICAL INTERVENTION

CROSS-REFERENCE TO RELATED APPLICATIONS

This application is a continuation of U.S. patent application Ser. No. 18/398,837, filed Dec. 28, 2023, titled "ADJUSTABLE AUGMENTED REALITY EYEWEAR FOR IMAGE-GUIDED MEDICAL INTERVENTION," which is a continuation of International PCT Application PCT/IB2023/059049, filed Sep. 12, 2023, titled "AUGMENTED REALITY EYEWEAR FOR IMAGE-GUIDED MEDICAL INTERVENTION," which claims priority to U.S. Provisional Application No. 63/405,901, filed Sep. 13, 2022, titled "AUGMENTED REALITY EYEWEAR FOR IMAGE-GUIDED MEDICAL INTERVENTION." The disclosure of each of the foregoing applications is incorporated herein by reference in its entirety for all purposes.

FIELD

This disclosure relates generally to an augmented reality systems, devices and methods, including a head mounted display (HMD) device of an augmented-reality (AR)-based image-guided system to facilitate surgery or other medical intervention (e.g., therapeutic and/or diagnostic procedures), as well as other uses.

BACKGROUND

Near-eye displays may be used in various types of AR applications. For example, Applicant has previously demonstrated that head-mounted devices having AR capabilities may be used for performing image-guided surgery (see, for example, Applicant's U.S. Pat. Nos. 11,382,712, 11,389,252, 10,939,977, and 9,928,629, Applicant's US Publication No. 2020/0163723, and Applicant's PCT Publication Nos. WO 2023/021448 and WO 2023/021450, which describe methods and systems for applying augmented reality and near-eye display techniques to an image-guided surgical system). The disclosures of these patents and published applications are incorporated herein by reference.

SUMMARY

Several embodiments of the disclosure that are described hereinbelow provide improved methods and systems for applying augmented reality (AR) techniques, peripheral devices and operational methods thereof to a head-mounted display (HMD) of, for example, an image-guided medical (e.g., surgical) system. In the context of the present disclosure and in the claims, the term head-mounted display or HMD shall be given its ordinary meaning and shall also refer to any suitable display apparatus configured to display information (e.g., images) over a scene (e.g., portion of a body of a patient for therapeutic or diagnostic intervention or assessment), such as an organ, skin, bones or joints of a patient, using AR techniques and/or other suitable displaying techniques. For example, the term HMD may refer to a helmet, AR glasses, goggles, spectacles, monocle, eyewear, headset, visor, head-up display, and any other suitable type of displaying device mounted on or worn by any portion of a user or wearer's head, including but not limited to the face, crown, forehead, nose and ears. In some embodiments, the head-mounted displays are not used or used together with stand-alone displays, such as monitors, portable devices, tablets, etc. The display may be a hands-free display such that the operator does not need to hold the display.

In accordance with several embodiments, head-mounted display devices described herein provide reduced stress or fatigue on a wearer, and/or provide additional comfort features. The head-mounted display devices may provide improved ergonomics, comfort, and/or the ability to enable a wearer, such as a surgeon, to wear the device for relatively long periods of time (such as for two, four, six, hours or more in one embodiment), without unnecessary fatigue and/or other negative consequences. For example, the head-mounted display device can be designed and adapted to distribute weight around the wearer's head, including to the wearer's forehead and the back of the wearer's head, to reduce at least some of the weight applied to the wearer's nose or other undesired location. Such a configuration can also reduce pressure on the wearer's temples which can be another relatively weight-sensitive area, in addition to the nose. Stated another way, such a head-mounted display can more widely distribute pressure over larger and/or less sensitive areas, such as the forehead and the back of the head. Although medical applications are well-suited for several embodiments, non-medical applications also benefit from many embodiments described herein. For example, non-medical applications may involve consumer or commercial applications such as athletics and fitness, gaming, driving, product design, navigation, manufacturing, logistics, shopping and commerce, educational training, remote collaboration, etc.

The head-mounted display device may be substituted with an alternative hands-free device that is not worn by the operator, such as a portal, monitor or tablet. The display may be a head-up display or heads-up display.

In accordance with several implementations, a head-mounted display device includes: a frame extending from a first end to a second end, the first end configured to be positioned adjacent a first temple of a wearer (e.g., a surgeon or other user), and the second end configured to be positioned adjacent a second temple of the wearer. The device further includes an adjustable strap assembly including: a first side strap having a first end coupled to the first end of the frame; a second side strap having a first end coupled to the second end of the frame; and an adjustment mechanism (e.g., a knob, a rack and pinion, a mechanism that uses friction, a sliding mechanism, a ratchet mechanism, a snap or lock mechanism, etc.) configured to adjust a position of a second end of the first side strap with respect to a second end of the second side strap, in order to adjust a circumferential size defined by the first side strap, the second side strap, and the frame. The device also includes a see-through display assembly (including, e.g., a near-eye display, an augmented-reality display, a stereoscopic display, glasses, a visor, a head-up display, etc.) coupled (e.g., rotatably, pivotably, movably, or slidably coupled) to the frame such that a tilt angle (e.g., pantoscopic tilt angle) can be adjusted. The device further includes a first temple housing coupled (e.g., rotatably or pivotably coupled) to the first end of the frame and slidably coupled to the first side strap of the adjustable strap assembly and a second temple housing coupled (e.g., rotatably or pivotably coupled) to the second end of the frame and slidably coupled to the second side strap of the adjustable strap assembly.

In some implementations, the see-through display assembly is coupled (e.g., rotatably, pivotably, movably, or slidably coupled) to the frame with a pantoscopic tilting assembly that includes an arc-shaped slot that rotatably, pivotably, movably, or slidably couples a portion of the see-through display assembly to a portion of the frame.

In some implementations, the pantoscopic tilting assembly further includes a detent mechanism including a spring-loaded pin or ball and a plurality of detents (e.g., two, three, four, five, or more than five detents), the detent mechanism configured to selectively retain the see-through display assembly in any of a plurality of predefined positions with respect to the frame.

In some implementations, the detent mechanism further includes a guide member slidably engaged with the arc-shaped slot, the guide member configured to apply a force to the spring-loaded pin or ball to move the spring-loaded pin or ball from one of the plurality of detents to another of the plurality of detents.

In some implementations, the see-through display assembly includes a detachable lens assembly (e.g., clip-on lens assembly, snap-on lens assembly, a friction-fit lens assembly, a magnetic attachment assembly, etc.) that can be detached and replaced with a second detachable lens assembly for changing a prescription of lenses of the see-through display assembly (e.g., the detachable lens assemblies may be customized for a particular wearer such that they are swappable and the same device can be easily interchangeably used by multiple different wearers). In some implementations, the detachable lens assembly may be provided by the manufacturer and/or provider of the head-mounted display device with the head-mounted display device such that they are not required to be obtained separately by a user from an optometrist or third-party provider. In some implementations, the detachable lens assembly can be coupled and detached to the head-mounted display device without requiring the use of any tools (e.g., "tools-free"). In some implementations, the detachable lens assembly comprises or functions as an adapter. In some implementations, the detachable lens assembly is a non-magnetically coupled to the head-mounted display device.

In some implementations, the see-through display assembly includes a display assembly frame; a waveguide lens coupled to the display assembly frame; an anterior lens affixed to the waveguide lens or to the display assembly frame in front of the waveguide lens; a posterior lens frame detachably coupled to the display assembly frame using at least one of: a snap fit, a friction fit, or a clip; and a posterior lens affixed to the posterior lens frame.

In some implementations, the head-mounted display device further includes a flashlight assembly (e.g., headlamp assembly, headlight assembly, etc.) that may be detachably coupled to the frame. In some implementations, the flashlight may be permanently coupled to the frame.

In some implementations, the head-mounted display device further includes: a first follower (e.g., protrusion, slidable member, etc.) that slidably couples the first temple housing to the first side strap; and a second follower (e.g., protrusion, slidable member, etc.) that slidably couples the second temple housing to the second side strap.

In some implementations, the frame further includes a nose pad (e.g., nose support member, etc.) configured to engage a nose of the wearer. The frame may optionally not include a nose pad or may be configured not to engage a nose of the wearer.

In some implementations, the head-mounted display device further includes: a forehead support including: a first end coupled (e.g., rotatably or pivotably coupled) to the first side strap; a second end coupled (e.g., rotatably or pivotably coupled) to the second side strap; and a central support coupled to the frame.

In some implementations, the first side strap includes a connector that couples (e.g., rotatably or pivotably couples) a front portion of the first side strap to a rear portion of the first side strap, and that couples (e.g., rotatably or pivotably couples) the first end of the forehead support to the first side strap. The second side strap includes a connector that couples (e.g., rotatably or pivotably couples) a front portion of the second side strap to a rear portion of the second side strap, and that couples (e.g., rotatably or pivotably couples) the second end of the forehead support to the second side strap.

In some implementations, the head-mounted display device further includes: a first follower (e.g., protrusion, slidable member, etc.) that is slidably coupled to the first temple housing and that is coupled to the first side strap at a position between the connector of the first side strap and the first end of the first side strap; and a second follower (e.g., protrusion, slidable member, etc.) that is slidably coupled to the second temple housing and that is coupled to the second side strap at a position between the connector of the second side strap and the first end of the second side strap.

In some implementations, the head-mounted display device further optionally includes a top strap removably coupled at a first end to the forehead support and at a second end to the adjustment mechanism of the adjustable strap assembly.

In some implementations, each of the first side strap and the second strap includes a rack, and wherein the adjustment mechanism of the adjustable strap assembly includes: a pinion engaged with the rack of the first side strap and with the rack of the second side strap; and a knob configured to cause rotation of the pinion in order to adjust the circumferential size defined by the first side strap, the second side strap, and the frame (e.g., to customize the fit to a circumferential head size of a particular wearer).

In some implementations, the adjustment mechanism of the adjustable strap assembly further includes a tension mechanism (e.g., stop mechanism, one or more gears engaged with a tension member, etc.) that resists rotation of the knob until a threshold force is overcome.

In some implementations, the adjustment mechanism of the adjustable strap assembly further includes a pad configured to engage a back of a head of the wearer.

In some implementations, the see-through display assembly is configured to display to the wearer an augmented reality (AR) image including a virtual reality (VR) image presented over a portion of a body of a patient, and the head-mounted display device further includes or consists essentially of one or more processors configured to, e.g., upon execution of program instructions stored on a non-transitory computer readable medium, receive one or more anatomical images of the patient and signals indicative of at least a position of the see-through display assembly relative to the scene, and to render the AR image to the see-through display assembly. The see-through display assembly may be configured to allow the wearer to see AR images from both a standing and a sitting position without inconvenience or manual adjustment.

In some implementations, at least one of the one or more processors is positioned within the first temple housing or the second temple housing. In some implementations, at least one of the one or more processors may be located in other locations on the head-mounted display device or separate from the head-mounted display device and in wireless communication with the head-mounted display device.

In accordance with several implementations, a head-mounted display device includes a frame extending from a first end to a second end, the first end configured to be positioned adjacent a first temple of a wearer (e.g., a surgeon or other user), and the second end configured to be positioned adjacent a second temple of the wearer. The frame further includes a nose pad (e.g., nose support member, etc.) configured to engage a nose of the wearer; an adjustable strap assembly including a first side strap having a first end coupled to the first end of the frame; a second side strap having a first end coupled to the second end of the frame; and an adjustment mechanism (e.g., a knob, a rack and pinion, a mechanism that uses friction, etc.) configured to adjust a position of a second end of the first side strap with respect to a second end of the second side strap, in order to adjust a circumferential size defined by the first side strap, the second side strap, and the frame. The head-mounted display device further includes a forehead support including a first end coupled (e.g., rotatably or pivotably coupled) to the first side strap; a second end coupled (e.g., rotatably or pivotably coupled) to the second side strap; and a central support coupled to the frame. The head-mounted display device further includes a see-through display assembly (e.g., augmented-reality display, near-eye display, stereoscopic display, glasses, visor, headset, goggles, head-up display, etc.) coupled (e.g., rotatably, pivotably, movably, or slidably coupled) to the frame such that a tilt angle (e.g., pantoscopic tilt angle) can be adjusted. The see-through display assembly includes a detachable lens assembly (e.g., clip-on lens assembly, snap-on lens assembly, a friction-fit lens assembly, etc.) that can be detached and replaced with a second detachable lens assembly for changing a prescription of lenses of the see-through display assembly. The head-mounted display device also includes a first temple housing pivotably coupled to the first end of the frame and slidably coupled to the first side strap of the adjustable strap assembly and a second temple housing pivotably coupled to the second end of the frame and slidably coupled to the second side strap of the adjustable strap assembly. The head-mounted display device further includes a flashlight assembly (e.g., headlamp assembly, headlight assembly, etc.) detachably coupled to the frame.

In some implementations, the first side strap includes a connector that pivotably couples a front portion of the first side strap to a rear portion of the first side strap, and that pivotably couples the first end of the forehead support to the first side strap. The second side strap includes a connector that pivotably couples a front portion of the second side strap to a rear portion of the second side strap, and that pivotably couples the second end of the forehead support to the second side strap.

In some implementations, the head-mounted display device further includes a first follower (e.g., protrusion, slidable member, etc.) that is slidably coupled to the first temple housing and that is coupled to the first side strap at a position between the connector of the first side strap and the first end of the first side strap, and a second follower (e.g., protrusion, slidable member, etc.) that is slidably coupled to the second temple housing and that is coupled to the second side strap at a position between the connector of the second side strap and the first end of the second side strap.

In some implementations, each of the first side strap and the second strap includes a rack. The adjustment mechanism of the adjustable strap assembly may include a pinion engaged with the rack of the first side strap and with the rack of the second side strap and a knob configured to cause rotation of the pinion in order to adjust the circumferential size defined by the first side strap, the second side strap, and the frame.

In some implementations, the adjustment mechanism of the adjustable strap assembly further includes a tension mechanism (e.g., stop mechanism, one or more gears engaged with a tension member, etc.) that resists rotation of the knob until a threshold force is overcome.

In some implementations, the adjustment mechanism of the adjustable strap assembly further includes a pad configured to engage a back of a head of the wearer.

In some implementations, the head-mounted display device further includes a top strap removably coupled at a first end to the forehead support and at a second end to the adjustment mechanism of the adjustable strap assembly.

In some implementations, the see-through display assembly is configured to display to the wearer an augmented reality (AR) image including a virtual reality (VR) image presented over a scene on a body of a patient, and the head-mounted display device further includes one or more processors configured to receive one or more anatomical images of the patient and signals indicative of at least a position of the see-through display assembly relative to the scene, and to render the AR image to the see-through display assembly.

In some implementations, at least one of the one or more processors is positioned within the first temple housing or the second temple housing. In some implementations, at least one of the one or more processors may be located in other locations on the head-mounted display device or separate from the head-mounted display device and in wireless communication with the head-mounted display device.

In some implementations, each of the first temple housing and the second temple housing includes a plurality of heat-dissipation fins (e.g., protrusions, heatsinks, etc.).

In some implementations, the see-through display assembly is rotatably, pivotably, movably, or slidably coupled coupled to the frame with a pantoscopic tilting assembly that includes an arc-shaped slot that rotatably, pivotably, movably, or slidably couples a portion of the see-through display assembly to a portion of the frame and a detent mechanism including a spring-loaded pin or ball and a plurality of detents. The detent mechanism may be configured to selectively retain the see-through display assembly in any of a plurality of predefined positions with respect to the frame.

In some implementations, the detent mechanism further includes a guide member slidably engaged with the arc-shaped slot, the guide member configured to apply a force to the spring-loaded pin or ball to move the spring-loaded pin or ball from one of the plurality of detents to another of the plurality of detents.

In some implementations, the frame includes a flashlight mounting socket including a first rod (e.g., post, protrusion, shaft, etc.) that defines a pivot or rotation axis and a second rod (e.g., post, protrusion, shaft, etc.) positioned parallel to the first rod. The flashlight assembly may include a first recess (e.g., opening, socket, depression, etc.) shaped to engage and pivot about the first rod of the flashlight mounting socket; a second recess (e.g., opening, socket, depression, etc.) shaped to engage the second rod of the flashlight mounting socket, the second recess being oriented such that the first recess cannot disengage the first rod when the second recess is engaged with the second rod; and a movable latch (e.g., hook, coupler, etc.) configured to selectively retain the second recess in engagement with the second rod.

In some implementations, the head-mounted display device further includes a spring or other biasing mechanism that biases the movable latch toward a position that retains the second recess in engagement with the second rod.

In some implementations, the flashlight assembly includes a flashlight (e.g., headlight, headlamp, etc.); a mounting base that includes the first recess, the second recess, and the movable latch; and one or more arms that pivotably or otherwise rotatably couple the flashlight to the mounting base.

In some implementations, the see-through display assembly includes a display assembly frame; a waveguide lens coupled to the display assembly frame; an anterior lens affixed to the waveguide lens or to the display assembly frame in front of the waveguide lens; a posterior lens frame detachably coupled to the display assembly frame using at least one of: a snap fit, a friction fit, a magnetic attachment, a hook-and-fastener attachment, or a clip; and a posterior lens affixed to the posterior lens frame.

In accordance with several implementations, a head-mounted display device includes a frame extending from a first end to a second end, the first end configured to be positioned adjacent a first temple of a wearer (e.g., a surgeon or other user), and the second end configured to be positioned adjacent a second temple of the wearer; a head mounting assembly configured to retain the frame in a position on a head of the wearer; a see-through display; and a tilting assembly (e.g., pantoscopic tilting assembly) that rotatably, pivotably, movably, or slidably couples the see-through display to the frame such that a tilt angle (e.g., pantoscopic tilt angle) can be adjusted. The tilting assembly (e.g., pantoscopic tilting assembly) includes an arc-shaped slot that rotatably, pivotably, movably, or slidably couples a portion of the see-through display assembly to a portion of the frame. The tilting assembly also includes a detent mechanism including a spring-loaded pin or ball and a plurality of detents, the detent mechanism configured to selectively retain the see-through display assembly in any of a plurality of predefined positions with respect to the frame.

In some implementations, the detent mechanism further includes a guide member slidably engaged with the arc-shaped slot, the guide member configured to apply a force to the spring-loaded pin or ball to move the spring-loaded pin or ball from one of the plurality of detents to another of the plurality of detents.

In some implementations, the arc-shaped slot defines a virtual hinge that includes an axis of rotation that is configured to be aligned with a center of an eyeball of the wearer. In some implementations, the virtual hinge as opposed to a physical hinge advantageously allows for peripheral vision of the wearer not to be obstructed or distorted.

In some implementations, the head mounting assembly includes an adjustable strap assembly including a first side strap having a first end coupled to the first end of the frame; a second side strap having a first end coupled to the second end of the frame; and an adjustment mechanism (e.g., a knob, a rack and pinion, a mechanism that uses friction, etc.) configured to adjust a position of a second end of the first side strap with respect to a second end of the second side strap, in order to adjust a circumferential size defined by the first side strap, the second side strap, and the frame.

In some implementations, the head-mounted display device further includes a forehead support including a first end pivotably coupled to the first side strap; a second end pivotably coupled to the second side strap; and a central support coupled to the frame.

In some implementations, the head-mounted display device further includes a first temple housing pivotably coupled to the first end of the frame and slidably coupled to the head mounting assembly; a second temple housing pivotably coupled to the second end of the frame and slidably coupled to the head mounting assembly; and one or more processors configured to (e.g., upon execution of program instructions stored on a non-transitory computer readable medium) render images for display by the see-through display. In some implementations, at least one of the one or more processors is positioned within the first temple housing or the second temple housing, although they may be in other locations as well.

In some implementations, the head mounting assembly includes a first temple arm coupled to the frame and configured to be placed over a first ear of the wearer; and a second temple arm coupled to the frame and configured to be placed over a second ear of the wearer.

In some implementations, the frame further includes a nose pad (e.g., nose support member, etc.) configured to engage a nose of the wearer.

In accordance with several implementations, a head-mounted display device includes a frame extending from a first end to a second end, the first end configured to be positioned adjacent a first temple of a wearer (e.g., a surgeon or other user), and the second end configured to be positioned adjacent a second temple of the wearer. The head-mounted display device also includes an adjustable strap assembly including a first side strap having a first end coupled to the first end of the frame; a second side strap having a first end coupled to the second end of the frame; and an adjustment mechanism (e.g., a knob, a rack and pinion, a mechanism that uses friction, etc.) configured to adjust a position of a second end of the first side strap with respect to a second end of the second side strap, in order to adjust a circumferential size defined by the first side strap, the second side strap, and the frame. The head-mounted display device further includes a first temple housing pivotably coupled to the first end of the frame and slidably coupled to the first side strap of the adjustable strap assembly and a second temple housing pivotably coupled to the second end of the frame and slidably coupled to the second side strap of the adjustable strap assembly. The head-mounted display device also includes a see-through display coupled to the frame.

In some implementations, the head-mounted display device further includes a first follower (e.g., protrusion, slidable member, etc.) that slidably couples the first temple housing to the first side strap; and a second follower (e.g., protrusion, slidable member, etc.) that slidably couples the second temple housing to the second side strap.

In some implementations, the first follower includes an elongate protrusion that can slide forward and backward within an elongate slot of the first temple housing responsive to pivoting of the first temple housing with respect to the frame. The second follower may include an elongate protrusion that can slide forward and backward within an elongate slot of the second temple housing responsive to pivoting of the second temple housing with respect to the frame.

In some implementations, each of the first side strap and the second strap includes a rack, and the adjustment mechanism of the adjustable strap assembly includes a pinion engaged with the rack of the first side strap and with the rack of the second side strap and a knob configured to cause rotation of the pinion in order to adjust the circumferential size defined by the first side strap, the second side strap, and the frame.

In some implementations, the adjustment mechanism of the adjustable strap assembly further includes a tension mechanism (e.g., stop mechanism, one or more gears engaged with a tension member, etc.) that resists rotation of the knob until a threshold force is overcome.

In some implementations, the adjustment mechanism of the adjustable strap assembly further includes a pad configured to engage a back of a head of the wearer.

In some implementations, the head-mounted display device further includes a forehead support including a first end pivotably coupled to the first side strap; a second end pivotably coupled to the second side strap; and a central support coupled to the frame.

In some implementations, the head-mounted display device further includes a top strap removably coupled at a first end to the forehead support and at a second end to the adjustment mechanism of the adjustable strap assembly.

In some implementations, the frame further includes a nose pad (e.g., nose support member, etc.) configured to engage a nose of the wearer.

In accordance with several implementations, a head-mounted display device includes a frame extending from a first end to a second end, the first end configured to be positioned adjacent a first temple of a wearer (e.g., a surgeon or other user), and the second end configured to be positioned adjacent a second temple of the wearer. The head-mounting display device further includes a head mounting assembly configured to retain the frame in a position on a head of the wearer; a see-through display; and a flashlight assembly (e.g., headlamp assembly, headlight assembly, etc.) detachably coupled to the frame. The frame includes a flashlight mounting socket including a first rod (e.g., post, protrusion, shaft, etc.) that defines a pivot axis; and a second rod (e.g., post, protrusion, shaft, etc.) positioned parallel to the first rod. The flashlight assembly includes a first recess (e.g., opening, socket, depression, etc.) shaped to engage and pivot about the first rod of the flashlight mounting socket; a second recess (e.g., opening, socket, depression, etc.) shaped to engage the second rod of the flashlight mounting socket, the second recess being oriented such that the first recess cannot disengage the first rod when the second recess is engaged with the second rod; and a movable latch (e.g., hook, coupler, etc.) configured to selectively retain the second recess in engagement with the second rod.

In some implementations, the head-mounted display device further includes a spring or other biasing structure that biases the movable latch toward a position that retains the second recess in engagement with the second rod.

In some implementations, the flashlight assembly includes a flashlight (e.g., headlight, headlamp, etc.); a mounting base that includes the first recess, the second recess, and the movable latch; and one or more arms that pivotably couple the flashlight to the mounting base.

In some implementations, the flashlight mounting socket further includes one or more electrical contacts configured to electrically couple to a corresponding one or more electrical contacts of the flashlight assembly.

In some implementations, the frame further includes a nose pad (e.g., nose support member, etc.) configured to engage a nose of the wearer.

In accordance with several implementations, a head-mounted display device includes a frame extending from a first end to a second end, the first end configured to be positioned adjacent a first temple of a wearer (e.g., a surgeon or other user), and the second end configured to be positioned adjacent a second temple of the wearer. The head-mounted display device further includes a head mounting assembly configured to retain the frame in a position on a head of the wearer. The head-mounted display device also includes a see-through display assembly (e.g., augmented-reality display, stereoscopic display, glasses, visor, etc.) coupled to the frame. The see-through display assembly includes a display assembly frame; a waveguide lens coupled to the display assembly frame; an anterior lens affixed to the waveguide lens or to the display assembly frame in front of the waveguide lens; a posterior lens frame detachably coupled to the display assembly frame using at least one of a snap fit, a friction fit, or a clip; and a posterior lens affixed to the posterior lens frame.

In some implementations, the head-mounted display device further includes a first seal between the anterior lens and the waveguide lens and a second seal between the posterior lens frame and the waveguide lens.

In some implementations, the posterior lens frame includes a first protrusion (e.g., clip, snap, etc.) at a top of the posterior lens frame that fits into a first corresponding recess (e.g., opening, hole, slot, etc.) of the display assembly frame. The posterior lens frame includes a second protrusion (e.g., clip, snap, etc.) at a bottom of the posterior lens frame that forms a snap fit with a second corresponding recess (e.g., opening, hole, slot, etc.) of the display assembly frame.

In some implementations, the see-through display assembly is coupled (e.g., rotatably, pivotably, movably, or slidably coupled) to the frame such that a tilt angle (e.g., pantoscopic tilt angle) can be adjusted.

In some implementations, the see-through display assembly is coupled (e.g., rotatably, pivotably, movably, or slidably coupled) to the frame with a pantoscopic tilting assembly that includes an arc-shaped slot that rotatably, pivotably, movably, or slidably couples a portion of the see-through display assembly to a portion of the frame and a detent mechanism including a spring-loaded pin or ball and a plurality of detents, the detent mechanism configured to selectively retain the see-through display assembly in any of a plurality of predefined positions with respect to the frame.

In some implementations, the detent mechanism further includes a guide member slidably engaged with the arc-shaped slot, the guide member configured to apply a force to the spring-loaded pin or ball to move the spring-loaded pin or ball from one of the plurality of detents to another of the plurality of detents.

In some implementations, the frame further includes a nose pad (e.g., nose support member, etc.) configured to engage a nose of the wearer.

In accordance with several implementations, a system includes a head-mounted display (HMD), including a frame configured to be mounted on a head of a user (e.g., a surgeon or other user); and a display (including, e.g., an augmented-reality display, a stereoscopic display, glasses, goggles, a head-up display, a visor, etc.), which is (i) connected to the frame and configured to rotate relative to a frontal plane of the user for setting a tilt angle (e.g., pantoscopic tilt angle) of the display, and (ii) at least partially transparent and configured to display to the user, an augmented reality (AR) image including a virtual reality (VR) image presented over a scene on a body of a patient; and at least one processor configured to (i) receive one or more anatomical images of the patient and signals indicative of at least the position of the display relative to the scene; and (ii) render the AR image to the display.

In some implementations, the frame includes an adjustable head mounting assembly including adjustable temple arms, which are placed over ears of the user and are configured to be adjusted for conforming with at least a section of temples of the user; an adjustable nose pad (e.g., nose support member, etc.), which is placed over a nose of the user and is configured to conform to a shape of at least part of the nose; and a housing, which is connected to the temple arms and nose pad.

In some implementations, at least one of the temple arms includes first and second sections and first and second tilting assemblies, wherein the first tilting assembly is configured to tilt the first section relative to the frame, and the second tilting assembly is configured to rotate the second section relative to the first section.

In some implementations, the second tilting assembly includes a rocker arm, which is configured to rotate about a hinge relative to a longitudinal axis of the first section.

In some implementations, the first section has an opening, and when the rocker arm is rotating, the opening is configured to contain at least part of the rocker arm.

In some implementations, the rocker arm includes a cushion, which is made from a viscoelastic foam shaped to conform with a nape of the user and to improve a clamping between the frame of the HMD and the head of the user.

In some implementations, the cushion includes a material selected from a list of materials consisting essentially of at least one of (i) silicone, (ii) neoprene, and (iii) polyurethane.

In some implementations, the cushion includes a sponge.

In some implementations, the second tilting assembly includes an alloy, which is coated by a viscoelastic foam and is shaped to conform with a nape of the user.

In some implementations, (i) the first and second sections, (ii) the first and second tilting assemblies, and (iii) the nose pad, are adapted to provide the user with two or more degrees of freedom (DOFs) for adjusting the frame to conform with a contour of the head of the user.

In some implementations, the second tilting assembly includes an array of rocker arms, each of the rocker arms is configured to rotate about a respective hinge.

In some implementations, the array of rocker arms is mounted on a common bar, and including an additional hinge, and wherein the common bar is configured to rotate about the additional hinge.

In some implementations, the frame includes an adjustable head mounting assembly including a first side strap having a first end coupled to a first end of the frame; a second side strap having a first end coupled to a second end of the frame; and an adjustment mechanism (e.g., a knob, a rack and pinion, a mechanism that uses friction, etc.) configured to adjust a position of a second end of the first side strap with respect to a second end of the second side strap, in order to adjust a circumferential size defined by the first side strap, the second side strap, and the frame.

In some implementations, the system further includes a first temple housing pivotably coupled to the first end of the frame and slidably coupled to the first side strap; and a second temple housing pivotably coupled to the second end of the frame and slidably coupled to the second side strap.

In some implementations, at least one eye has a first optical axis, and wherein an optical engine of the display has a second optical axis, and wherein the pantoscopic tilt angle is set for aligning the second optical axis with the first optical axis.

In some implementations, the HMD includes a pantoscopic-tilting assembly (PTA), which is connected to the frame and the display, and is configured to rotate the second optical axis relative to the first optical axis for adjusting the pantoscopic tilt angle.

In some implementations, the PTA includes a hinge connecting between the first and second optical axes.

In some implementations, the PTA includes a bar, which is coupled to the optical engine including the display, and an edge of the bar is coupled to the hinge, and wherein the hinge is adapted to rotate the bar relative to the first axis of the frame.

In some implementations, the PTA includes a virtual axis including at least two parts other than a hinge, and adapted to rotate the second optical axis relative to the first optical axis.

In some implementations, the virtual axis includes (i) a bar coupled to an optical engine including the display and to a rotatable section of a disc having a slit, and (ii) an element configured to be inserted into the slit and to be moved along the slit and relative to the slit in a tangential direction.

In some implementations, the virtual axis includes an arm including first, second and third sections, wherein the first section is coupled to an optical engine including the display, the second section is coupled to the frame, and the third section coupled between the first and second sections and configured to bend in response to a force applied to the PTA for adjusting the pantoscopic tilt angle.

In some implementations, the virtual axis includes (i) a rigid arm coupled to the frame, and (ii) a flexible arm, which is coupled to an optical engine including the display, and wherein, the flexible arm is adapted to transform from an elastic deformation to a plastic deformation, and to retain a shape obtained in response to a force applied to the PTA for adjusting the pantoscopic tilt angle.

In some implementations, the PTA further includes a detent mechanism including a spring-loaded pin or ball and a plurality of detents, the detent mechanism configured to selectively retain the display in any of a plurality of predefined positions with respect to the frame.

In accordance with several implementations, a head-mounted display device includes a frame extending from a first end to a second end; a head mounting assembly configured to be adjustable and to retain the frame in a position on a head of the user (e.g., a surgeon or other user); a display (including, e.g., an augmented-reality display, a stereoscopic display, glasses, a visor, etc.) that is at least partially transparent and configured to display to the user an augmented reality (AR) image including a virtual reality (VR) image presented over a scene on a body of a patient; a pantoscopic tilting assembly that pivotably couples (e.g., rotatably, pivotably, movably, or slidably couples) the display to the frame such that a pantoscopic tilt angle can be adjusted; a first temple housing pivotably coupled to the first end of the frame by a first tilting assembly; and a second temple housing pivotably coupled to the second end of the frame by a second tilting assembly. At least one of the first temple housing or the second temple housing includes at least one processor configured to receive one or more anatomical images of the patient and signals indicative of at least a position of the display relative to the scene, and to render the AR image to the display.

In some implementations, the head mounting assembly includes an adjustable head strap configured to engage at least a back of a head of the user and a forehead of the user.

In some implementations, the first temple housing and the second temple housing are each part of the head mounting assembly.

In some implementations, the head mounting assembly further includes an adjustable nose pad (e.g., nose support member, etc.) configured to conform to a shape of at least a part of a nose of the user.

In some implementations, the pantoscopic tilting assembly includes a slot positioned to enable a pivoting element to slide tangential to the slot, the pivoting element configured to be locked at one or more predefined positions with respect to the slot.

In accordance with several implementations, a method of pairing head-mounted displays and workstations in medical center networks includes introducing a communication device of a head-mounted display into a first network; initiating pairing of the communication device of the head-mounted display to a first workstation of the first network using previous connection parameters, when the communication device of the head-mounted display is previously known to the first network. The method also includes initiating pairing of the communication device of the head-mounted display to the first workstation of the first network using a key exchanging process that generates new connection parameters, when the communication device of the head-mounted display is not previously known to the first network. The method further includes exchanging data between the first workstation and the communication device of the head-mounted display during a surgical operation, to enable the head-mounted display to display to a user an augmented reality (AR) image including a virtual reality (VR) image presented over a scene on a body of a patient. In some implementations, the head-mounted display comprises any of the head-mounted displays or head-mounted display devices disclosed herein.

In some implementations, the method further includes responsive to pairing not being completed successfully within a predefined time limit, initiating pairing of the communication device of the head-mounted display to a second workstation of the first network.

In some implementations, the method further includes unpairing the communication device of the head-mounted display from the first workstation of the first network; initiating pairing of the communication device of the head-mounted display to a second workstation of a second network; and exchanging data between the second workstation and the communication device of the head-mounted display during a surgical operation, to enable the head-mounted display to display to a user an augmented reality (AR) image including a virtual reality (VR) image presented over a scene on a body of a patient.

Also described and contemplated herein is the use of any of the apparatus, systems, or methods for the treatment of a spine through a surgical intervention.

Also described and contemplated herein is the use of any of the apparatus, systems, or methods for the treatment of an orthopedic joint through a surgical intervention, including, optionally, a shoulder, a knee, an ankle, a hip, or other joint.

Also described and contemplated herein is the use of any of the apparatus, systems, or methods for the treatment of a cranium through a surgical intervention.

Also described and contemplated herein is the use of any of the apparatus, systems, or methods for the treatment of a jaw through a surgical intervention.

Also described and contemplated herein is the use of any of the apparatus, systems, or methods for the diagnosis of a spinal abnormality.

Also described and contemplated herein is the use of any of the apparatus, systems, or methods for the diagnosis of a spinal injury.

Also described and contemplated herein is the use of any of the apparatus, systems, or methods for the diagnosis of joint damage.

Also described and contemplated herein is the use of any of the apparatus, systems, or methods for the diagnosis of an orthopedic injury.

Also described and contemplated herein is the use of any of the apparatus, systems, or methods in non-medical applications, such as gaming, driving, product design, shopping, manufacturing, athletics or fitness, navigation, remote collaboration, and/or education.

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features. The embodiments disclosed herein may be embodied or carried out in a manner that achieves or optimizes one advantage or group of advantages as taught or suggested herein without necessarily achieving other advantages as may be taught or suggested herein. The systems and methods of the disclosure each have several innovative aspects, no single one of which is solely responsible for the desirable attributes disclosed herein.

The present disclosure will be more fully understood from the following detailed description of the embodiments thereof, taken together with the drawings, claims and descriptions above. A brief description of the drawings follows.

BRIEF DESCRIPTION OF THE DRAWINGS

Non-limiting features of some embodiments of the inventions are set forth with particularity in the claims that follow. The following drawings are for illustrative purposes only and show non-limiting embodiments. Features from different figures may be combined in several embodiments. It should be understood that the figures are not necessarily drawn to scale. Distances, angles, etc. are merely illustrative and do not necessarily bear an exact relationship to actual dimensions and layout of the devices illustrated.

DETAILED DESCRIPTION

Some image-guided surgery systems may apply augmented reality (AR) techniques for displaying, over structures inside a patient's body intended to be operated on, one or more anatomical images of the structures (e.g., bones, joints, soft tissue, organs, cartilage). For example, the system may comprise a suitable head-mounted display (HMD), which is configured to display to a surgeon or other wearer, three-dimensional (3D) anatomical images, two-dimensional (2D) or 3D cross sections, tool trajectory, tool depth and additional information that assists the surgeon or other wearer to visualize structures (e.g., vertebrae, joints, bones, soft tissue, organs) that are hidden from actual view by overlying layers of tissue (for example, but not by way of limitation, during a minimally invasive interventional procedure or surgery that does not require open surgery to expose a target region of the body).

Several embodiments of the disclosure that are described herein provide assemblies and methods that may be implemented in conjunction with several types of HMDs for improving the quality of image-guided surgical or other interventional procedures, including spinal surgery and other sorts of orthopedic procedures (as well as other types or categories of procedures, such as dental procedures, cranial procedures, neurological procedures, joint surgery (e.g., shoulder, knee, hip, ankle, other joints), heart surgery, bariatric surgery, facial bone surgery, neurosurgery, and the like), including minimally invasive procedures that do not require open surgery but can be performed through small incisions (e.g., self-sealing incisions that do not require staples or stitches). Note that each of the HMDs described hereinafter may comprise a basic configuration and additional optional components and assemblies that may be implemented in one or more of the HMDs in addition to the basic configuration.

The systems, devices and methods described may be used in connection with other medical procedures (including therapeutic and diagnostic procedures) and with other instruments and devices or other non-medical display environments. The methods described herein further include the performance of the medical procedures (including but not limited to performing a surgical intervention such as treating a spine, shoulder, hip, knee, ankle, other joint, jaw, cranium, etc.). Although medical applications are well-suited for several embodiments, non-medical applications also benefit from many embodiments described herein. For example, non-medical applications may involve consumer or commercial applications such as athletics and fitness, gaming, driving, product design, navigation, manufacturing, logistics, shopping and commerce, educational training, remote collaboration, etc. The surgeon referenced herein may be a consumer or other wearer or user.

Figure 1:
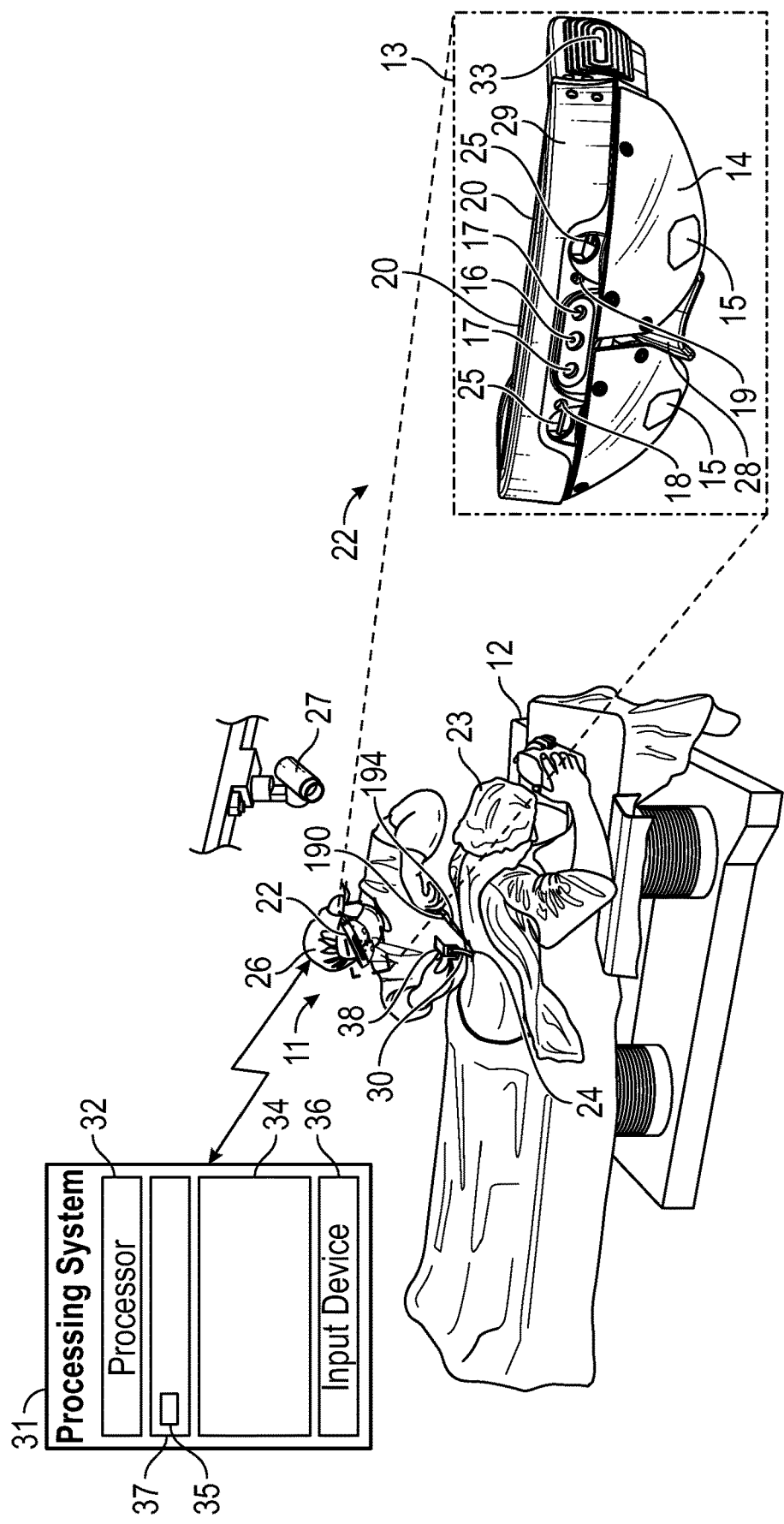
FIG. 1 is a schematic pictorial illustration of an augmented-reality based image-guided surgery system comprising a head mounted display (HMD).

FIG. 1 is a schematic pictorial illustration of an augmented-reality (AR) based image-guided system 11 used to carry out a surgical or other interventional medical procedure, in accordance with an embodiment of the disclosure.

In one example, the surgical procedure (e.g., minimally invasive surgical procedure or open surgical procedure) comprises one or more orthopedic procedures performed on one or more vertebrae of the spine of a human subject, referred to herein as a patient 23, who is lying on an operating table 12. One example application is a Lateral Lumbar Interbody Fusion (LLIF) procedure for treating disc problems in the lower (e.g., lumbar or lumbosacral) back of patient 23. In other embodiments, the techniques described below are applicable, mutatis mutandis, to other sorts of surgical procedures carried out on other vertebrae (e.g., lumbar vertebrae, thoracic vertebrae, cervical vertebrae, sacral vertebrae), any suitable organ, bone(s), joints (e.g., sacroiliac joints, knee joints, shoulder joints, ankle joints, hip joints) or other tissue of patient 23. In non-limiting examples, system 11 may be used in other sorts of procedures performed on bone tissue of patient 23, such as in cranial procedures, oral procedures and in maxillofacial surgery, knee surgery, hip surgery, shoulder surgery. Moreover, system 11 may also be used, mutatis mutandis, in surgical or other interventional (e.g., therapeutic or diagnostic) procedures of soft tissue (e.g., neuro procedures, cranial procedures, joint repair or reconstruction procedures, scoping procedures, arthroscopic procedures, ablation procedures, etc.). System 11 may also be used in non-medical applications, including consumer or commercial applications such as athletics and fitness, gaming, driving, product design, navigation, manufacturing, logistics, shopping and commerce, educational training, remote collaboration, etc. and the wearer may be a person other than a surgeon or medical professional (such as a consumer or other user).

In some embodiments, during the procedure, a medical professional, also referred to herein as a physician or a surgeon 26, uses a suitable tool for making an incision 24 into the patient's back. In some embodiments, surgeon 26 inserts an anchoring device, such as spinous process clamp 30 into the incision 24, so that opposing jaws of the clamp 30 are located on opposite sides of the spinous processes. Subsequently, surgeon 26 slides the clamp 30 over the vertebral laminas, and adjusts the clamp 30 to grip one or more spinous processes, selected by the surgeon 26, of the patient 23. One optional implementation of clamp 30 is described in more detail in PCT Application Publication WO 2022/079565, whose disclosure is incorporated herein by reference.

In some embodiments, clamp 30 acts as a support for a patient marker 38, which is attached rigidly to the clamp. During substantially all of the procedure, e.g., during the initial, as well as the subsequent stages, patient marker (not shown), which is used as a fiducial for patient 23, since due to its rigid connection to the patient 23, any movement of the patient 23 is reflected in a corresponding motion of the patient marker 38. Thus, at an initial stage of the procedure, marker 38 is registered with the anatomy of patient 23.

In some embodiments, the anchoring device may be a pin inserted into a bone of the patient, e.g., iliac bone. One optional implementation of such a pin is described in more detail in PCT Application Publication No. WO 2023/281395, whose disclosure is incorporated herein by reference.

Embodiments related to registration tools, markers, marks, adaptors, and methods are described in detail, for example, in U.S. Patent Application Publication 2022/0071712, U.S. Patent Application Publication 2022/0142730, U.S. Pat. No. 10,939,977 and U.S. Patent Application Publication 2021/0161614, whose disclosures are all incorporated herein by reference.

In some embodiments, system 11 comprises (i) a head-mounted display (HMD) 22, which is worn by surgeon 26 and is described in detail hereinafter, (ii) one or more surgical and/or diagnostic tools, such as but not limited to a surgical tool 190, and one or more reflectors, such as a reflector 194, mounted on tool 190. The reflectors may comprise markers for registration and/or calibration purposes.

Reference is now made to an inset 13 showing one optional implementation of HMD 22 shown in a front view.

In the context of the present disclosure, the term "front view" refers to the view of HMD 22 as seen by the eyes of a person located in front of surgeon 26 wearing HMD 22. In the example of FIG. 1, HMD 22 comprises a visor-based optical engine comprising a processor 33, a communication device (shown and described in connection with FIGS. 2B and 18 below) configured to exchange signals or transmissions with entities external to HMD 22, such as a workstation and a remote control tablet described in connection with FIG. 18 below. Typically, the communication device is configured to send and receive the signals or transmissions using suitable wireless techniques, such as but not limited to Wi-Fi (also referred to herein as Wi-Fi) and Bluetooth wireless communication protocols or standards. HMD 22 further comprises one or more power supply devices, such as but not limited to a battery (shown in FIG. 20 below) and a supercapacitor or ultracapacitor described in more detail below.

In some embodiments, processor 33 is configured to receive information, such as anatomical images, and signals from one or more sensors (described below) and other entities of system 11, and to display to surgeon 26 one or more images overlaid on the surgeon's actual view of a portion of the exterior of the patient's body. For example, during a spinal surgery, processor 33 is configured to produce an augmented reality (AR) display that may show 3D images of the vertebrae overlaid on the patient's back, as seen by the patient's eyes. Certain embodiments related to the images, signals and AR display are described in more detail below.

In some embodiments, HMD 22 comprises a visor 14 of a visor-based optical engine for each eye of surgeon 26, which is not shown in FIG. 1, but example implementations thereof are shown and described hereinafter in connection with FIG. 2A below.

In some embodiments, the optical engine (OE) comprises (i) a projector configured to project the AR image produced by the processor, and (ii) optics configured to direct the projected AR image to the visor, also referred to herein as an AR display 15.

In various embodiments, the projector comprises one or more light sources and/or image sources. As one example, the projector comprises an organic light-emitting diode (OLED)-based image source and display comprising a matrix of LEDs having a total size (e.g. diagonal size) of about 0.5 inch. Other sizes of displays may also be implemented.

In the context of the present disclosure and in the claims, the term "AR image" and grammatical variations thereof refer to a virtual reality (VR) image displayed over or integrated with a display including at least partially transparent portions and having a scene in the background, so that a combination of the VR image and the scene is referred to herein as the AR image.

In some embodiments, AR display 15 is configured to display to surgeon 26, the AR image produced by processor 33 by reflecting the AR image into the pupil of the eye of surgeon 26. The optical engine is shown and described in connection with FIG. 2A below.

In other embodiments, the OE of HMD 22 may have different configurations and may be based on different techniques, such as but not limited to a waveguide and liquid crystal-based OE described in more detail in connection with FIGS. 3 and 29A-29E below.

In some embodiments, HMD 22 comprises one or more light sources for tracking applications configured to direct light beams to the surface of the organ or treatment region in question (e.g., back) of patient 23. In some embodiments, the light source comprises a pair of infrared (IR) LED projectors 17 configured to direct IR light beams to the surface of the treatment region. In other embodiments, the light source may comprise any other suitable type of one or more light sources, configured to direct any suitable wavelength or band of wavelengths of light, and mounted on HMD 22 or elsewhere in the operating room.

In some embodiments, HMD 22 comprises a camera 16. In some embodiments, camera 16 comprises a red green blue (RGB) camera having an IR-pass filter, referred to herein as an IR camera and also referred to herein as an IR tracker. In other embodiments, camera 16 may comprise a monochrome camera configured to operate in the IR wavelengths. Camera 16 is configured to capture images including both reflectors 194 and markers 38 and markers (not shown) attached to patient 23. Although camera 16 in FIG. 1 is mounted on HMD 22, these images may additionally, or alternatively, be captured by a suitable camera mounted at any other suitable position on the head or body of surgeon 26 or mounted at any suitable position in the operating room. Camera 16 is configured to produce signals indicative of the captured image and to send them to processor 33, also referred to herein as infrared (IR) images for embodiments incorporating an IR camera. In such embodiments, processor 33 is configured to process the IR images acquired by camera 16, in order to calculate the location and orientation of HMD 22 tracking system reference point relative to the one or more surgical tools (e.g., surgical tool 190) and the organ, bone, joint, or other target treatment region or location in question.

In several embodiments, the tracking application that is based on the images produced by camera 16 requires monochromatic images. In some embodiments, camera 16 comprises a color image sensor. The addition of colors in the tracking images may, in at least some instances, lower image quality due to the de-bayering interpolation applied to the color pixels for producing a contiguous image based on the separated RGB pixels (two red, one green and one blue pixels) of the Bayer filter of the RGB image sensor.

In some embodiments, camera 16 comprises compact sensors (such as sensors designed for consumer products) having a color array filter (CAF) (also denoted a Bayer filter) giving each of the different color channels a unique response. By adding an external band-pass filter, the raw pixel data received from camera 16, can be treated as monochrome data.

In some embodiments, the band-pass filter (BPF) is applied to a selected section of the infrared zone (e.g., between about 830 nm and 870 nm, or using any other suitable range within the wavelengths of the infrared spectrum).

In some embodiments, processor 33 (or any other controller) is configured to apply to each channel, a respective single gain value, so as to offset the effects of the Bayer filter on the filter's pass band.

In some embodiments, the basic configuration of HMD 22 comprises the aforementioned processor 33, communication device (wireless and/or wired), camera 16 (e.g., an IR camera), projectors 17 (e.g., IR projectors), display 15 and the optical engine comprising the projector (shown in FIG. 2A below) on display 15.

In some embodiments, HMD 22 comprises components, which are additional to the basic configuration. For example, HMD 22 comprises an inertial measurement unit (IMU) 18, which is configured to produce position signals indicative of the position and orientation of HMD 22 at a frequency level between about 1 Hz and 10 kHz (e.g., between 1 Hz and 50 Hz, between 1 Hz and 200 Hz, between 50 Hz and 250 Hz, between 100 Hz and 200 Hz, between 50 Hz and 1 kHz, between 100 Hz and 10 kHz, overlapping ranges thereof, or any value within the recited ranges). Based on the position signals received from IMU 18, processor 33 may be configured to improve the response time of system 11, e.g., to any relative motion between HMD 22, and the organ in question (or other target treatment anatomy or region) of patient 23.

In some embodiments, IMU 18 is configured to operate in conjunction with camera 16 (which typically operates at a frequency of about 60 frames per second or at any other suitable frequency corresponding to any other suitable number of frames per second) and to provide processor 33 with the position and orientation of HMD 22 with a reduced latency compared to images received from camera 16. In such embodiments, the position and orientation of HMD 22 can be calculated with the reduced latency obtained by using IMU 18. Moreover, in case the optical path between camera 16 and one or more of the markers is occluded, processor 33 may rely on the signals from IMU 18 for calculating the position of HMD 22 relative to the organ in question (or other target treatment anatomy or region).

In some embodiments, processor 33 is configured to conduct a registration between the coordinate systems of IMU 18 and camera 16 and a synchronization between the signals received from IMU 18 and camera 16.

In some embodiments, HMD 22 comprises one or more additional cameras 25 (e.g., a pair of red-green-blue (RGB) cameras). Each additional camera 25 (e.g., RGB camera) is configured to produce high resolution (HR) images (e.g., HR RGB images) of the organ being operated on (or other target treatment anatomy or region), and processor 33 is configured to display the HR images on the display 15 of HMD 22.

Moreover, because HMD 22 comprises a pair of additional cameras 25, which are positioned at a known distance from one another, processor 33 is configured to produce a stereoscopic 3D image of the site being operated on (e.g., the organ in question or other target treatment anatomy or region). Such techniques are also referred to herein as a digital loupe, for augmented reality near eye display, and are described in more detail, for example in U.S. Provisional Patent Application 63/234,272, and in PCT Publication No. WO2023/021450, the disclosure of both of which are incorporated herein by reference.

In other embodiments, HMD 22 may comprise any other suitable number of additional cameras 25 having similar features to that of RGB cameras. Alternatively, at least one of the additional cameras 25 may have different features compared to that of RGB cameras.

In some embodiments, each additional camera 25 is further configured to acquire images containing a structured light pattern, which is directed to the site being operated on by surgeon 26, and based on the image of the structured light pattern, processor 33 is configured to improve the precision of the 3D imaging of the site being operated on.

In some embodiments, the structured light projector is configured to direct a large number of beams (e.g., hundreds, or thousands) to the organ in question (or other target treatment anatomy or region), so as to enable 3D imaging (and most importantly depth imaging) of the organ (or other target treatment anatomy or region). In some embodiments, the wavelength of the structured light must be suitable for producing spots on the skin and/or internal tissue being operated. In some examples, the structured light may comprise green laser beams, blue laser beams, red laser beams, infrared laser beams or beams of any other suitable wavelength or range of wavelengths.

In some examples, the structured light comprises a visible wavelength (e.g., green), so that cameras 25 produce images of green spots on the skin and/or on the surface of the tissue being operated on. Based on the images received from cameras 25, processor 33 is configured to produce the 3D image of the organ (or other target treatment anatomy or region) being operated on. The structured light is described in more detail in connection with FIG. 16 below.

In other cases, the structured light comprises beams having a non-visible wavelength, such as infrared wavelengths. In some embodiments, processor 33 is configured to produce one or more images of the IR spots on the surface of the organ in question (or other target treatment anatomy or region). The images may be two-dimensional (2D), or typically 3D, using images (e.g., IR images) acquired, for example, by camera 16 and/or using additional IR cameras that may be mounted on HMD 22 or at a known position in the operation room. The 2D and 3D images may be produced by processor 33 using the same techniques, mutatis mutandis, described above for producing the images having the visible spots of structured light.

In some embodiments, HMD 22 comprises a housing 29, which is configured to package all the components described above. In some embodiments, housing 29 comprises a surface 20, which is configured to receive a headlight assembly mounted thereon. Several types of headlight assemblies and mounting techniques thereof to surface 20 are described in detail in connection with FIGS. 4-8 and 27A-28F below.

In some embodiments, HMD 22 comprises a nose pad 28, which is adjustable and is configured to support HMD 22 over the nose of surgeon 26. Several embodiments related to the structure and functionality of nose pad 28 are described in detail in connection with FIG. 12 below.

In some embodiments, HMD 22 comprises one or more light sensors 19, also referred to herein as an ambient light sensor (ALS), which is configured to produce one or more signals indicative of the light in the ambient area surrounding HMD 22. Based on the signals received from light sensor 19, processor 33 is configured to adjust the brightness of the AR image presented on display 15. Additionally, or alternatively, based on the signals received from light sensor 19, processor 33 is configured to adjust the power applied to a light source mounted on MHD 22 and/or to a lighting assembly 27 described herein.

In some embodiments, HMD 22 comprises an IR-based proximity sensor (not shown), which is configured to produce signals for various uses, such as but not limited to hand-gesture tracking.

Reference is now made back to the general view of FIG. 1. Additionally, or alternatively to the aforementioned headlight assemblies, system 11 may comprise a lighting assembly 27, which is mounted at any suitable position of the operating room and is configured to direct white light, or any other suitable wavelength or range of wavelengths of light, to the site being operated in the organ in question (or other target treatment anatomy or region) of patient 23.

During the surgical or other interventional procedure, surgeon 26 wears HMD 22, which is configured to present to surgeon 26 the captured and stored images as well as additional calculated information based on the tracking system that are aligned with the organ (or other target treatment anatomy or region) being operated on.

In some embodiments, in serving as a fiducial, marker 38 performs two functions: in a first function, the marker is used to maintain registration between frames of reference of HMD 22 and the patient's anatomy, and in a second function, the marker is used to ascertain where the head and gaze of surgeon 26 is located with respect to the organ in question (or other target treatment anatomy or region) of patient 23.

During the initial stage of the procedure, a registration marker (not shown) is placed on the patient's back or other anatomical location, and is used to implement the registration of patient marker 38 with the anatomy of patient 23. In contrast to patient marker 38, the registration marker, in some implementations, is only used during the initial stage of the procedure, e.g., for the registration of the patient marker 38, and once the registration has been performed, for the subsequent procedure stages the registration marker may be removed from the patient's back or other anatomical location.

In some embodiments, system 11 comprises a processing system 31, which is communicatively coupled, by cables and/or wirelessly, to HMD 22. In some embodiments, processing system 31 comprises a computer processor 32, a storage device 37 comprising stored images 35, a screen 34, and an input device 36 such as a pointing device, mouse, touchscreen input such as a touchpad or touchscreen display, keyboard, etc.

In some embodiments, processing system 31 is configured to analyze the images acquired by the one or more cameras of HMD 22, and to present over display 15, the aforementioned AR image to surgeon 26.

As described above, HMD 22 comprises processor 33 to carry out at least the functions described above, but in alternative embodiments, during operation HMD 22 is connected to processor 32 of processing system 31, so as to carry these processing and displaying functions remotely, and the AR images are displayed to surgeon 26 over display(s) 15. The functions or tasks described herein as being implemented by processor 32 may be implemented by processor 33, or vice-versa.

The configuration of HMD 22 is provided by way of example and is simplified for the sake of conceptual clarity. In some embodiments, the processor 32 and the processor 33 can share processing tasks and/or allocate processing tasks between the processors 32, 33. Each of the processors 32, 33 may consist essentially of one processor or more than one processor.

Figure 2A:
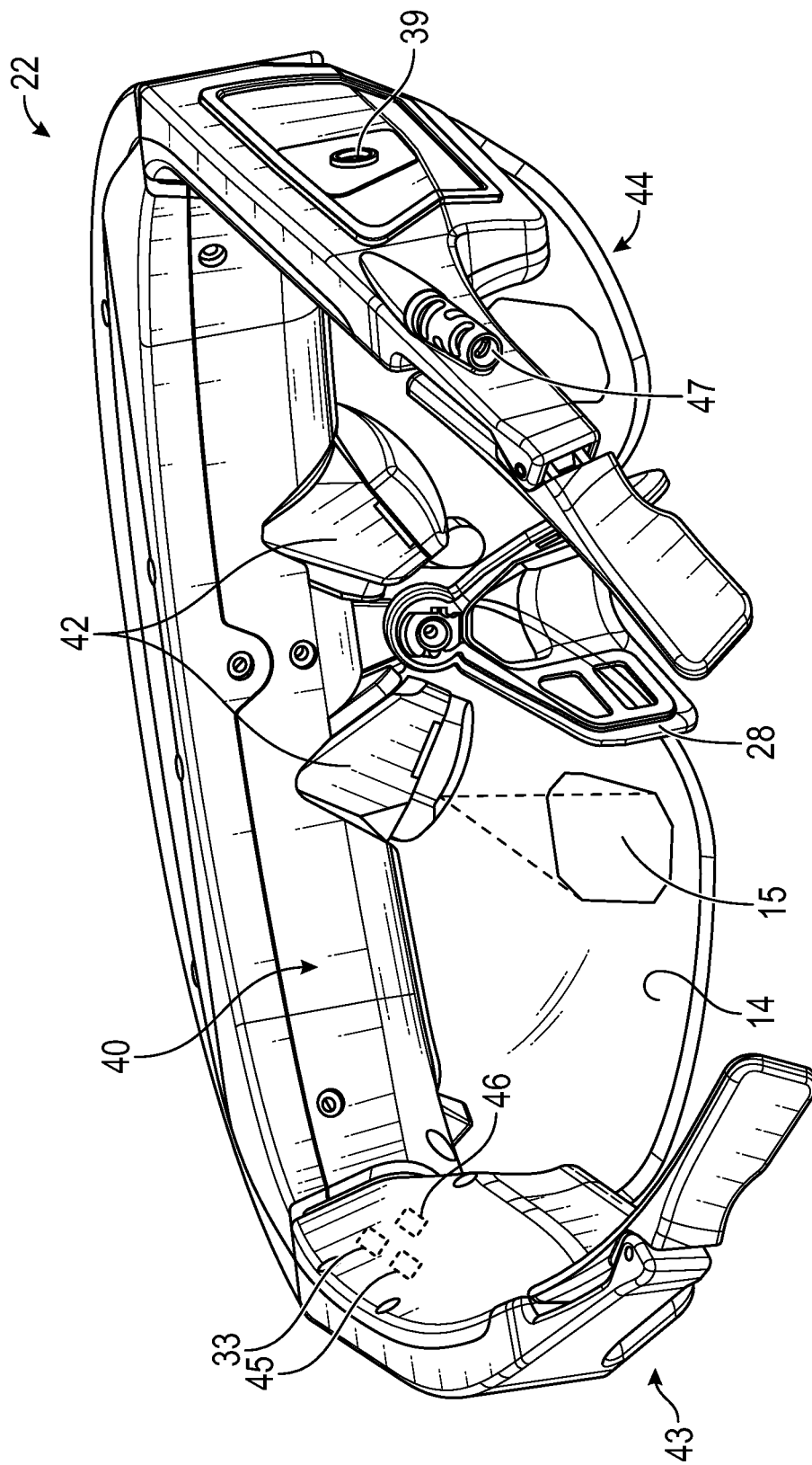
FIGS. 2A and 2B are schematic pictorial illustrations of HMDs for use in the system of FIG. 1.

FIG. 2A is a schematic rear view of HMD 22, in accordance with embodiments of the disclosure. In the context of the present disclosure, the term "rear view" refers to the view of HMD 22 as seen by the eyes of surgeon 26 while mounting HMD 22.

In some embodiments, HMD 22 comprises two optical engines (OEs) 40, one for each eye. In some embodiments, each OE 40 comprises an AR projector 42, which is configured to direct the AR image described in FIG. 1 above, to a respective AR display 15. In one example, each OE 40 comprises the OLED-based image source and display (described with reference to FIG. 1 above) configured to project the AR image produced by processor 33, and optics (e.g., one or more lenses and mirrors) configured to direct the AR image to AR display 15.

In some embodiments, AR display 15 is a section of visor 14, which is coated with one or more suitable layers, which is configured to reflect the projected VR image to the pupil of the respective eye, so that surgeon 26 can see the VR image overlaid on a scene of interest (e.g., the organ (or other target treatment anatomy or region) being operated on), in a way of augmented vision, virtual overlay on the real world.

In some embodiments, visor 14 is fully transparent or partially transparent so that when directing the gaze away from AR display 15, surgeon 26 can see the scene around him without having the AR image overlaid thereon.

In some embodiments, HMD 22 comprises two temple arms described herein, and nose pad 28 for mechanically supporting the mounting of HMD 22 over the head of surgeon 26. In the context of the present disclosure and in the claims, the term "temple arm" and grammatical variations thereof refer to a section of the frame of HMD 22 (or any other suitable type of HMD), which is coupled to housing 29 and is typically (but not necessarily) mounted on an ear of the user (e.g., surgeon 26) and is positioned in contact with at least a section of a respective temple of surgeon 26.

In some embodiments, a left temple arm 43 comprises processor 33 and optionally other devices, such as a wireless communication device 45 configured to exchange signals between HMD 22 and external entities, and a storage device 46 configured to store images, signals, program instructions and additional data of HMD 22. Note that processor 33, wireless communication device 45, and storage device 46 appear in dashed lines for being embedded within the inner volume of left temple arm 43.

In some embodiments, processor 33, wireless communication device 45, and storage device 46 may be disposed on one or more suitable substrates, such as one or more printed circuit boards (PCBs).

In some embodiments, all the devices are disposed on a single rigid PCB. In some embodiments, at least one of the PCBs may be flexible. Additional embodiments related to suitable types of flexible PCB are described in connection with FIG. 14 below.

In some embodiments, HMD 22 comprises a right temple arm 44, which comprises an on/off or standby button 39 configured to turn the power on when using HMD 22 and to turn the power off when HMD 22 is not in use.

In some embodiments, temple arms 43 and 44 are configured to be adjusted to the shape of the respective left and right temples of surgeon 26 or of any other user, and to be mounted on the ears of surgeon 26 in order to hold the weight of HMD 22 (in one example, together with a nose pad described below). The structure and functionality of temple arms 43 and 44 is described in detail in connection with FIGS. 9-11 below.

In some embodiments, nose pad 28 is configured to be adjusted to the shape of the nose of surgeon 26 or to the nose of any other user. The structure and functionality of nose pad 28, as well as embodiments related to the combination of nose pad 28 and temple arms 43 and 44 are described in detail in connection with FIG. 12 below.

Figure 2B:
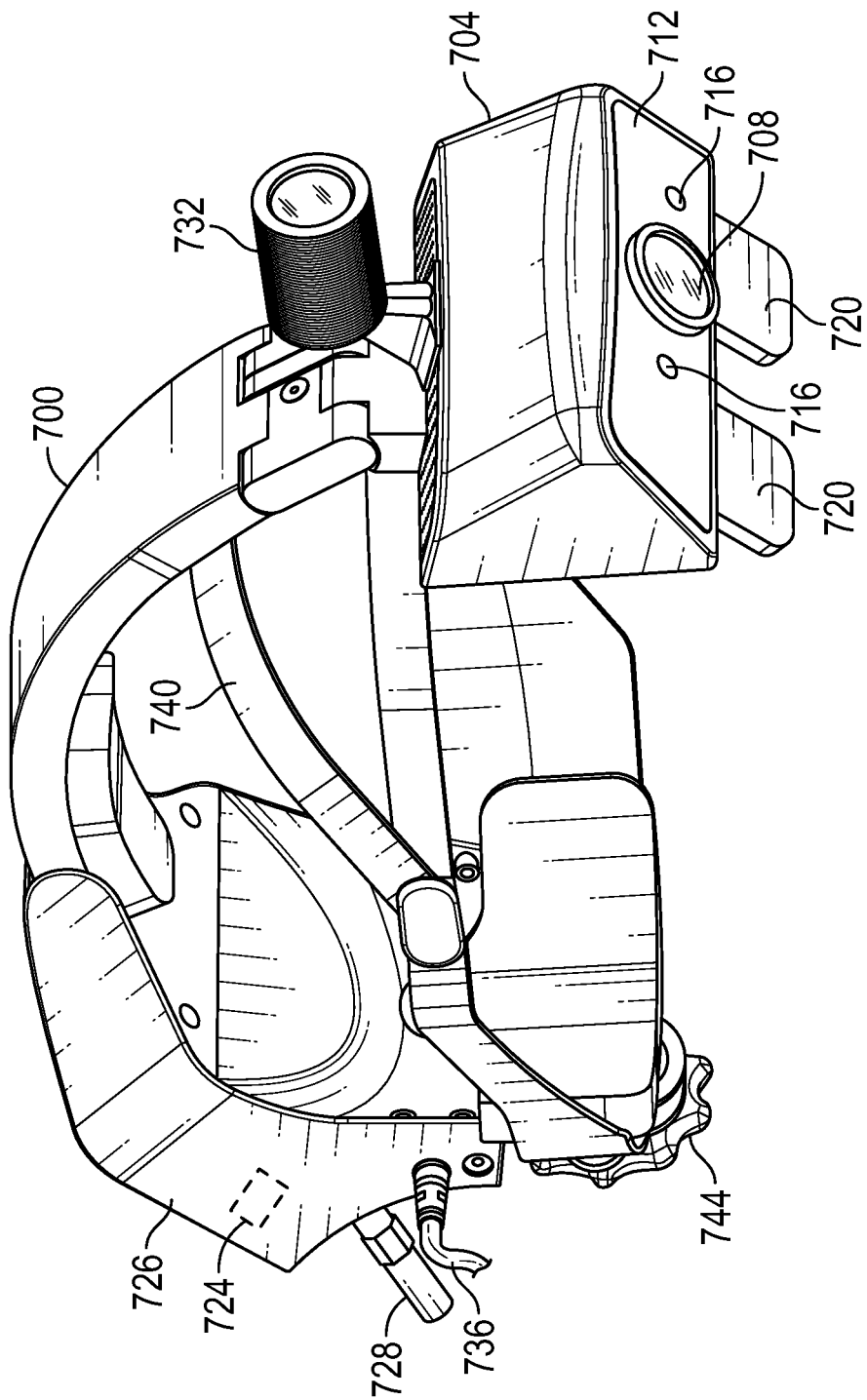
Figure 21A:
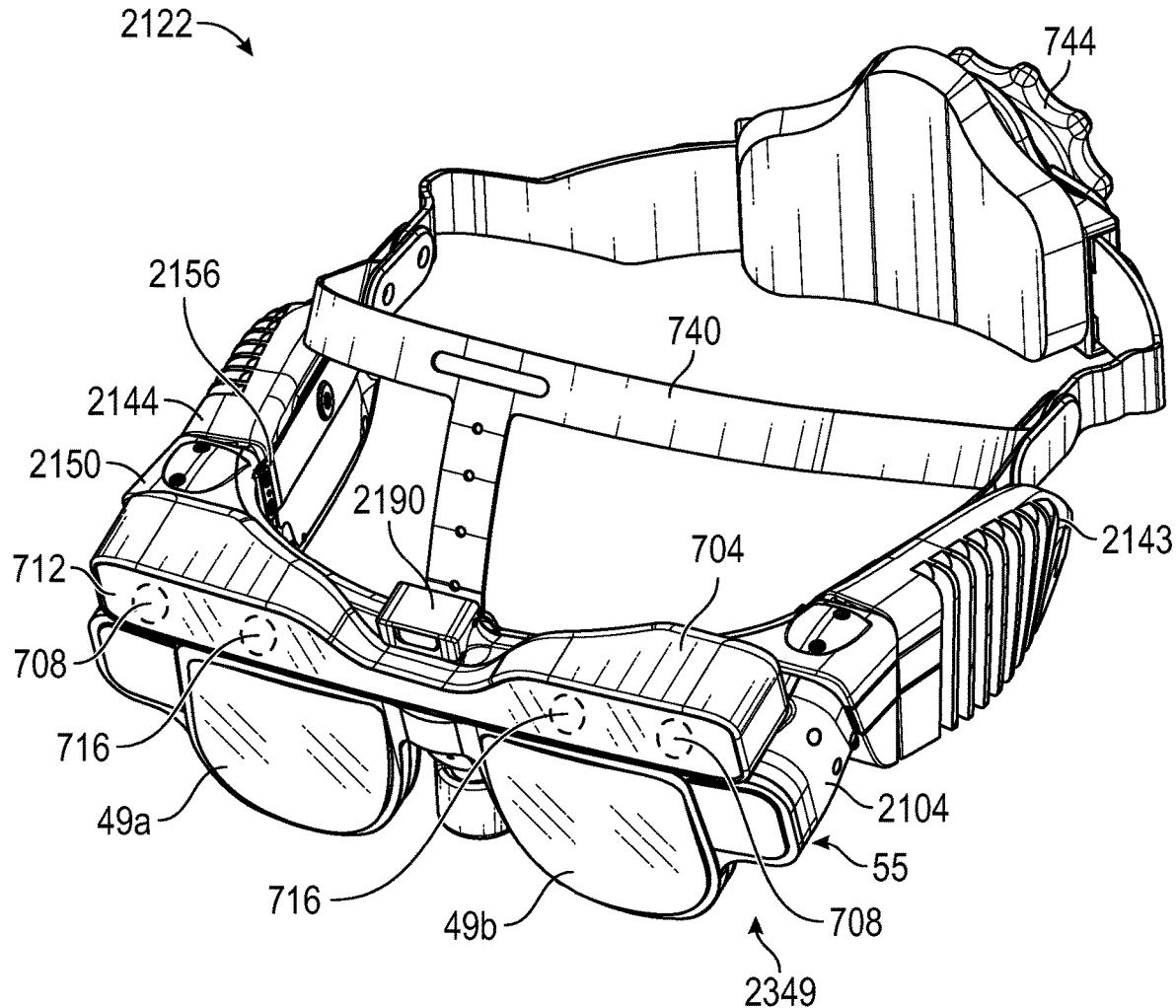
FIGS. 21A-21D illustrate another embodiment of a head-mounted display for use in the system of FIG. 1.

In the context of the present disclosure and in the claims, the terms "frame" and "head mounting assembly" are used interchangeably and may refer to the combination of two or more elements among housing 29, nose pad 28 and temple arms 43 and 44, including the combination of head strap 740 and knob 744 (that together form an adjustable strap assembly) of FIG. 2B or 21A or any other suitable assembly configured to hold HUD 700 or HMD 2122 at a selected position on the head of surgeon 26.

In some embodiments, a power cable (not shown) is threaded through a power cable strain relief 47 of HMD 22. In the present configuration, power cable strain relief 47 is mounted on right temple arm 44, and the power cable is configured to electrically connect between a power source (not shown) and several components of HMD 22, such as but not limited to an on/off button 39.

In some embodiments, the power source comprises a pack of suitable batteries, and one or more supercapacitors or ultracapacitors (not shown). In some embodiments, the pack of batteries comprises lithium-based batteries, such as but not limited to batteries produced by RRC Power Solutions GmbH (Hamburg, Germany).

In some embodiments, the supercapacitor or ultracapacitor can be used to reduce lengthy boot-up when changing the battery packs. Instead of powering down HMD 22, processor 33 may be configured to control the components of HMD 22 to enter a low current standby mode. By powering off all components and peripherals, current may be reduced to the minimum, so as to enable the supercapacitor or ultracapacitor to retain the state of HMD 22 for a sufficiently long time interval of switching the battery packs without the need for an additional battery for the standby mode.

This particular configuration of HMD 22 is shown by way of example, in order to illustrate certain problems that are addressed by embodiments of the disclosure and to demonstrate the application of these embodiments in enhancing the performance of such a system. Embodiments of the disclosure, however, are by no means limited to this specific sort of example system, and the principles described herein may similarly be applied to other sorts of HMDs used in suitable types of AR-based image-guided surgical systems. In addition, HMD 22 may be used in non-medical applications, including consumer and commercial applications.

In some embodiments, system 11 is not limited only to augmented reality systems and/or to systems comprising one or more HMDs. For example, the tracking of patient and/or tool may be performed using stationary tracking systems (other than HMD) and the display may also be on a stationary display, which may or may not be displayed as augmented reality and may or may not be mounted on the head of the user (e.g., surgeon 26) of system 11.

In some embodiments, HMD 22 may comprise various types of image sources, such as but not limited to OLED and liquid-crystal on silicon (shown and described in connection with FIG. 3 below). These image sources may be combined with various sorts of optics (or optical setups), such as but not limited to visor-based, waveguide-based and birdbath-based optical engines. For example, HMD 22 may comprise a combination of OLED and visor, or a combination of liquid-crystal on silicon and waveguide sources. However, it is noted that all possible permutations of the above image source and optics may be applicable for HMD 22.

In the example of FIG. 1, HMD 22 and components and assemblies thereof are implemented using the projection/visor based optical engine. In some embodiments, HMD 22 may be implemented using other techniques and configurations, such as a waveguide-based optical engine. Moreover, instead of glasses, HMD 22 may comprise a helmet-shaped headset also referred to herein as a head-up display (HUD), an example configuration of which is described in detail in connection with FIG. 2B below. In some embodiments, HMD 22 may include features of both the helmet-shaped headset of FIG. 2B and the version shown in FIG. 2A, for example as is shown in FIGS. 21A-21D, described below.

In some embodiments, an HMD 22 that includes all the parts described in FIGS. 1 and 2A above, and some of the additional parts (or variations thereof) described in connection with FIGS. 5-14 below, has a weight of about 200 grams or less, and has a suitable distribution of weight, in order to obtain high comfortability to surgeon 26 and eliminate fatigue associated with a large weight (e.g., between about 0.5 Kg and 1.5 Kg) of other sorts of head-mounted devices.

FIG. 2B is a schematic pictorial illustration of an exemplary head-up display (HUD) 700, in accordance with one embodiment. HUD 700 also serves and is referred to herein as an HMD, and may replace, for example, HMD 22 of FIG. 1 above.

In some embodiments, HUD 700 comprises an optics housing 704, which incorporates a camera 708. More specifically, camera 708 may comprise an RGB camera configured as an IR camera using a suitable filter and software or the camera 708 may comprise an infrared camera or an RGB-IR camera. In some embodiments, housing 704 comprises an infrared transparent window 712, and within the housing, e.g., behind the window, are mounted one or more infrared projectors 716.

In some embodiments, HUD 700 comprises a pair of AR displays 720 that are mounted on housing 704. In some embodiments, displays 720 may comprise, for example, an optical combiner, a waveguide, or a visor, as described in connection with FIGS. 1 and 2A above.

In some embodiments, AR displays 720 allow surgeon 26 to view entities, such as part or all of a selected field-of-view (not shown) through AR displays 720, and which are also configured to present to the surgeon images that may be received from processing system 31 or any other information.

In some embodiments, HUD 700 comprises a processor 724, which operates elements of HUD 700 and is mounted in a processor housing 726. Processor 724 typically communicates with processing system 31 via an antenna 728. In some embodiments, processor 724 may perform some of the functions performed by processing system 31. In some embodiments, processor 724 may completely replace processing system 31.

In some embodiments, HUD 700 comprises a flashlight 732, which is mounted on the front of HUD 700. Flashlight 732 is configured to direct a beam of visible spectrum light (e.g., wavelengths between about 350 nm and 800 nm or between about 300 nm and 900 nm) to selected objects, so that surgeon 26 or other wearer is able to clearly see the objects through displays 720.

In some embodiments, HUD 700 comprises a power source (e.g., a battery (not shown)), which is configured to supply power to several elements of HUD 700 via a battery cable input 736. The power source may additionally or alternatively include one or more capacitors, supercapacitors or ultracapacitors.

In some embodiments, HUD 700 is held and gripped in place on the head of surgeon 26 using a head strap 740, and comprises a knob 744 that the surgeon 26 may use to adjust the head strap of HUD 700. The head strap 740 and knob 744 may together be referred to as an adjustable strap assembly.

In some embodiments, HUD 700 may comprise additional components, such as but not limited to components described in FIGS. 1 and 2A above. For example, HUD 700 may comprise IMU 18, which is configured to produce position signals indicative of the position and orientation of a tracking system reference point/origin of HUD 700. Moreover, HUD 700 may comprise IR LED projectors, such as projectors 17 of HMD 22.

Additionally, or alternatively, flashlight 732 of HUD 700 may be coupled to housing 704 using a suitable detachable lighting fixture assembly (DLFA), which is configured to be attached to and detached from housing 704 and/or the upper bridge (not indicated by a numeral) of HUD 700, or any other suitable location of HUD 700. The ability to detach flashlight 732 reduces weight from HUD 700, and may also be performed in case lighting assembly 27 of FIG. 1 above directs sufficient light to perform the surgical procedure. Non-limiting examples of detachable lighting fixture assemblies are described in detail in connection with FIGS. 4-8 and 27A-28F below.

This particular configuration of HUD 700 is shown by way of example, in order to illustrate certain problems that are addressed by certain embodiments and to demonstrate the application of these embodiments in enhancing the performance of such a system. Embodiments of the disclosure, however, are by no means limited to this specific sort of example HMD, and the principles described herein may similarly be applied to other sorts of head-mounted displays, head-up displays used in suitable types of AR-based image-guided surgical systems. For example, additional features of a head-mount display or a head-up display are described in detail, for example, in U.S. Patent Application Publication 2017/0178375, which is incorporated herein by reference.

Figure 3:
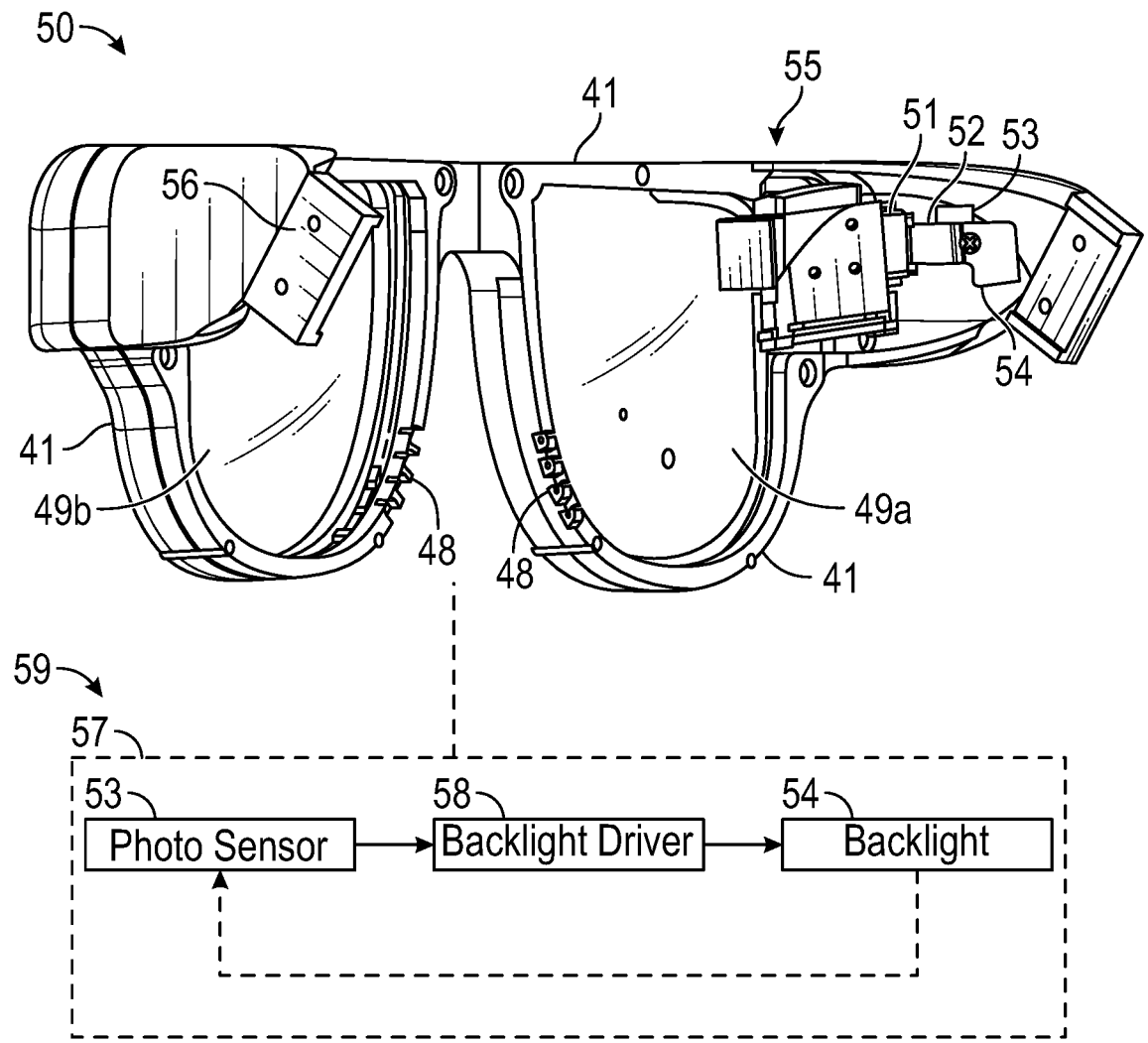
FIG. 3 is a schematic pictorial illustration of an HMD comprising a waveguide-based optical engine (OE) having a liquid crystal display (LCD) and a closed-loop control assembly for controlling light intensity in the OE.

FIG. 3 is a schematic pictorial illustration of an HMD 50 comprising a liquid-crystal based optical engine (OE) 55 and a closed-loop control assembly 59 configured to control the light intensity in OE 55, in accordance with an embodiment of the disclosure. HMD 50 may replace, for example, HMD 22 of FIG. 1 above.

In some embodiments, HMD 50 comprises a wave-guide based OE 55 comprising a backlight source 54. In some embodiments, backlight source 54 comprises one or more LEDs configured to supply visible light through a waveguide 52, which is coated with an opaque shroud to prevent, or at least reduce, the amount of stray light, which is an optical leakage of photons of the backlight. More specifically, backlight source 54 may comprise red, green and blue (RGB) LEDs and may be configured to emit a white light generated by combining the light of the RGB LEDs.

In some embodiments, the backlight is passing through an optical coding device (e.g., a liquid-crystal on silicon (LCOS) device 51), which is configured to modulate the backlight back on information coded by processor 33. For example, in response to receiving a signal indicative of a coded slice of a computerized tomography (CT) image, LCOS device 51 is configured to modulate the backlight and to produce an image of the CT slice presented over a display 49a of HMD 50.

In some embodiments, OE 55 comprises a photosensor 53, which is configured to measure stray light between backlight source 54 and LCOS 51 without interfering with the operation of OE 55. In other words, in some embodiments, photosensor 53 is not positioned along the optical axis of the backlight intended to be modulated, and uses the stray light for measuring the intensity of the backlight emitted from backlight source 54 into waveguide 52.

Reference is now made to an inset 57 showing a block diagram of closed-loop control assembly 59. In some embodiments, in response to sensing the intensity of the backlight emitted from backlight source 54, photosensor 53 is configured to produce a signal indicative of the measured intensity of the backlight.

In some embodiments, based on the signal received from photosensor 53, processor 33 is configured to control a backlight driver 58 to adjust the current applied to the RGB LEDs of backlight source 54.

In principle, it is possible to control the current supplied to backlight source, but due to the non-uniform response of the LEDs (even from the same batch of LEDs) of any light source (such as backlight source 54), the intensity of the backlight may be non-uniform and altered. More specifically, (i) the backlight may be altered over time in the same backlight source 54, e.g., when the LEDs are aging and/or in response to changes in the temperature of parts surrounding the LEDs, (ii) the backlight may be altered between different backlight sources 54 of different respective OEs 55 (e.g., between the left and right OEs 55 of HMD 50), (iii) between OEs of different HMDs 50, and (iv) any combination thereof.

In other words, processor 33, or any suitable dedicated circuit controls driver to adjust the current supplied to each of the LEDs of backlight source 54, so as to keep the light levels constant. Due to the fact that a sequential strobing scheme is used, a single photosensor 53 may be sufficient for controlling the light emitted in all three-color channels (RGB) in one embodiment.

Thus, in one embodiment, controlling the backlight based on direct off-axis measurement of the stray light of OE 55 improves the uniformity of the brightness of the AR image presented over AR display 49a.

Reference is now made back to the general view of FIG. 3. In some embodiments, HMD 50 comprises an additional AR display 49b, which is configured to present to the left eye of surgeon 26, an additional AR image by applying the same technique to a similar optical engine (not shown) mounted on a section 56 (e.g., a bracket) of the left temple arm (not shown) of HMD 50. This implementation may also be incorporated in the other HMDS and/or HUDs described herein.

In some embodiments, processor 33 is configured to present different AR images over AR displays 49a and 49b, so as to display to surgeon 26 images such as a stereoscopic image (e.g., of a 3D CT image) of the organ (or other target treatment anatomy or region) being operated on.

In some embodiments, HMD 50 comprises an adaptor 48, which is formed in a frame 41 of HMD 50 and is adapted for mounting on HMD 50, and a suitable type of nose pad, such as nose pad 28 shown in FIG. 2A above and described in more detail in connection with FIG. 12 below. Moreover, the temple arms of HMD 50 are extended from section 56 and may have a similar configuration to that of FIG. 2A above. Embodiments related to several configurations of the temple arms of the HMDs and HUD of the present disclosure are described in detail in connection with FIGS. 9-11 below.

This particular configuration of HMD 50 is shown by way of example, in order to illustrate certain problems that are addressed by certain embodiments and to demonstrate the application of these embodiments in enhancing the performance of such a system. Embodiments of the disclosure, however, are by no means limited to this specific sort of example HMD configuration, and the principles described herein may similarly be applied to other sorts of HMDs and HUDs used in any suitable types of near-eye display AR-based image-guided surgical systems. In addition, HMD 50 may be used with other medical systems or with non-medical systems, including for consumer or commercial applications.

Example Headlight Assemblies

Figure 4:
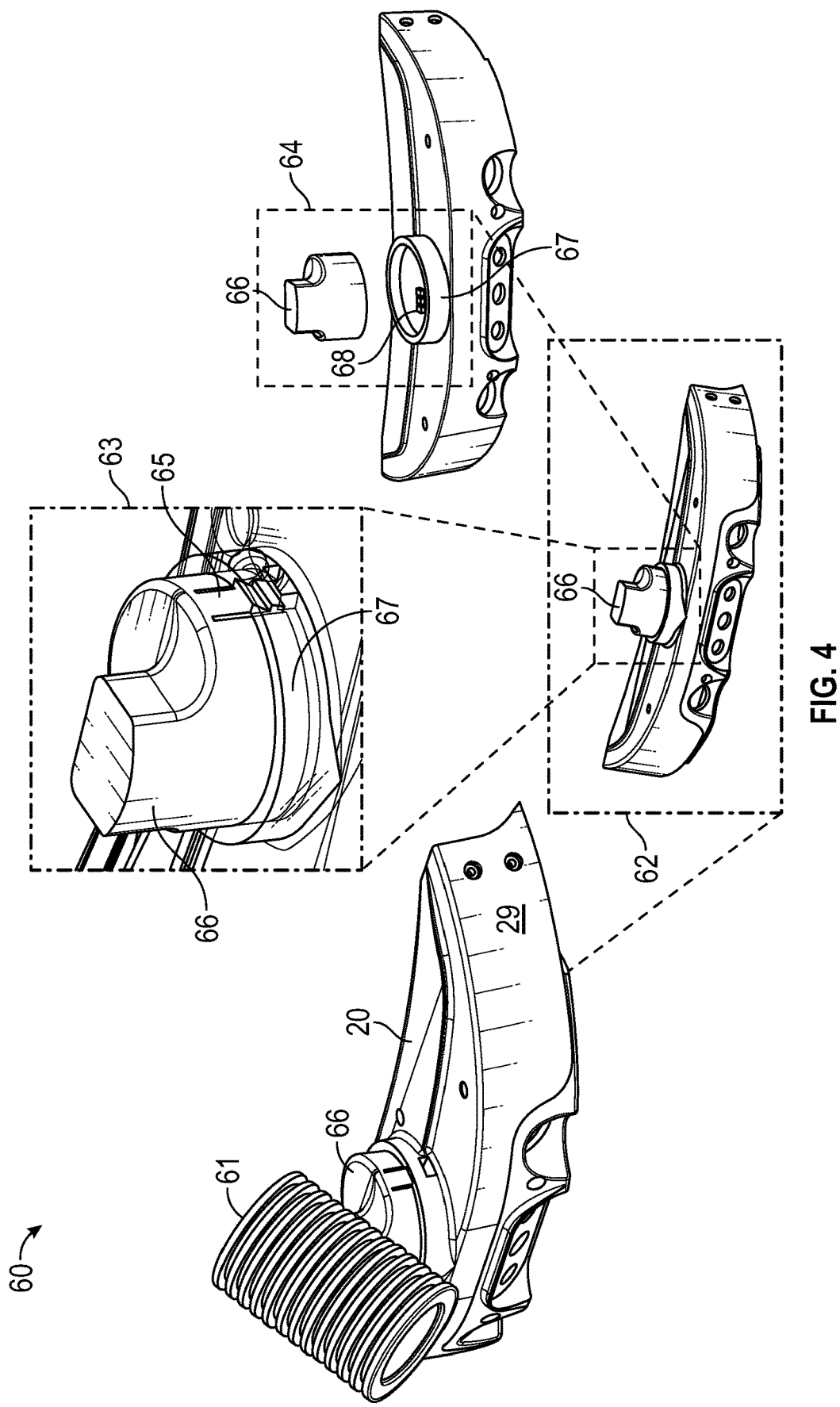
FIGS. 4-8 are schematic pictorial illustrations of headlight assemblies (HAs) for use in any of the HMDs shown in FIGS. 1, 2A, 2B, 3, 21A-29E, and 31A-32.

FIG. 4 is a schematic pictorial illustration of a headlight assembly (HA) 60 for use in any of the HMDs and HUD shown in FIGS. 1, 2A, 2B, 3, 21A-29E, and 31A-32, in accordance with various embodiments.

In some embodiments, HA 60 comprises a flashlight 61, which may have similar features of flashlight 732 of FIG. 2B above, or of any other flashlight disclosed herein.

In some embodiments, HA 60 comprises a detachable lighting fixture assembly (DLFA) 66, which is adapted for attaching flashlight 61 to surface 20 of housing 29, and for detaching flashlight 61 from surface 20.

Reference is now made to insets 62, 63, and 64. Inset 62 shows DLFA 66 without flashlight 61. In some embodiments (such as shown in inset 63), DLFA 66 comprises one or more clips 65 (e.g., one clip, two clips, three clips or more than three clips), which are configured to: (i) attach DLFA 66 to a base 67 located on surface 20, when DLFA 66 (and flashlight 61) are moved toward surface 20, and (ii) detach DLFA 66 from base 67 when clip(s) 65 are pressed toward the inner volume of DLFA 66.

In some embodiments (such as shown in inset 64), base 67 comprises electrical connections 68 (e.g., two or more vertical pogo pins, three pogo pins, or more than three pogo pins) configured to conduct electrical power and/or signals or data between housing 29 and flashlight 61.

Figure 5:
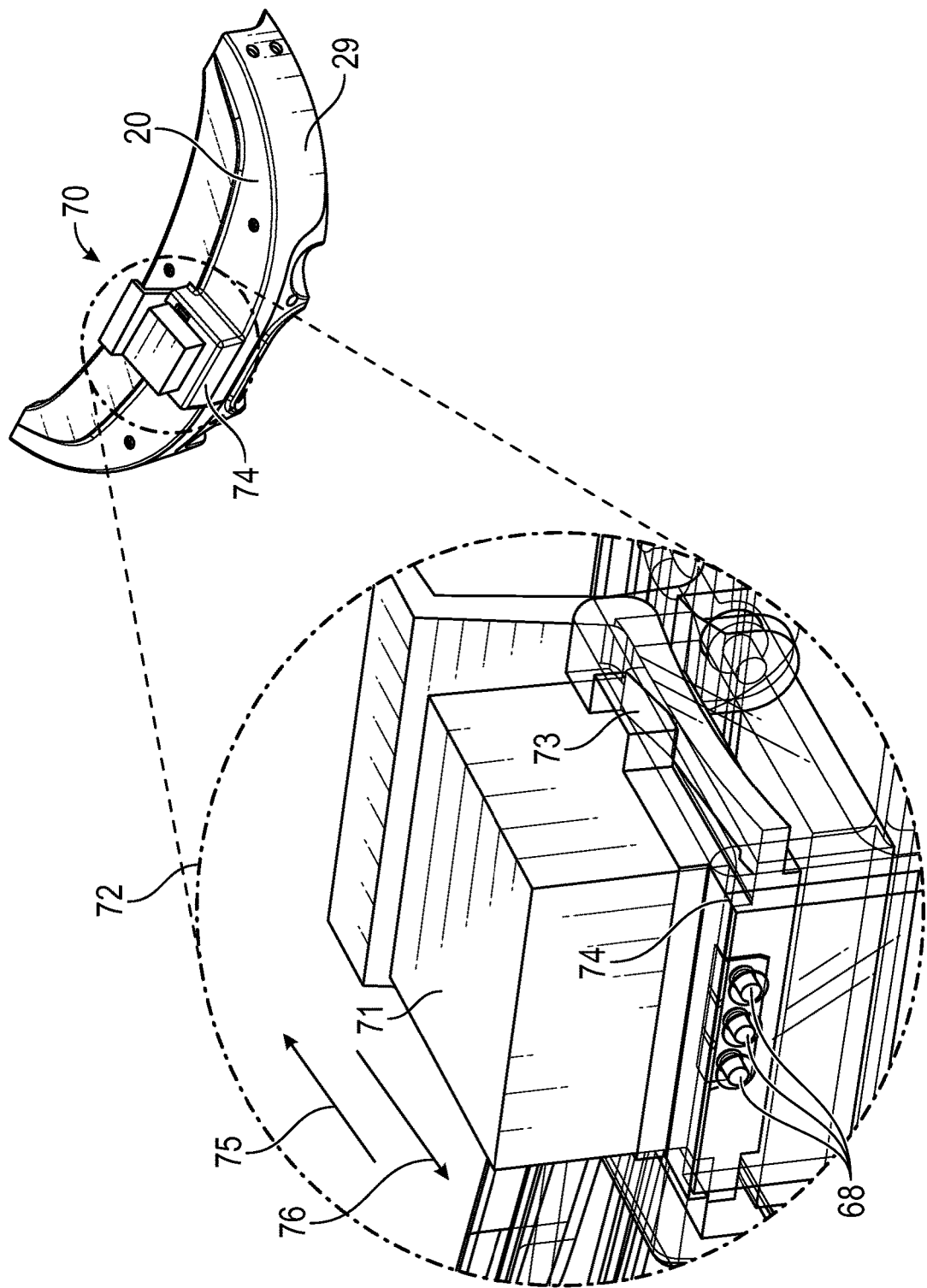

FIG. 5 is a schematic pictorial illustration of a headlight assembly (HA) 70 for use in any of the HMDs and HUD shown in FIGS. 1, 2A, 2B, 3, 21A-29E, and 31A-32, in accordance with several embodiments.

In some embodiments, HA 70 comprises a flashlight (not shown), which may have similar features of flashlight 61 of FIG. 4 above and/or flashlight 732 of FIG. 2B above, and/or of any other flashlight disclosed herein.

Reference is now made to an inset 72. In some embodiments, HA 70 comprises a DLFA 71, which is adapted for attaching the flashlight to surface 20 of housing 29, and for detaching the flashlight away from surface 20.

In some embodiments, DLFA 71 comprises one or more clips 73 (for example, one clip, two clips, three clips or more than three clips), which are configured to: (i) attach DLFA 71 to a base 74 located on surface 20, when DLFA 71 is moved in a direction 76 (e.g., away from the forehead of surgeon 26), and (ii) detach DLFA 71 from base 74 when clip(s) 73 are pressed toward base 74, and at the same time, DLFA 71 is moved in a direction 75 (e.g., toward the forehead of surgeon 26).

In some embodiments, base 74 comprises electrical connections 68 (e.g., two or more horizontal pogo pins, three pogo pins, or more than three pogo pins) configured to conduct electrical power and/or signals or data between housing 29 and the flashlight described above.

Figure 6:
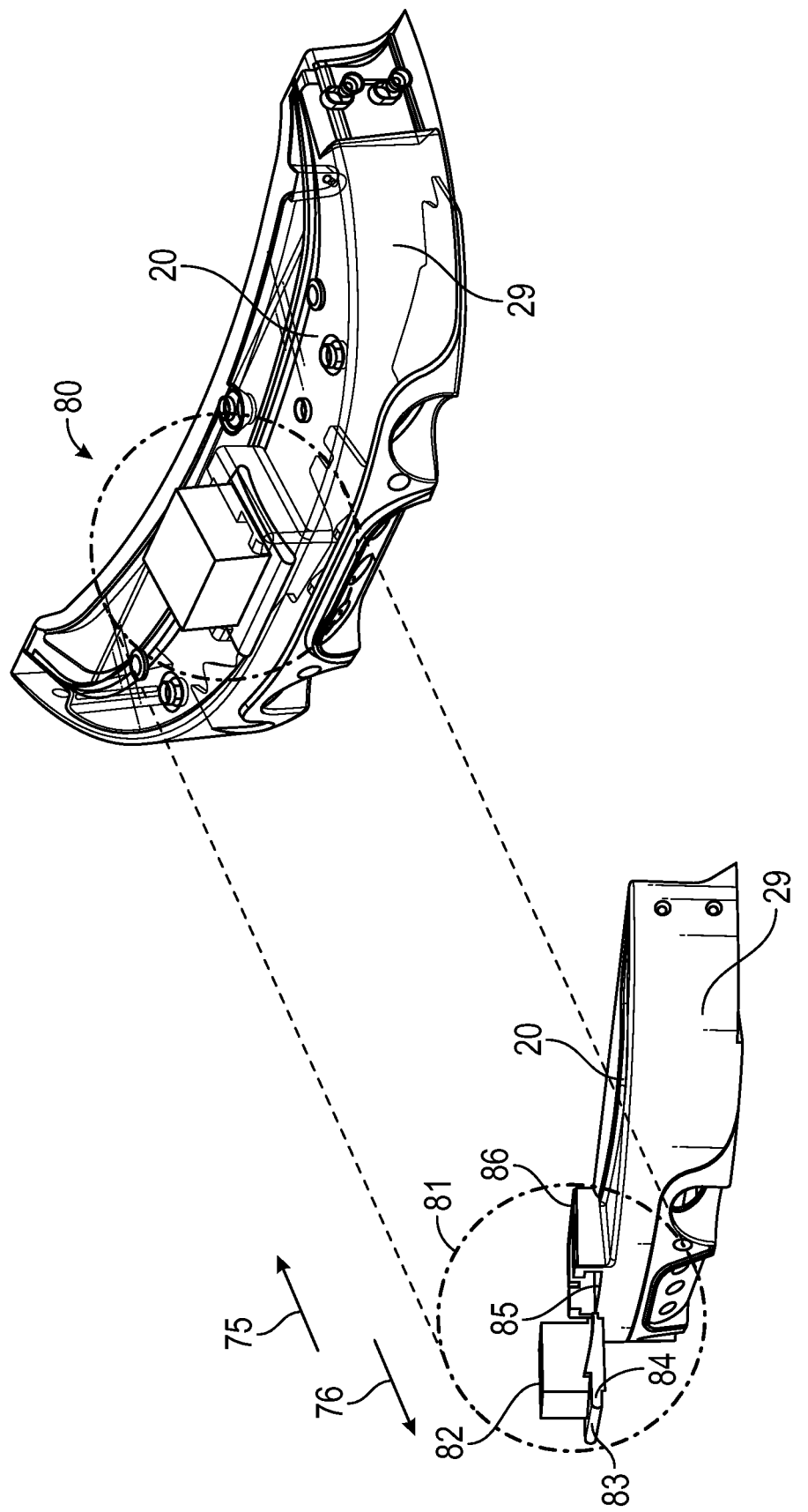

FIG. 6 is a schematic pictorial illustration of a headlight assembly (HA) 80 for use in any of the HMDs and HUD shown in FIGS. 1, 2A, 2B, 3, 21A-29E, and 31A-32, in accordance with various embodiments.

In some embodiments, HA 80 comprises a flashlight (not shown), which may have similar features of flashlights 61 of FIG. 4 above and flashlight 732 of FIG. 2B above, and/or of any other flashlight disclosed herein.

Reference is now made to an inset 81. In some embodiments, HA 80 comprises a DLFA 82, which is adapted for attaching the flashlight to surface 20 of housing 29, and for detaching the flashlight away from surface 20.

In some embodiments, a base 86 formed on surface 20 comprises trenches 85 configured to receive DLFA 82 as will be described herein.

In some embodiments, DLFA 82 comprises two leads 84 (one at each side of DLFA 82), which are configured to: (i) slide through trenches 85 along direction 75 for attaching DLFA 82 to base 86, and (ii) slide through trenches 85 along direction 76 for detaching DLFA 82 away from base 86.

In some embodiments, DLFA 82 comprises a handle 83 for moving DLFA 82 in directions 75 and 76, and one or more clips configured to attach and detach DLFA 82 in conjunction with the movement in directions 75 and 76.

In some embodiments, housing 29 comprises electrical connections (e.g., one or more vertical or horizontal pogo pins (not shown)) configured to conduct electrical power and/or communication signals or data between housing 29 and the flashlight described above, which is connected to DLFA 82.

Figure 7:
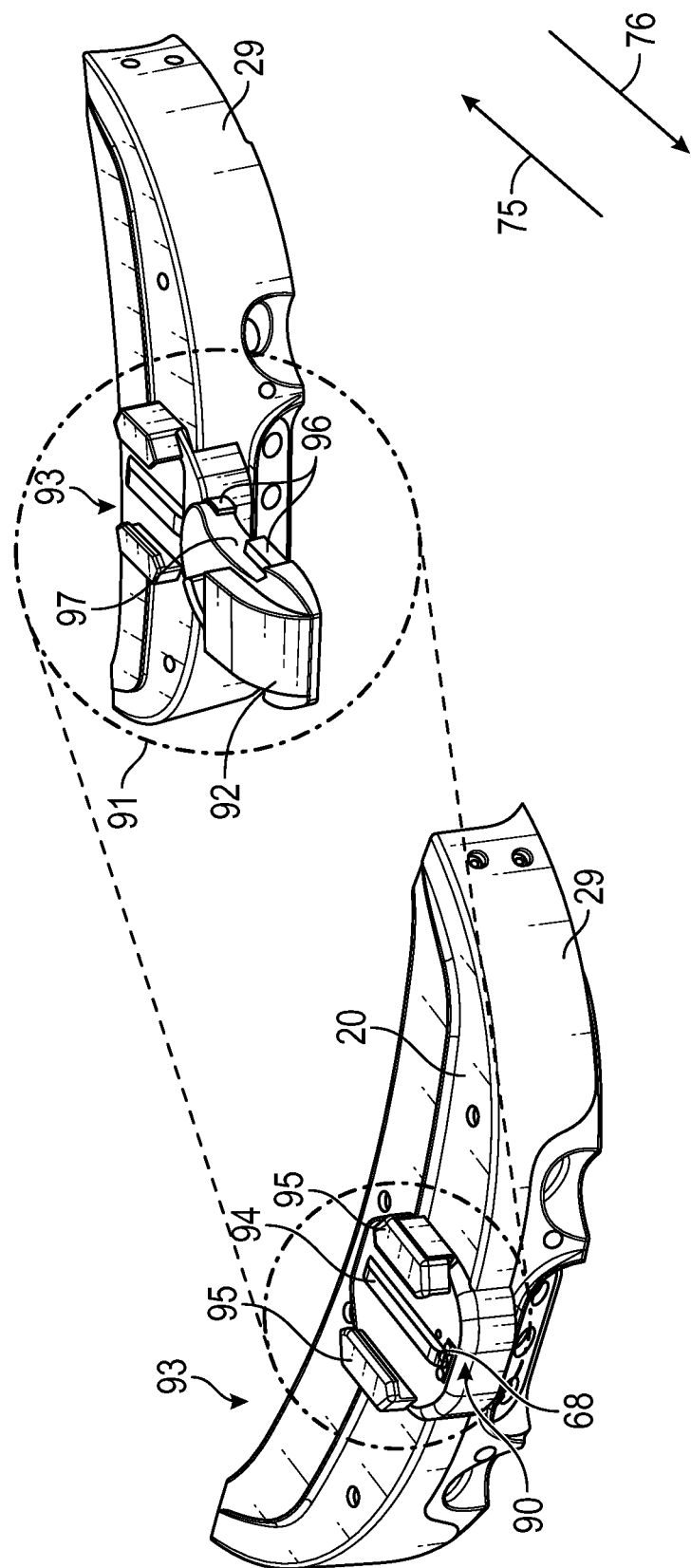

FIG. 7 is a schematic pictorial illustration of a headlight assembly (HA) 90 for use in any of the HMDs and HUD shown in FIGS. 1, 2A, 2B, 3, 21A-29E, and 31A-32, in accordance with various embodiments.

In some embodiments, HA 90 comprises a flashlight (not shown), which may have similar features of flashlights 61 of FIG. 4 above, flashlight 732 of FIG. 2B above, and/or of any other flashlight disclosed herein.

Reference is now made to an inset 91. In some embodiments, HA 90 comprises a DLFA 92, which is adapted for attaching the flashlight to a base 93 coupled to surface 20 of housing 29, and for detaching the flashlight away from base 93.

In some embodiments, inset 91 shows how DLFA 92 is attached to and detached from base 93, when being moved in directions 75 and 76, respectively.

Reference is now made back to the general view of FIG. 7. In some embodiments, base 93 comprises a lead 94 configured to slide along a trench (not shown) formed at the lower surface of DLFA 92, which is facing base 93. Base 93 further comprises two fences 95 at the sides of the base.

In some embodiments, base 93 comprises electrical connections (e.g., two or more vertical and/or horizontal pogo pins (not shown)) configured to conduct electrical power and/or communication signals or data between housing 29 and the flashlight described above, which is connected to DLFA 92.

Reference is now made back to inset 91. In some embodiments, DLFA 92 comprises two pairs of flexible fins 96 (one pair at each side of DLFA 92), which are partially surrounding an opening 97 configured to contain fences 95 for attaching DLFA 92 to base 93.

In some embodiments, the configuration of at least part of DLFA 92 and base 93 is similar to a design of a GoPro®-style mount of cameras and other electronic accessories, which is produced by GoPro Corporate (3025 Clearview Way, San Mateo, CA).

Figure 8:
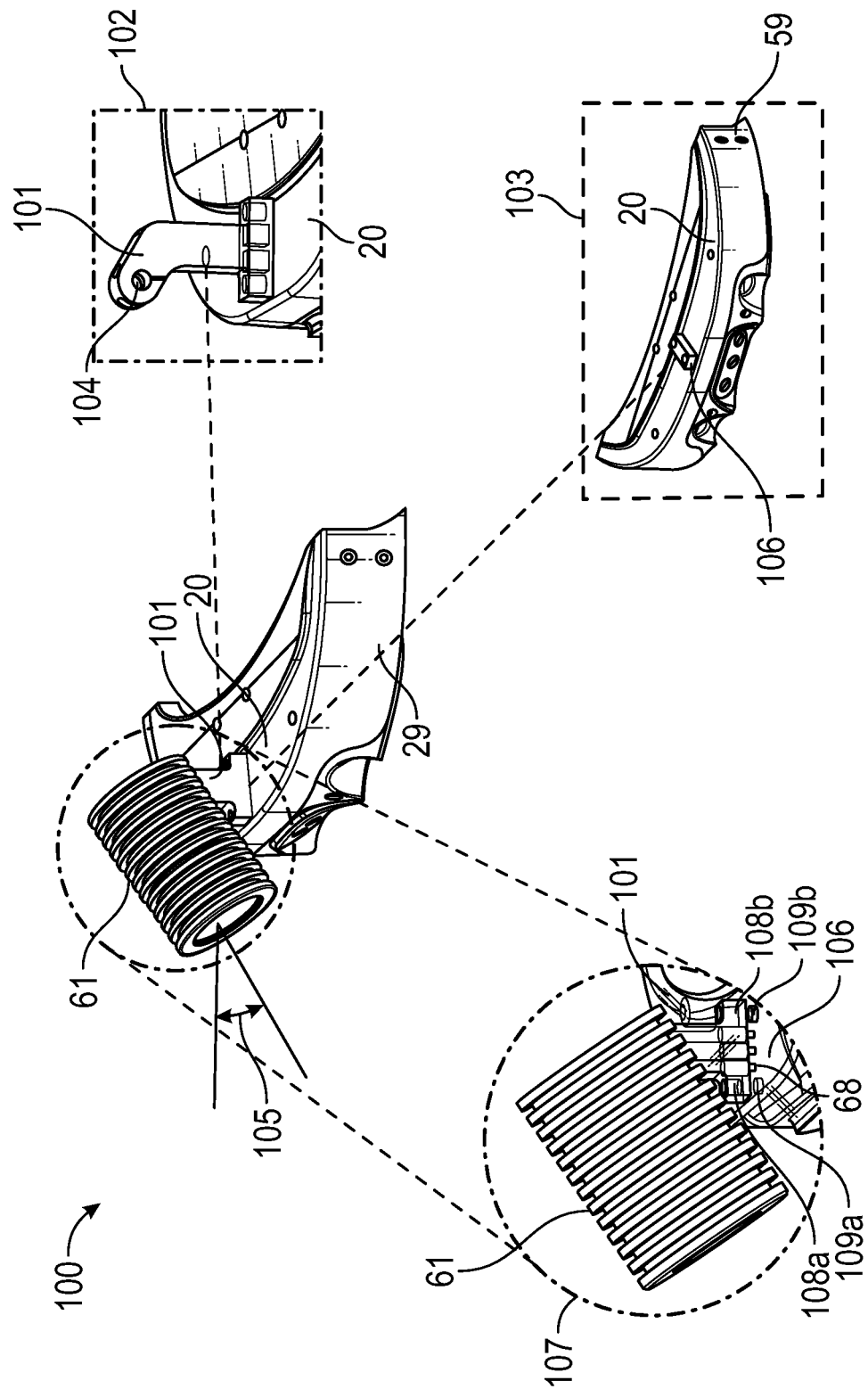

FIG. 8 is a schematic pictorial illustration of a headlight assembly (HA) 100 for use in any of the HMDs and HUD shown in FIGS. 1, 2A, 2B, 3, 21A-29E, and 31A-32, in accordance with various embodiments.

In some embodiments, HA 100 comprises a flashlight 61 and a detachable lighting fixture assembly (DLFA) 101, which is adapted for attaching flashlight 61 to surface 20 of housing 29, and for detaching flashlight 61 away from surface 20.

Reference is now made to insets 102 and 103. In some embodiments, DLFA 101 comprises a bore 104, which is adapted to contain an axis (not shown) for controlling an elevation angle 105 of flashlight 61 relative to a virtual plane, e.g., parallel to surface 20 or to any other suitable reference plane.

With reference to inset 103, in some embodiments, DLFA 101 comprises a base 106, which is coupled to surface 20 and is configured to connect between DLFA 101 and surface 20 of housing 29.

Reference is now made to an inset 107. In some embodiments, base 106 comprises electrical connections 68 (e.g., two or more vertical or horizontal pogo pins) configured to conduct electrical power and/or signals or data between housing 29 and flashlight 61.

In some embodiments, base 106 comprises a pair of magnets 109a and 109b, and DLFA 101 comprises a pair of magnets 108a and 108b. When DLFA 101 is placed over base 106, magnets 108a and 109a attract one another, and similarly, magnets 108b and 109b attract one another.

In such embodiments, the magnetic-based attachment and detachment between DLFA 101 and base 106 are quick and easy because they do not demand a mechanical release of clips or any other sort of capturing and/or locking device. Thus, surgeon 26 or a medical staff member in the operating room can attach and detach DLFA 101 and flashlight 61 using one hand, and subsequently, adjust angle 105 for directing the light beam to a region of interest, e.g., the organ (or other target treatment anatomy or region) being operated on.

In some embodiments, DLFA 101 and base 106 may comprise three, four, or more than four pairs of magnets 108 and 109 for improving the stability of the magnetic-based coupling and preventing undesired rotation of DLFA 101 relative to base 106. In accordance with several embodiments, the size, shape, and magnetism level of magnets 108 and 109, and the distance between every pair of magnets 108 and 109, may define the stability of the magnetic-based coupling.

In some embodiments, a single pair of magnets 108 and 109 may be sufficient for enabling the stability of the magnetic-based coupling and preventing undesired rotation of DLFA 101 relative to base 106.

These particular configurations of the HAs and DLFAs of FIGS. 4-8 discussed above (and of FIGS. 27A-27D and 28A-28F discussed below) are shown by way of example, in order to illustrate certain problems that are addressed by various embodiments and to demonstrate the application of these embodiments in enhancing the illumination performance of such a HMD and/or HUD. Embodiments of the disclosure, however, are by no means limited to this specific sort of example configurations, and the principles described herein may similarly be applied to other sorts of headlight assemblies integrated with any suitable types of HMDs and/or HUDs used in near-eye display AR-based image-guided surgical procedures.

In some embodiments, the headlight assemblies shown in FIGS. 4-8 discussed above (and shown in FIGS. 27A-27D and 28A-28F discussed below) may be removed from the configuration of the HMDs and/or HUDs in case lighting assembly 27 of FIG. 1 above directs sufficient light to perform the surgical procedure.

Example Tilting Assemblies

The embodiments related to tilting assemblies that are described in detail in connection with FIGS. 9, 10A, 10B, 11, 12, 13, 14, 15A, 15B, 15C, and 23B below may be implemented, mutatis mutandis, in any of the HMDs and HUD shown in FIGS. 1, 2A, 2B, 3, 21A-29E, and 31A-32, and the techniques described in connection with FIGS. 9-15C and 23B are also applicable to any other suitable configurations of AR-based glasses and/or helmets, and to other sorts of AR-based near-eye head-mounted display assemblies, whether for medical or non-medical applications.

Figure 9:
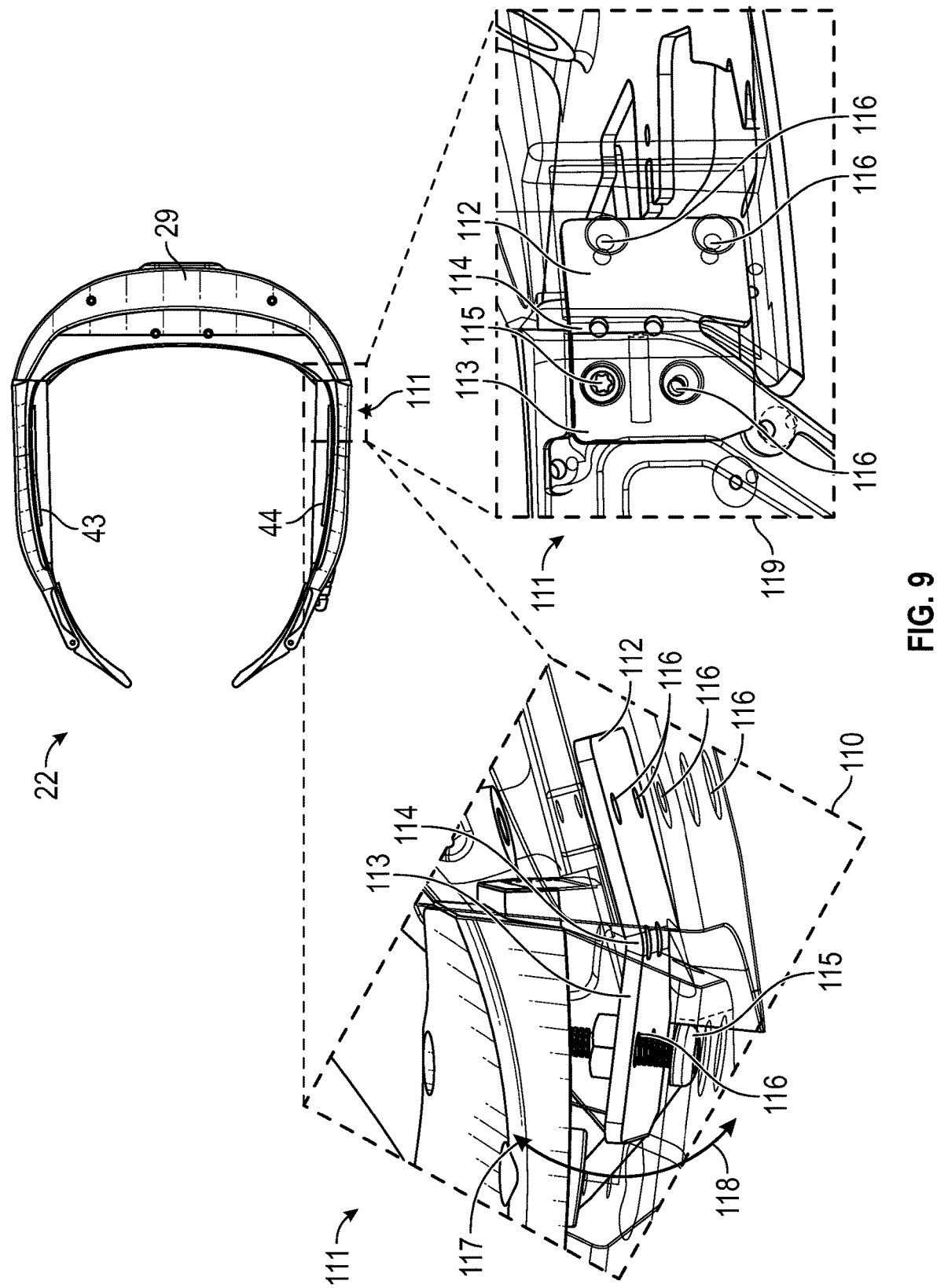
FIG. 9 is a schematic pictorial illustration of a tilting assembly of a self-adjustable temple arm for use in any of the HMDs shown in FIGS. 1, 2A, 2B, 3, 21A-29E, and 31A-32.
Figure 10:
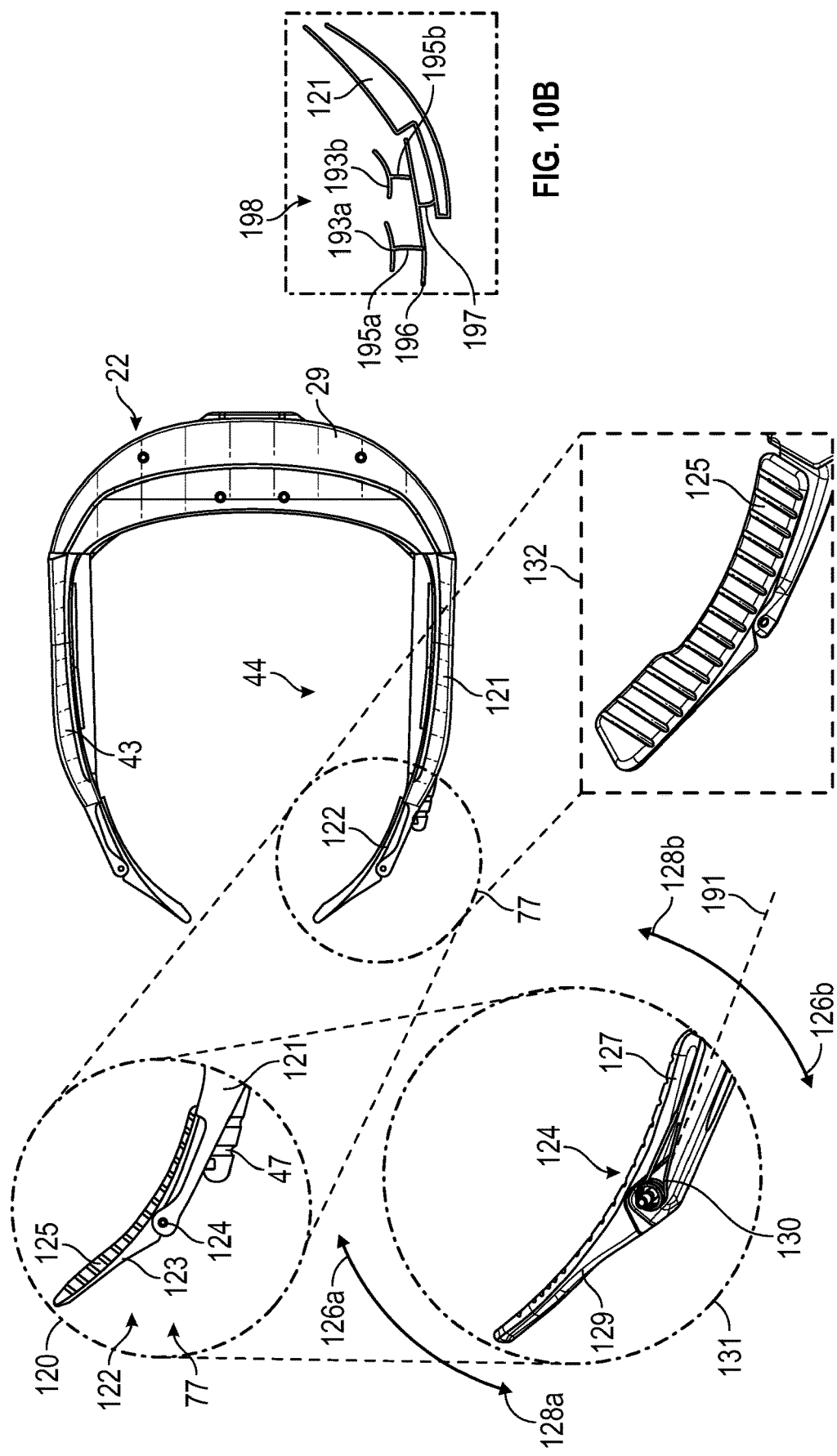
FIGS. 10A and 10B are schematic pictorial illustrations of additional multiple Degrees Of Freedom (DOF) implementations implemented in one or more tilting assemblies comprising self-adjustable and ergonomic temple arms and rocker arms for use in any sort of the HMDs shown in FIGS. 1, 2A, 2B, 3, and 29A.

FIG. 9 is a schematic pictorial illustration of a tilting assembly 111 (e.g., a temple tilting assembly), in accordance with an embodiment of the disclosure.

In some embodiments, tilting assembly 111 is configured for tilting temple arm 44 relative to housing 29. In other words, tilting assembly 111 provides surgeon 26 with a horizontal degree-of-freedom (DOF) for adjusting HMD 22 to the shape of the head of surgeon 26 or to the shape of the head of any other user of HMD 22. The surgeon 26 could be substituted with a consumer for non-medical applications.

In some embodiments, tilting assembly 111 may be implemented using a hinge (not shown), also referred to herein as an axis. In some embodiments, tilting assembly 111 is implemented in a virtual hinge, also referred to herein as a virtual axis. The terms "virtual hinge" and "virtual axis" and grammatical variations thereof refer to tilting one object relative to another object without using a real, or physical, hinge or a real, or physical, axis.

Reference is now made to an inset 110, which is a top view of tilting assembly 111 integrated in HMD 22.

In the example of FIG. 9, the virtual axis of tilting assembly 111 comprises three sections of a strap made from stainless steel or from any other suitable material. More specifically, tilting assembly 111 comprises a section 112 coupled to housing 29, a section 113 coupled to temple arm 44, and a section 114 configured to bend in response to the movement of temple arm 44 in directions 117 or 118. For example, in case a first surgeon has a smaller head than a second surgeon, tilting assembly 111 enables movement of temple arm 44 and section 113: (i) in direction 117 when the first surgeon wears HMD 22, and (ii) in direction 118 when the second surgeon wears HMD 22.

In the example implementation of the virtual axis of tilting assembly 111, sections 112 and 113 are coupled to housing 29 and temple arm 44, respectively, using screws 115 and bores 116. Section 112 and housing 29 move together as a rigid entity, and section 113 is moved in directions 117 and 118 by bending section 114.

In some embodiments, instead of using screws and bores, at least one of sections 112 and 113 tilting assembly 111 may be coupled to the respective parts of HMD 22 using any other coupling technique, such as but not limited to fastening with devices other than screws, gluing, welding, and/or soldering.

Additionally, or alternatively, at least one of sections 112 and 113 of tilting assembly 111 may be formed as an integral part of HMD 22. For example, section 112 may be formed in one cast mold together with at least part of housing 29.

In some embodiments, tilting assembly 111 may comprise different materials used in at least two of the sections. For example, sections 112 and 113 are made of stainless steel, and section 114 is made of a softer and more flexible material, such as but not limited to a nickel titanium alloy, also known as nitinol, and any other suitable material with proper characteristics, flexibility within the elastic range at the required movement range.

Reference is now made to an inset 119, which is a side view of tilting assembly 111 integrated in HMD 22. In the example of inset 119, the coupling of sections 112 and 113 to the respective parts of HMD 22 is shown using screw 115 and bores 116 (through which additional screws 115 are intended to be inserted in some embodiments).

In some embodiments, the techniques described for tilting assembly 111 are implemented, mutatis mutandis, also between temple arm 43 and housing 29.

In some embodiments, any other suitable type of tilting assembly may be implemented between temple arm 43 and housing 29.

FIG. 10A is a schematic pictorial illustration of a tilting assembly 77, in accordance with an embodiment.

In some embodiments, tilting assembly 77 is implemented in HMD 22, but may also be implemented in other sorts of HMDs.

In some embodiments, temple arm 44 comprises a section 121 configured to conform with the shape of the right temple of surgeon 26 or any other user of HMD 22. Temple arm 44 further comprises a section 122 configured to conform with the shape of the right side of the temple and/or the rear portion of human head, referred to herein as the nape of surgeon 26 or any other user of HMD 22.

Reference is now made to an inset 120, which is a side view of section 122 and tilting assembly 77 implemented in temple arm 44 for obtaining an additional adjustment DOF between HMD 22 and the head of surgeon 26 or any other user of HMD 22.

In some embodiments, tilting assembly 77 comprises a rotatable rocker arm 123, a hinge 124 connecting between section 121 and rocker arm 123, and a cushion 125 formed on the surface of rocker arm 123.

Reference is now made to an inset 131, which is a pictorial illustration of the inner structure of tilting assembly 77.

In some embodiments, rocker arm 123 (which may be made from polymer, such as but not limited to polycarbonate and/or Polyoxymethylene (POM) and/or any other suitable material) has a proximal section 127 and a distal section 129 configured to rotate about hinge 124, and a spring 130 (e.g., a torsion spring).

In some embodiments, rocker arm 123 is configured to rotate about hinge 124 relative to a longitudinal axis 191 of section 121.

For example, when HMD 22 is mounted on the head of the aforementioned first surgeon, section 129 is moving from its stationary state, all the way in direction 128a, and follows the ergonomic structure of the user head, usually slightly to direction 126a and section 127 is moved in a direction 126b to conform with the shape of the nape of the first surgeon.

Similarly, when HMD 22 is mounted on the head of the second surgeon (having a different shape of head compared to that of the first surgeon), section 129 is moved in a direction 126a and section 127 is moved in a direction 126b to conform with the shape of the rear head portion, also referred to herein as the nape of the second surgeon. Torsion spring 130 may be configured to reverse the movement direction. In the illustrated example, torsion spring 130 moves section 127 in direction 128b for improving the clamping between rocker arm 123 and the head of the user (e.g., the second surgeon). Moreover, torsion spring 130 is configured to move section 127 in order to enable smooth insertion of HMD 22 on the head of the respective surgeon.

In some embodiments, section 121 has an opening or a partial opening for containing section 127 when being rotated in direction 126b.

Reference is now made to FIG. 10B, showing an alternative configuration to rocker arm shown in insets 120 and 131. In the example of FIG. 10B, HMD 22 may comprise an array 198 of rocker arms 193 (e.g., two rocker arms 193a and 193b). At least one of rocker arms 193 may be similar to rocker arm 123 (and may be adapted to fit into array 198), or may comprise any other suitable design of a rocker arm adapted to be incorporated in array 198.

In the example of FIG. 10B, the assembly of array 198 comprises a bar 196 also referred to herein as a common bar, which is configured to rotate about a hinge 197 coupling between section 121 and bar 196. Moreover, both rocker arms 193a and 193b are coupled to hinges 193a and 193b, respectively, which are coupled to bar 196. In an embodiment, the configuration of hinges 197, 193a and 193b may be similar to that of hinge 124 shown in insets 120 and 131 of FIG. 10A. In another embodiment, at least one of hinges 197, 193a and 193b may have a configuration other than that of hinge 124.

Reference is now made to an inset 132 of FIG. 10A, showing cushion 125 of HMD 22.

In some embodiments, cushion 125 is disposed over the entire surface of rocker arm 123 that is facing the head of the surgeon.

In some embodiments, cushion 125 may be molded on rocker arm 123, or may comprise a separate part attached to rocker arm 123. Cushion 125 may comprise a large variety of materials, solid or sponged (for example, silicone, neoprene, polyurethane, and/or other suitable materials).

In some embodiments, the sponge may comprise closed cells that do not absorb fluids (e.g., sweat), or open cells adapted to absorb fluids.

In some embodiments, cushion 125 comprises a viscoelastic foam also referred to as a "memory foam" for obtaining a soft cushion.

In some embodiments, when a weighted object is positioned on the viscoelastic foam, the foam progressively conforms to the shape of the object, and after the weight (i.e., force) is removed, the foam slowly reassumes its original shape.

In some embodiments, when using viscoelastic material in cushion 125, a human body temperature between about 36° C. and 37° C. accelerates the properties of the memory foam described above.

In accordance with several embodiments, the soft cushion and the viscoelastic foam are adapted to generate a uniform distribution of pressure applied to the head of the surgeon using HMD 22, and thereby, enabling both effective clamping between rocker arm 123 and the head, while retaining a feeling of comfortability for the user (e.g., surgeon 26). Moreover, the clamping effect can be beneficial for safety reasons, in order to preclude a falling event of HMD 22 from the head during the surgical operation.

In some embodiments, HMD 22 comprises two or more DOFs obtained by tilting assemblies 111 and 77, and by using the two-section shape of rocker arm 123 and the selected materials of cushion 125. In accordance with several embodiments, increasing the number of DOFs improves the gripping and adjustments between the frame of HMD 22 (e.g., temple arms 43 and 44, and housing 29) and the contour and/or curvature of the head of the surgeon performing the surgical operation.

In some embodiments, the outer surface of cushion 125 has a suitable texture for improving the gripping to the nape of the head of surgeon 26. For example, the outer surface of cushion 125 (intended to be placed in contact with the nape) may comprise grooves shown in the example of inset 132.

Figure 11:
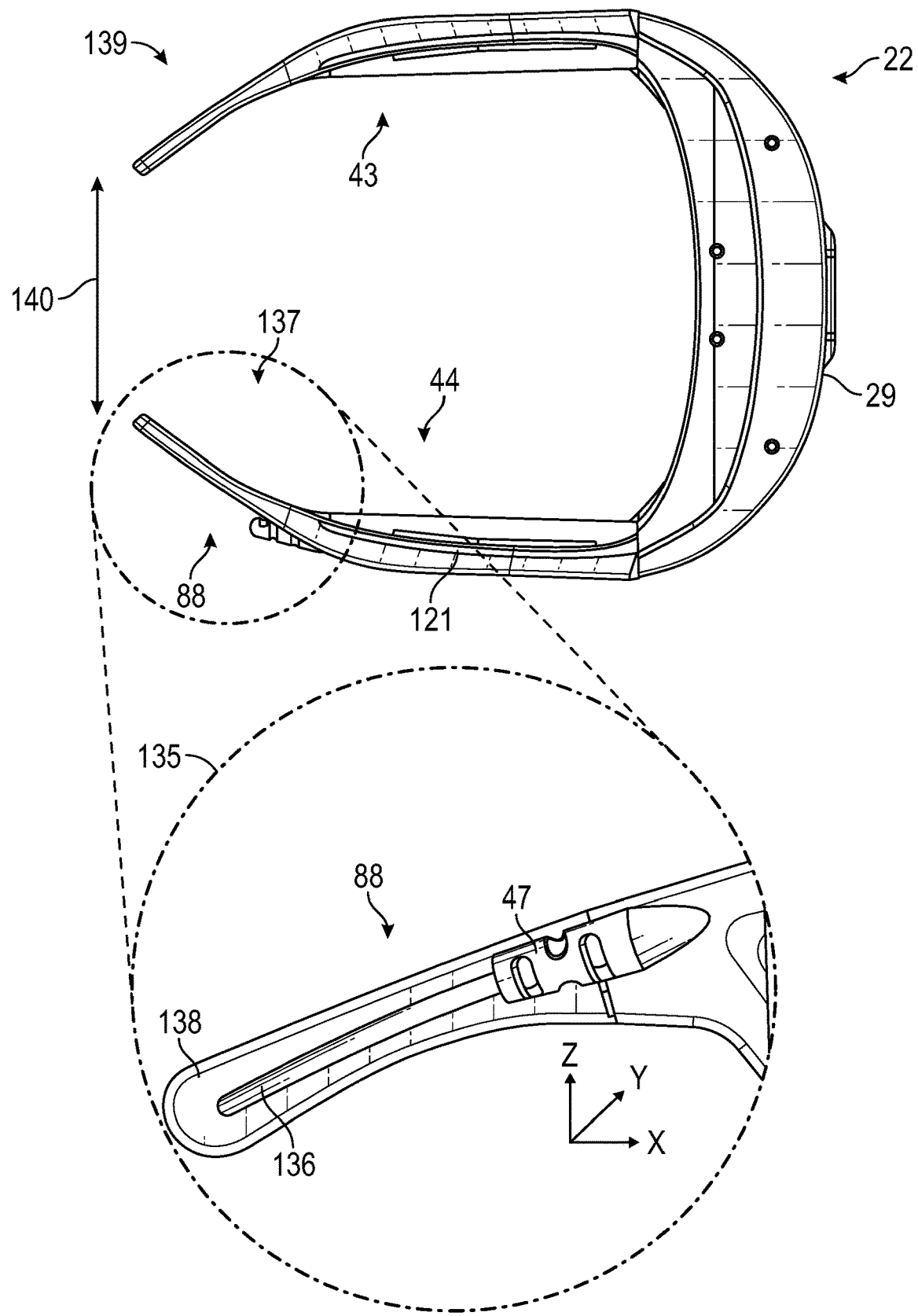
FIG. 11 is a schematic pictorial illustration of another implementation of a multiple DOFs implementation implemented in one or more respective tilting assemblies of a self-adjustable and ergonomic temple arm for use in any of the HMDs shown in FIGS. 1, 2A, 2B, 3, and 29A.

FIG. 11 is a schematic pictorial illustration of a tilting assembly 88, in accordance with one embodiment.

In some embodiments, tilting assembly 88 is implemented in HMD 22, but may also be implemented in other sorts of HMDs, such as the other HMDs described herein. Moreover, tilting assembly 88 may be used instead of tilting assembly 77 of FIG. 10A above, and due to the different configuration, the respective section has a numeral 137 instead of a numeral 122 of the corresponding section shown in FIG. 10A above.

Reference is now made to an inset 135 showing a side view of tilting assembly 88 in an XYZ coordinate system.

In some embodiments, tilting assembly 88 comprises a skeleton 136, which may be made from a suitable metal (e.g. Aluminum 5052 H32, supplied by Aleris International Inc. (Beachwood, OH) or other aluminum or metallic or metallic alloy or polymeric or elastomeric material) adapted to be shaped at least along an XY plane of the XYZ coordinate system. In some embodiments, skeleton 136 may also be shaped along the Z-axis to some extent (even though, in some implementations, this shape adjustment is not required).

In some embodiments, tilting assembly 88 comprises an upholstery 138, which is fitted over and may be coupled with skeleton 136. In some embodiments, upholstery 138 comprises an over molding cushion having similar properties and materials (e.g., viscoelastic foam) to that of cushion 125 of FIG. 10A above. In some implementations, a section 139 of temple arm 43 comprises a structure similar to that of the skeleton and upholstery of section 137, mutatis mutandis.

In some embodiments, the metal of skeleton 136 is adapted to transform from an elastic deformation (in which the skeleton returns to its original shape in response to applying a force and performing a small deformation) to a plastic deformation (in which the skeleton undergoes a larger deformation and retains the shape obtained in response to the applied force).

For example, with reference to the general view of FIG. 11, in case a minimal distance 140 between the edges of sections 137 and 139 of temple arms 44 and 43, respectively, is smaller than the size of the nape of surgeon 26. The skeleton of one or both of sections 137 and 139 may be deformed and shaped, so that the revised (adjusted) distance 140 matches the corresponding size of the nape of surgeon 26. Moreover, in this configuration, upholsteries 138 of sections 137 and 139 snugly fit over the respective section of the nape of surgeon 26.

Reference is now made to inset 135. In some embodiments, upholstery 138 of sections 137 and 139 comprises a suitable texture for improving the gripping to the nape of the head of surgeon 26. For example, the outer surface of upholstery 138 (intended to be placed in contact with the nape) may comprise grooves having a suitable orientation (e.g., parallel to the XY plane, and/or parallel to the XZ plane) or parallel to the longitudinal axis of the respective section 137 and 139 of temple arms 44 and 43. In some embodiments, upholstery 138 may have any other suitable texture other than grooves, which is adapted to improve the gripping between sections of the nape of surgeon 26 and sections 137 and 139 of HMD 22.

Figure 12:
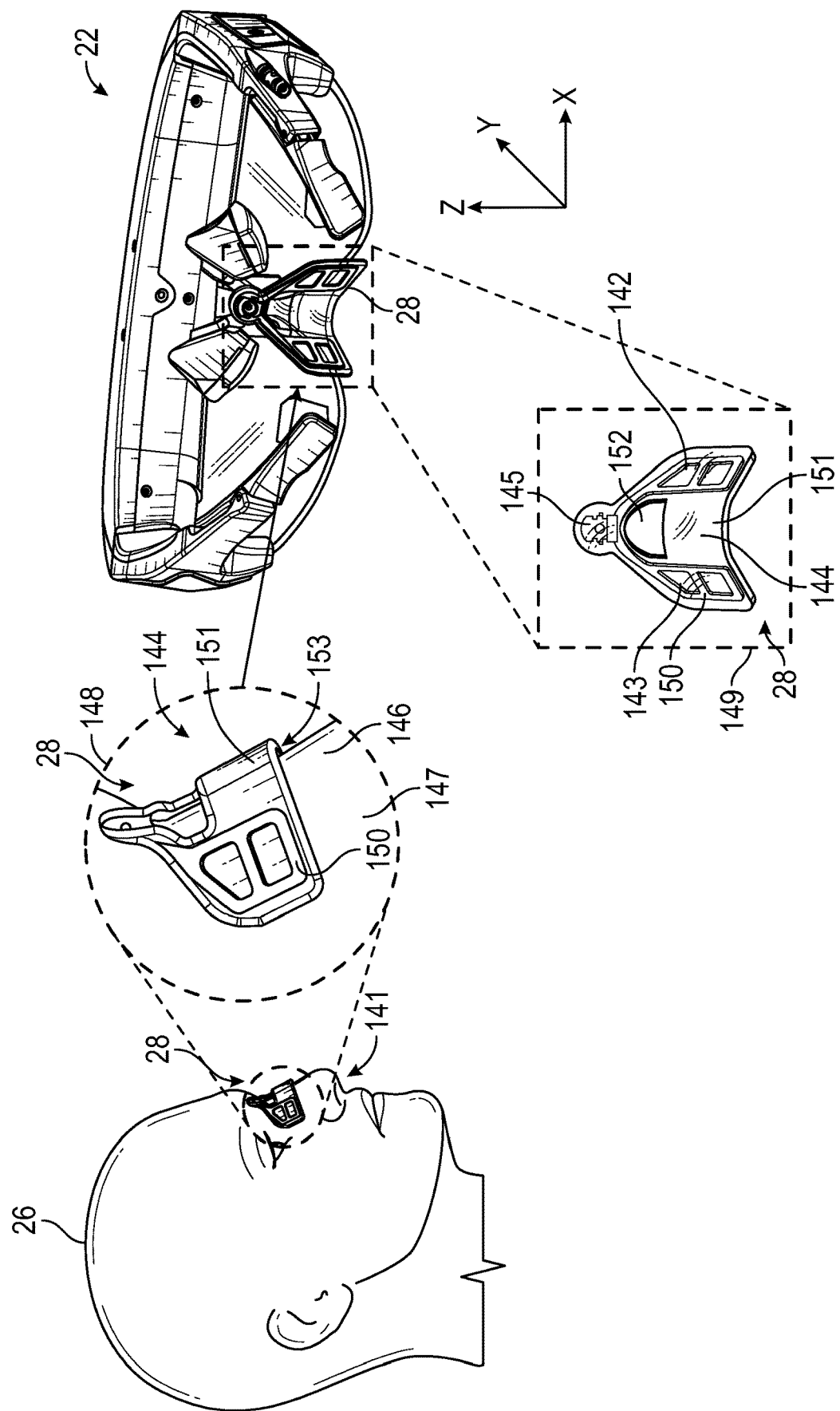
FIG. 12 is a schematic pictorial illustration of a nose pad for use in any of the HMDs shown in FIGS. 1, 2A, 2B, 3, 21A-29E, and 31A-32.

FIG. 12 is a schematic pictorial illustration of a nose pad 28, in accordance with an embodiment.

In some embodiments, nose pad 28 is implemented in HMD 22, but in some embodiments, nose pad 28 may also be implemented, mutatis mutandis, in other sorts of HMDs, including any of the HMDs disclosed herein.

Reference is now made to the head of surgeon 26 for showing the position of nose pad 28 over a nose 141 of surgeon 26.

Reference is now made to an inset 148 showing a higher magnification of nose pad 28 placed over a section of nose 141. In the example of inset 148, nose pad 28 is presented with an upholstery 151 of polymer (e.g., a viscoelastic material, such as but not limited to the viscoelastic material of cushion 125 of FIG. 10A above, or any other suitable type of elastomer (e.g., silicone-based polymer), neoprene, polyurethane or any other suitable material), which is partially transparent for the sake of the presentation.

In some embodiments, nose pad comprises a metal-based skeleton 150, which is surrounded by upholstery 151 and may comprise similar materials and functionality to that of skeleton 136 shown in FIG. 11 above.

Nose 141 has a forward section 146, whose cartilage and nerves may be sensitive to being in constant contact with nose pad 28. However, the skin in the left and right sides 147 of nose 141 is not in close proximity to the cartilage, and therefore, is less sensitive to be in contact with nose pad 28.

Reference is now made to an inset 149 showing a frontal view of nose pad 28. Note that in the general view of HMD 22, nose pad 28 and HMD 22 are shown from a rear view, which is opposite to the front view of inset 149.

In some embodiments, nose pad 28 comprises a left section 142, a right section 143 and middle section 144 connecting between the left and right sections. In some embodiments, middle section 144 has an opening, but in some embodiments, middle section 144 may have a solid structure without an opening.

In some embodiments, nose pad comprises a section 145 adapted to couple between nose pad 28 and the frame of HMD 22. In an embodiment, section 145 may have a DOF for being adjusted relative to the frame of HMD 22. The DOF may be implemented using any suitable type of tilting assembly, which may be based on a hinge, or on a vertical axis as described in detail, for example, in any of FIGS. 9, 10A, 10B, and 11 above.

The DOF implemented in section 145 may be operated synchronously or asynchronously with an additional DOF (also referred to herein as a vertical DOF or a pantoscopic-tilting assembly, and is described in detail in connection with FIG. 14 below), between the frame and the AR display of HMD 22.

In some embodiments, section 145 may be rigidly coupled to the frame of HMD 22, without a degree of freedom for tilting relative to the frame.

In one implementation, nose pad 28 comprises skeleton 150 disposed in sections 142, 143 and 145, so as to adjust the shape of nose pad 28 to the shape of nose 141.

Reference is now made back to inset 148. In some embodiments, nose pad 28 is adapted to be shaped so that section 144 of nose pad 28 is not in direct contact with forward section 146 of nose 141, and in some embodiments, an air gap 153 is buffering between section 144 and forward section 146.

In some embodiments, the surgeon may place section 144 directly over forward section 146 of the nose.

In some embodiments, section 145 may comprise an assembly configured to adjust the height (e.g., along the Z-axis) of nose pad 28 relative to the frame of HMD 22. The adjustment may be carried out in steps of predefined movement range, or may be continuous using one or more suitable assemblies implemented in nose pad 28, or in a part of the frame of HMD 22 (e.g., in housing 29), or therebetween.

In some embodiments, upholstery 151 may have a suitable texture, such as but not limited to the textures described above for cushion 125 and upholstery 138 of FIGS. 10A and 11, respectively.

In some embodiments, nose pad 28 may comprise two ball joints for sections 142 and 143, respectively, so as to provide the user with improved adjustment of the shape of nose pad 28 relative to the width of nose 141.

Figure 13:
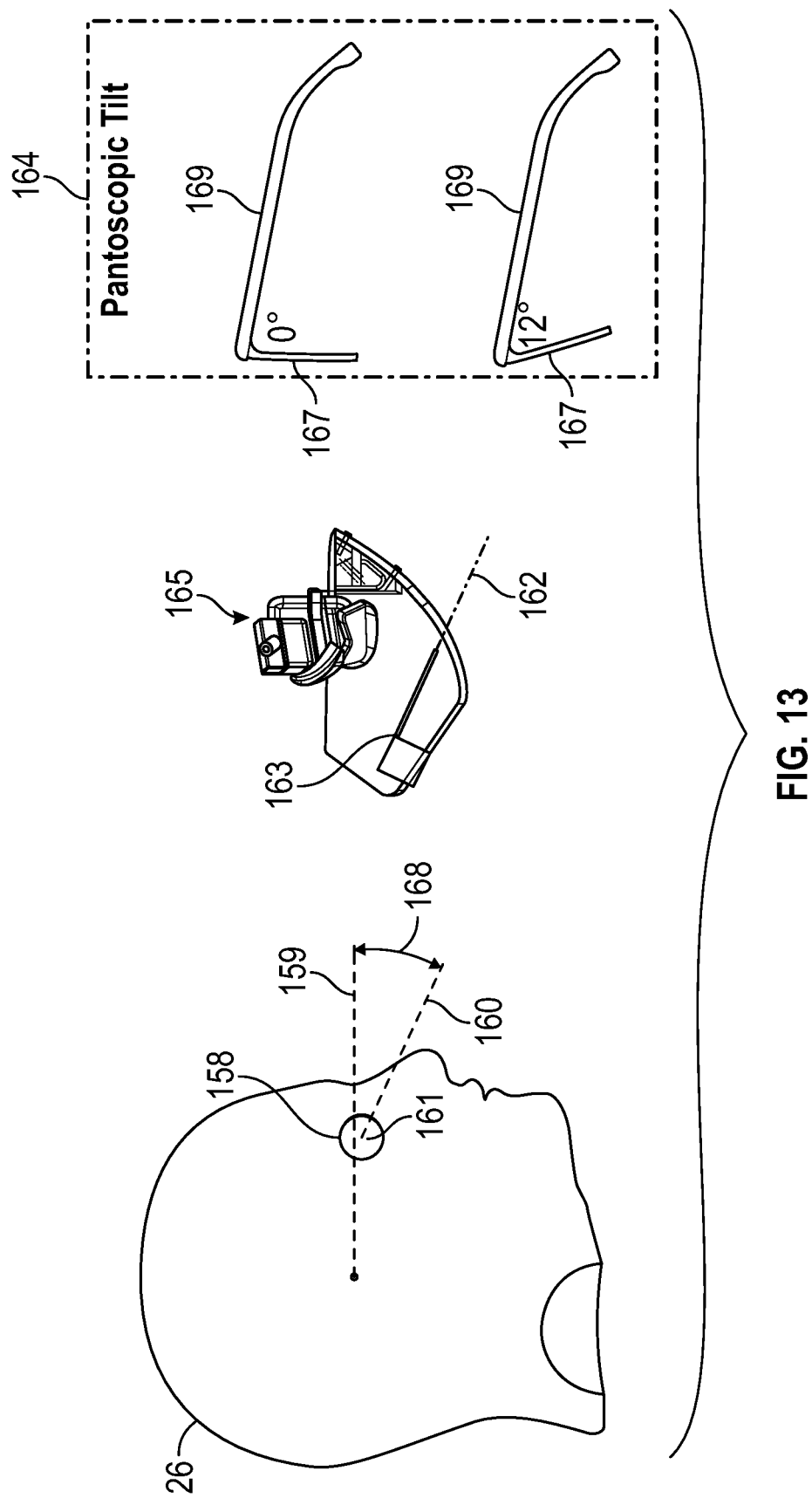
FIGS. 13 and 14 are schematic pictorial illustrations of DOF implementations implemented in pantoscopic tilting assemblies (PTAs) implemented with an optical engine for use in any of the HMDs shown in FIGS. 1, 2A, 2B, 3, 21A-29E, and 31A-32.
Figure 14:
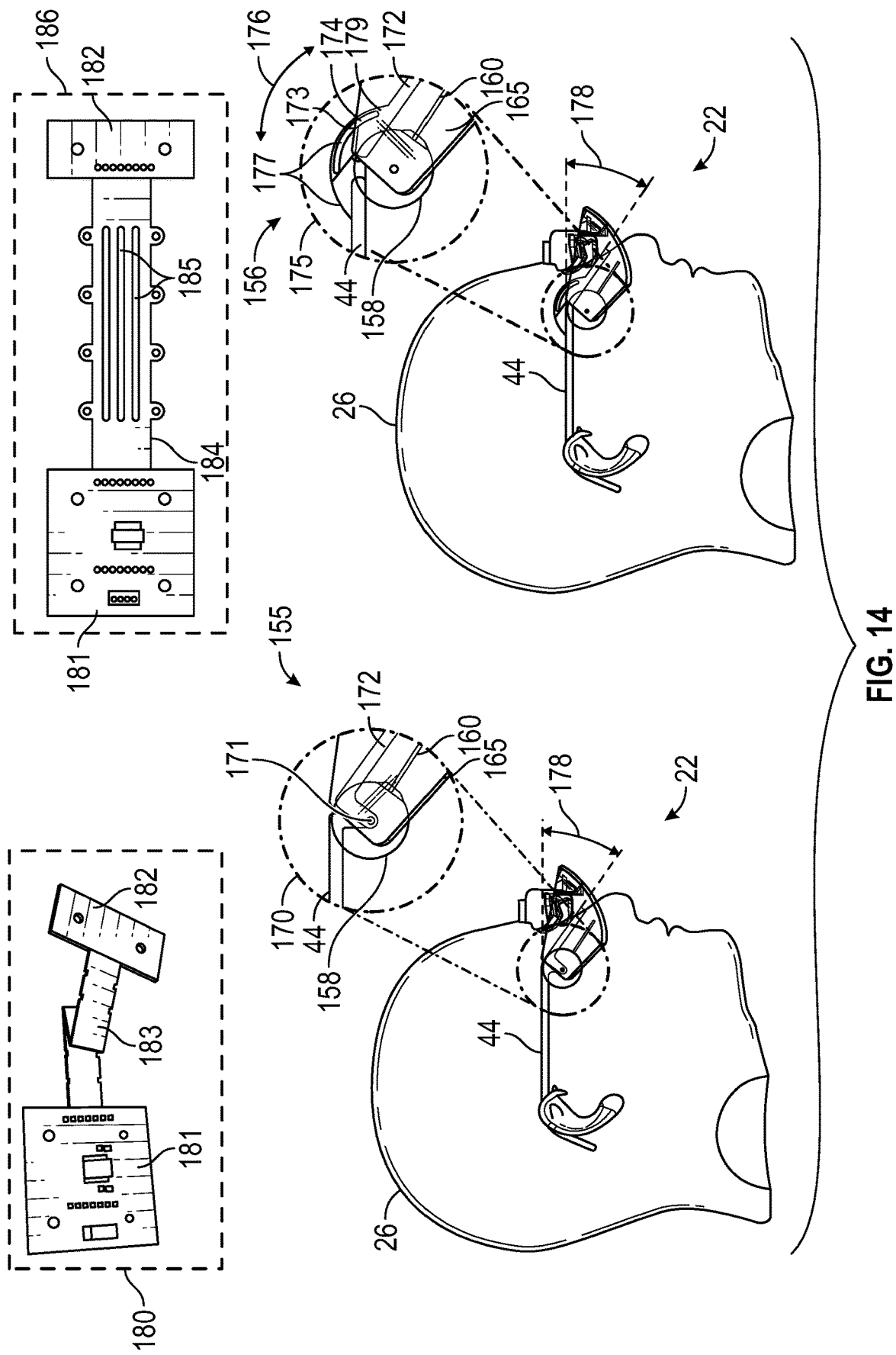

FIGS. 13 and 14 are schematic pictorial illustrations of pantoscopic tilting and a pantoscopic-tilting assembly (PTA) 155 of an optical engine (OE) 165, in accordance with various embodiments. Optical engine 165 may replace, for example, OE 42 of FIG. 2A above, and/or OE 55 of FIG. 3 above.

In some embodiments, PTA 155 may be implemented, mutatis mutandis, in HMDs 22 and 50, in HUD 700 and in any other sort of HMD assembly using embodiments described in connection with FIGS. 13 and 14 below, and/or in connection with FIGS. 21A-29E, and 31A-32. Moreover, the implementation of PTA 155 may be affected by several operational modes of surgical procedures shown and described, for example, in connection with FIGS. 15A-15C below. The PTA 155 may be used to, for example, rotate a see-through display assembly relative to a frontal plane of a user, such as surgeon 26.

Reference is now made to FIG. 13, which is used mainly as an introduction to pantoscopic tilting and optional implementations thereof.

In the example of FIG. 13, an eyeball 158 of surgeon 26 has an optical axis (OA) 160 (also referred to herein as a first optical axis) extended from the center of an eyeball through pupil 161 of surgeon 26. An angle 168 (e.g., of about 25°) is defined between a horizontal line 159 and OA 160.

In the example of FIG. 13, an optical axis 162 of OE 165 (also referred to herein as a second optical axis) is defined from an OE eye relief point 163 within OE 165.

Reference is now made to a frame 164 showing fixed pantoscopic tilts implemented in respective pantoscopic tilt angle of about 0° and 12° applied to the upper and lower glasses of frame 164. In the example of frame 164, the pantoscopic tilt angle is defined between a frame 169 and glasses 167 (e.g., corresponding to AR display 15 of HMD 22).

In some embodiments, in near-eye display AR-based systems, such as in HMD 22 of system 11, the pantoscopic tilt is set for aligning the second optical axis with the first optical axis. In the example of FIG. 13, the pantoscopic tilt is set for aligning optical axis 162 to converge with optical axis 160.

Reference is now made to FIG. 14, showing DOFs of vertical axes implemented using examples of vertical tilting assemblies, referred to herein as pantoscopic tilting assemblies (PTAs) 155 and 156.

In some embodiments, a pantoscopic tilt angle 178 of about 35° is applied to HMD 22 using PTAs 155 and 156. However, other pantoscopic tilt angles may be applied (e.g., angles between 25 degrees and 45 degrees, angles between 30 degrees and 40 degrees, angles between 33 degrees and 37 degrees, overlapping ranges thereof, or any value within the recited ranges). Reference is now made to an inset 170 showing the vertical DOF implemented in PTA 155.

In some embodiments, PTA 155 comprises a bar 172 rigidly coupled to optical engine 165, and a hinge 171 configured to rotate bar 172 relative to temple arm 44 of the frame of HMD 22. In accordance with several embodiments, the movement is a relative movement about a vertical axis between the optical engine and the frame.

In one non limiting example, the frame of HMD 22, and more specifically, housing 29, temple arms 43 and 44, and nose pad 28, are not moved when PTA 155 is tilting OE 165 in angle 178 to the desired pantoscopic tilt angle, and the same applies to the frame when PTA 156 (described herein) is tilting OE 165 in angle 178 to the desired pantoscopic tilt angle.

In some embodiments, OE 165 may comprise an optical assembly comprising one or more cameras, one or more light sources and other components, which are all moved in accordance with the DOF implemented using PTA 155 of PTA 156.

Reference is now made to an inset 175 showing the vertical DOF implemented in PTA 156. In some embodiments, PTA 156 comprises bar 172 coupled to (e.g., molded with) a rotatable section 179 of a disc having a slit 174. PTA 156 further comprises an assembly 177, so that when tilting OE 165 relative to temple arm 44 of the frame, section 179 is moved relative to assembly 177 in a selected tangential direction 176 and locked (e.g., using a locking element 173)

at a predefined position within slit 174 to fixate OE 165 at the desired pantoscopic angle relative to temple arm 44 and the other components of the frame of HMD 22. The implementation of the vertical DOF using PTA 156 is also referred to herein as a virtual axis because the components are being moved (e.g., rotated about an axis) without using a physical hinge, such as hinge 171 of PTA 155.

In some embodiments, PTA 156 may comprise any other suitable type of a virtual axis. For example, with reference to inset 110 of FIG. 9 above, PTA 156 may comprise three sections, such as sections 112, 113 and 114 shaped to be adapted to frame and OE 165, and referred to herein as first, second and third sections, respectively. In such embodiments, the first section is coupled to OE 165, the second section is coupled to the frame (e.g., to the respective temple arm of each side, or to housing 29), and the third section is adapted to bend in response to a relative movement between the first and second sections when surgeon 26, or any other user, adjusts the pantoscopic tilt angle.

In some embodiments, PTA 156 may comprise a rigid bar coupled to the frame and a flexible arm having properties similar to that of skeleton 136 shown and described in inset 135 of FIG. 11 above. In such embodiments, in response to surgeon 26 adjusting the pantoscopic tilt angle, the flexible arm is adapted to transform from an elastic deformation to a plastic deformation, and to retain the shape obtained in response to the force applied for the adjustment of the pantoscopic tilt angle.

These particular configuration of PTAs 155 and 156 are shown by way of example, in order to illustrate certain problems that are addressed the example implementation of the vertical DOF for controlling the pantoscopic angle of the optical engine relative to the frame of HMD 22. Embodiments of the disclosure, however, are by no means limited to this specific sort of example configurations and implementations, and the principles described herein may similarly be implemented in other sorts of vertical DOFs used for controlling pantoscopic tilt angles in near-eye display AR-based image-guided surgical systems (including, but not limited to, the structures described below with reference to FIG. 23B). Embodiments may be used in non-medical applications as well, such as for commercial and/or consumer applications, including athletics and fitness, gaming, driving, product design, navigation, manufacturing, logistics, shopping and commerce, educational training, remote collaboration, etc.

In some embodiments, optical engine 165 typically comprises electronic devices configured for exchanging electrical signals with processor 33 (shown in FIG. 1) and other components of HMD 22 and system 11.

In some embodiments, HMD 22 comprises hardware configured to exchange the signals while executing the vertical DOF using PTAs 155 and 156.

Reference is now made to insets 180 and 186 showing two example implementations of the hardware configured to exchange the signals while applying the pantoscopic tilting to OE 165. In some embodiments, a rigid PCB 181, having electronic devices mounted thereon, is disposed in the frame of HMD 22 (e.g., in housing 29 of FIG. 1), a rigid PCB 182, having other electronic devices mounted thereon, is disposed in OE 165, and a flexible PCB 183 is configured to bend in at least two axes in order to enable smooth exchange of the electrical signals between housing 29 and OE 165.

In the configuration of inset 186, flexible PCB 184 has openings 185 shaped as slits along an axis the flexible PCB 184, so as to enable bending of flexible PCB 184 along two or more axes, and thereby to enable the exchange of electrical signals between housing 29 and OE 165.

The configuration of the rigid and flexible PCBs of insets 180 and 186 are shown by way of example, and in some embodiments, any other suitable configuration may be used for enabling the exchange of electrical signals between housing 29 and OE 165 while performing the pantoscopic tilting as well as when HMD 22 operates at a preset pantoscopic tilt angle.

In some embodiments, the glasses of the display (e.g., displays 49a and 49b of FIG. 3 above) may have a separate frame (e.g., display assembly frame 41), which is separated from the optical frame that comprises the OEs, cameras, sensors, and other devices. In such embodiments, frame 41 remains static relative to the head (ears & nose), and the optical frame has a vertical DOF (based on a hinge or on a virtual axis) relative frame 41 around the center of the eye ball of the surgeon.

Figure 15A:
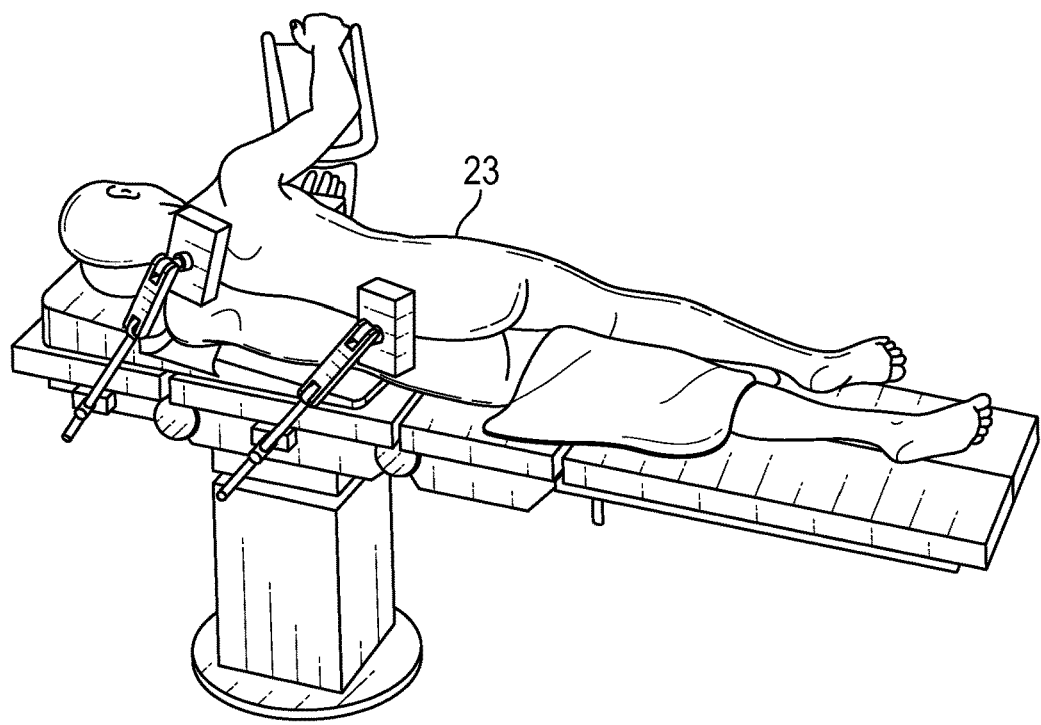
FIGS. 15A, 15B, and 15C are schematic pictorial illustrations of use cases of the PTA of FIG. 14 used in several types of surgical procedures.
Figure 15B:
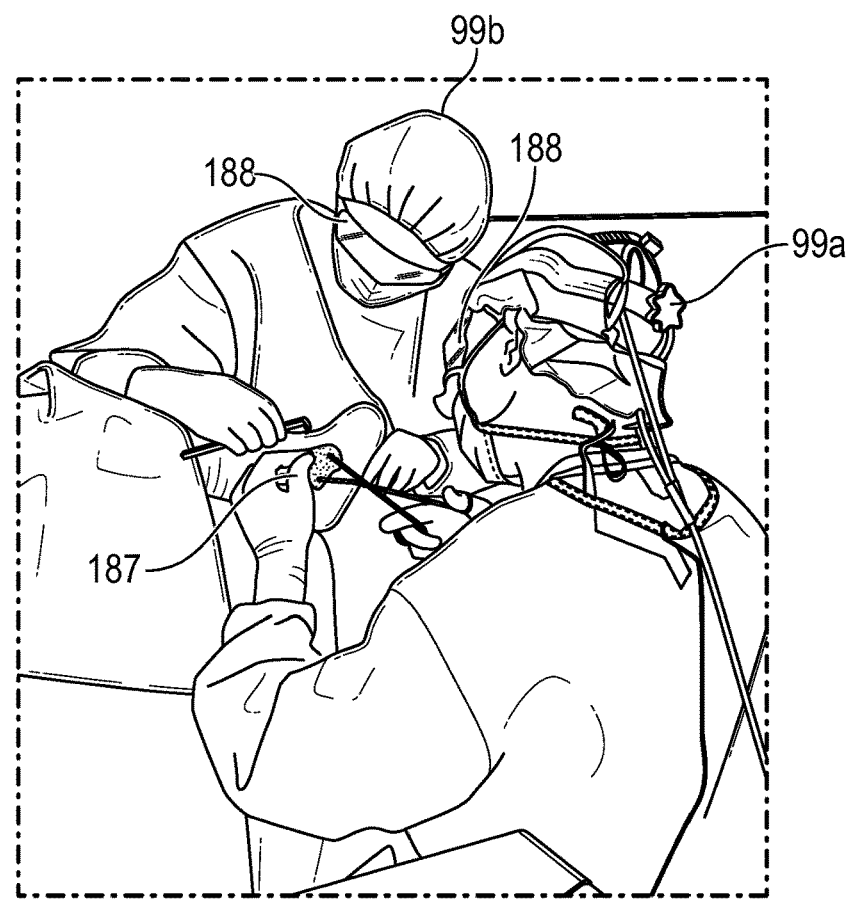
Figure 15C:
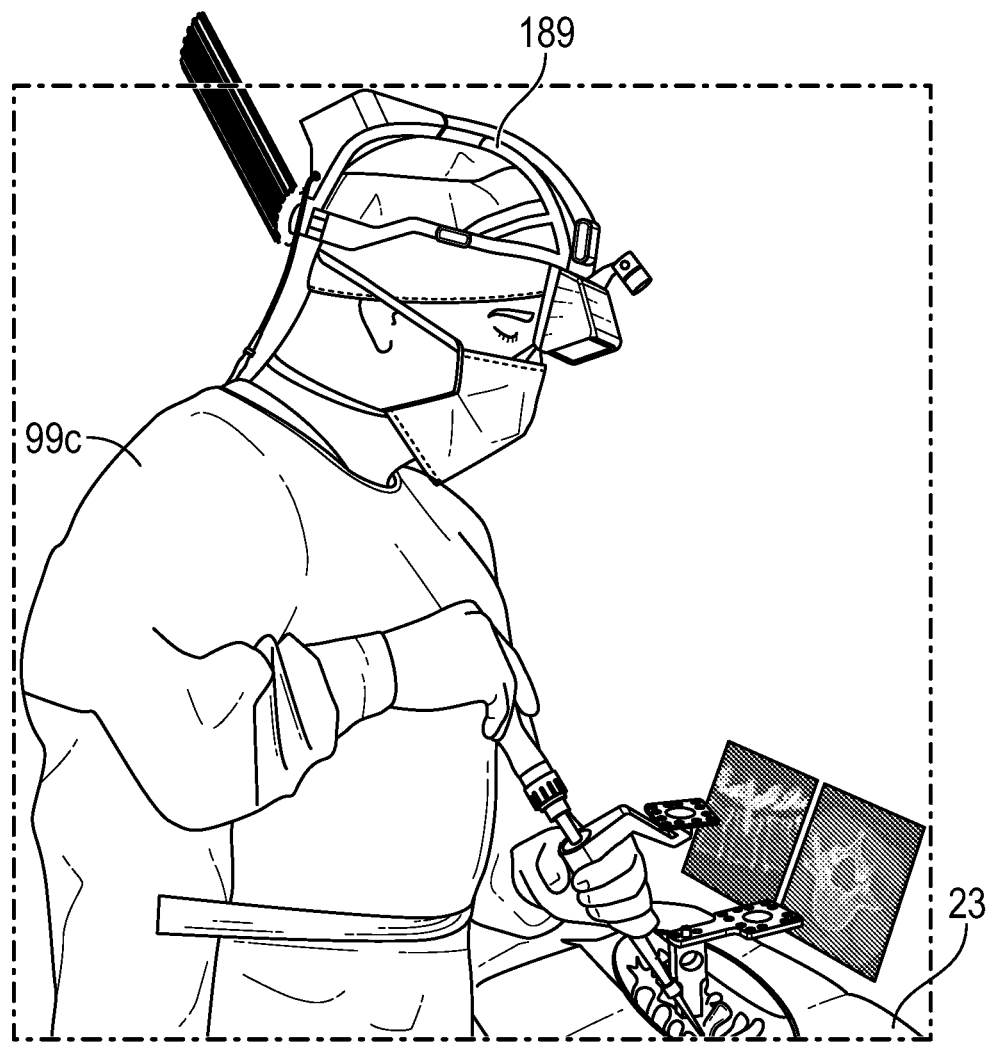

FIGS. 15A, 15B and 15C are schematic pictorial illustrations of use cases of PTA 155 and 156 used in several types of surgical procedures (e.g., in both sitting and standing positions), in accordance with several embodiments. PTA 2355, described below with reference to FIG. 23B, may also be used in such procedures. These figures help to illustrate, among other things, certain advantages or benefits of including an adjustable pantoscopic tilt, such as to enable the PTA 155, 156, 2355 or the like to be set to different pantoscopic tilt angles for different types of surgical procedures that may each utilize a different Line of Sight (LOS) to an area of interest (e.g., surgery site on a patient body), in accordance with several embodiments.

Reference is now made to FIGS. 15A and 15B showing a spine surgery based on a lateral approach.

A surgeon view of a patient or Line of Sight (LOS) to an area of interest (e.g., surgery site on a patient body) during a medical intervention, is typically downwards, e.g., in a vertical or oblique manner (e.g., since the patient or surgical site is located beneath the eyes of the surgeon). However, in some cases, the surgeon may view the patient or surgical site, or the surgeon's LOS during the medical intervention may be different than downwards, e.g., horizontal or substantially horizontal or straight ahead (e.g., in case the surgical site or area of interest is located in front or substantially in front of the surgeon's eyes). In such cases, the HMD should allow a horizontal or substantially horizontal view and/or augmented reality view of the area of interest.

For example, in a Lateral Lumbar Interbody Fusion (LLIF) procedure, a lateral approach may be required. In such a procedure, patient 23 may be positioned on the side as shown in FIG. 15A, and the surgeons (shown in FIG. 15B) take a side approach and center an incision 187 over the flank of patient 23. The surgeon shown in FIG. 15B is in a sitting position thus viewing the surgery site in a substantially horizontal manner.

Using the lateral approach, the surgeons, in one embodiment, insert the surgical tools from a lateral trajectory, and therefore, can reach the vertebrae and intervertebral discs without moving the nerves or opening up muscles in the back.

In some embodiments, the surgeons of FIG. 15B use an HMD 188 comprising PTA 155 or PTA 156 described in FIG. 14 above (or PTA 2355 described below with reference to FIG. 23B). In some embodiments, the PTA of HMD 188 is configured to set any suitable pantoscopic tilt angle. In the lateral approach example of FIG. 15B, a surgeon 99a may select a first pantoscopic tilt angle (e.g., an angle of about 15° or other angle, such as an angle between 5° and 30°, between 10° and 25°, between 10° and 20°, overlapping ranges thereof, or any value within the recited ranges), and a surgeon 99b may select a different pantoscopic tilt angle (e.g., an angle of about 30° or other angle, such as an angle between 20° and 40°, between 25° and 35°, between 30° and 40°, between 25° and 40°, between 30° and 50°, overlapping ranges thereof, or any value within the recited ranges).

Reference is now made to FIG. 15C showing a surgical approach in which patient 23 lies on the abdomen and chest, with his/her back facing surgeon 26, who is standing, as also shown in the surgical procedure described in FIG. 1 above.

In some embodiments, a surgeon 99c of FIG. 15C uses a HMD 189 comprising a suitable PTA, such as PTA 155 or PTA 156 (or PTA 2355 described below with reference to FIG. 23B). For the sake of conceptual clarity, when surgeon 99c is standing and is inserting the surgical tool(s) from an upper trajectory, or while looking downwards, the surgical approach is referred to herein as "a standing posture" (of the surgeon). In the standing posture example of FIG. 15C, surgeon 99c may select a pantoscopic tilt angle of about 35° or any other suitable pantoscopic tilt angle, and may also adjust the pantoscopic tilt angle during the surgical procedure using the vertical DOF enabled by PTAs 155 and 156 (and 2355).

As described with reference to FIG. 13 above, the pantoscopic tilt angle may be defined as the angle between an axis of the frame and an axis of the display (e.g., between a horizontal axis of the frame and an optical axis of the display). In some embodiments, the PTAs of both HMDs 188 and 189 are configured to set any suitable pantoscopic tilt angle between about 5° and about 40°, and the adjustment of the pantoscopic tilt angle may be continuous or in predefined steps (e.g., of about 1° or 5°). In some implementations, the PTAs are configured to move (e.g., to pivot, rotate, or slide) the display about an axis that is aligned or substantially aligned with a center of an eyeball of a user of the display. In some implementations, such movement can have a number of benefits, including, for example, alignment of the user's optical axis with the display's optical axis, the ability to focus on both near and distant objects using the same head-mounted display device (e.g., glasses) at the same time, and enhancing image quality for both straight ahead viewing and downgaze viewing. As used herein, pantoscopic tilt angle may refer to an amount of tilt toward a wearer's cheek (e.g., with a higher value referring to movement in a direction that moves the display closer to the wearer's cheek).

Figure 29A:
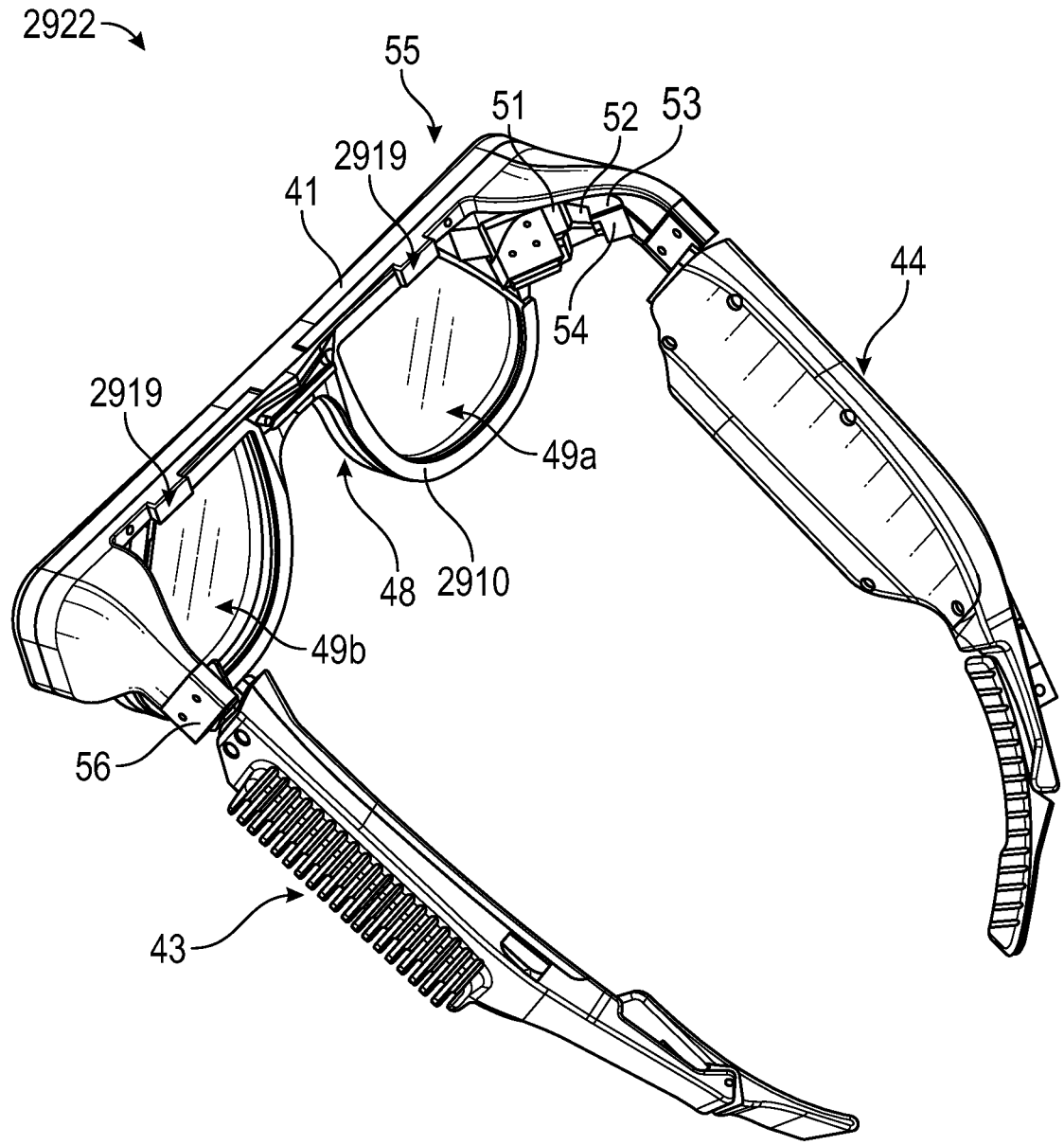
FIGS. 29A-29E illustrate another embodiment of a head-mounted display incorporating a clip-on lens assembly that can be used with any of the head-mounted displays disclosed herein.

In some embodiments, HMDs 188 and 189 may replace, for example, any of HMD 22 (of FIGS. 1 and 2A above), HUD 700 (of FIG. 2B above), HMD 50 of FIG. 3 above, HMD 2122 of FIG. 21A, and/or HMD 2922 of FIG. 29A.

In some embodiments, the vertical DOF (implemented for example, in PTAs 155, 156, and 2355) may be used, mutatis mutandis, in any other surgical or other interventional procedures. In such procedures, the surgeon or other professional may select any suitable posture of himself and of the patient. Moreover, in accordance with several embodiments, even though specific procedures are typically performed while the surgeon and/or the patient are in a specific posture, the surgeon or other professional may decide to change his or her posture relative to that of the patient during the procedure and/or the patient's posture, and therefore, an adjustable pantoscopic tilt angle, as implemented for example in PTAs 155, 156, and 2355, is important for the quality of the procedure.

Example Structured Light Projector Implementation

Figure 16:
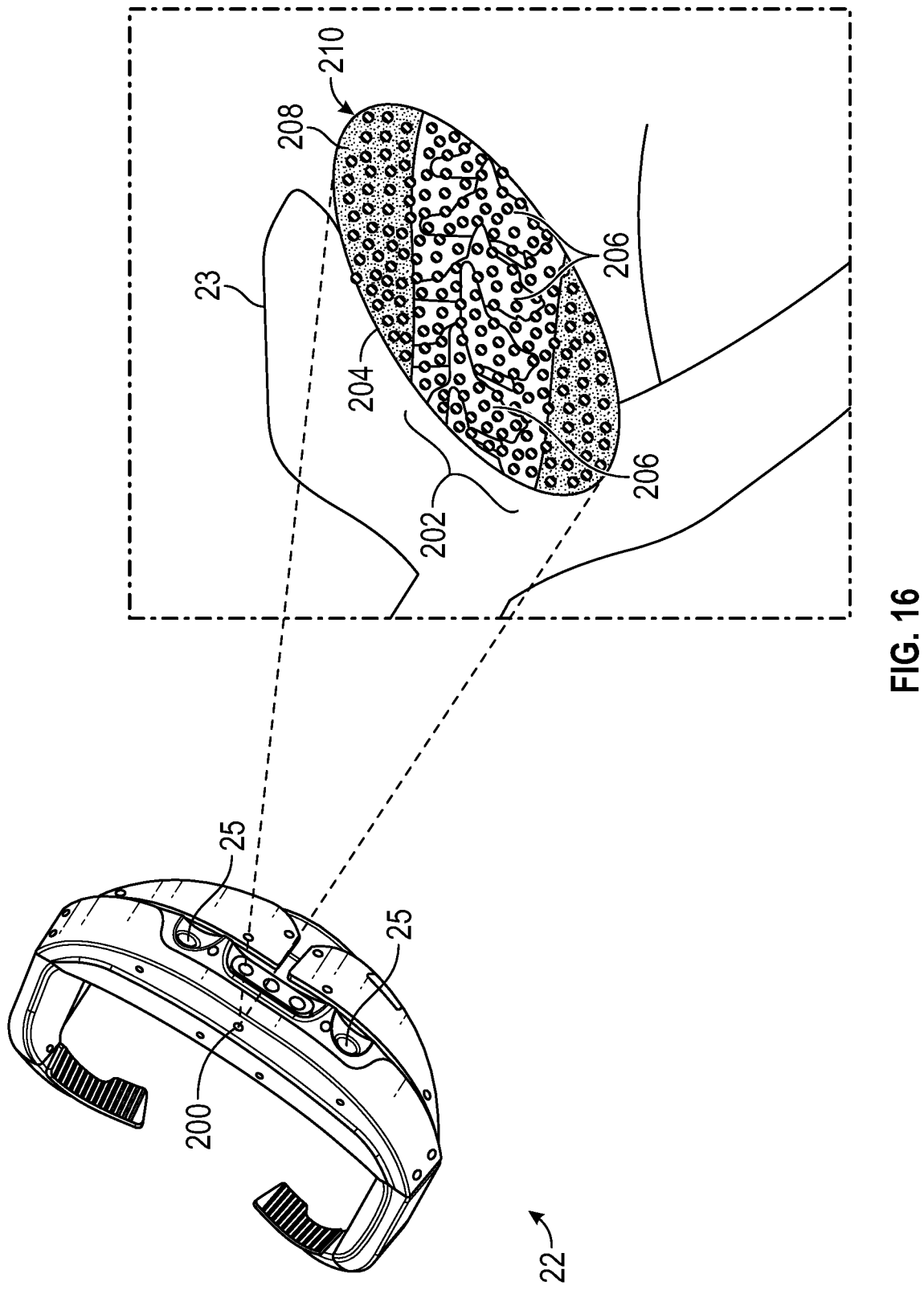
FIG. 16 is a schematic pictorial illustration of a structured light projector for use in any of the HMDs shown in FIGS. 1, 2A, 2B, 3, 21A-29E, and 31A-32.

FIG. 16 is a schematic pictorial illustration of a structured light projector (SLP) 200 implemented in HMD 22, in accordance with an embodiment. SLP 200 may also be implemented, mutatis mutandis, in HUD 700 of FIG. 2B, in HMD 50 of FIG. 3, in HMDs 188 and 189 of FIGS. 15B and 15C, respectively, in HMD 2122 of FIG. 21A, in HMD 2922 of FIG. 29A, and in any other suitable type of HMD used in any suitable type of near-eye-display surgical procedures or other medical therapeutic and/or diagnostic procedures. Although medical applications are well-suited for several embodiments, non-medical applications also benefit from many embodiments described herein. For example, non-medical applications may involve consumer or commercial applications such as athletics and fitness, gaming, driving, product design, navigation, manufacturing, logistics, shopping and commerce, educational training, remote collaboration, etc.

In some embodiments, the surgeon (e.g., surgeon 26) makes an incision 202 (e.g., similar to incision 24) in the skin 208 and other tissues of the back of patient 23, so as to expose one or more vertebrae 206 of patient 23 intended to be operated. Some of the areas intended to be operated on may not be exposed or fully exposed by incision 202, depending on the medical application.

In some embodiments, SLP 200 comprises a laser dot pattern projector configured to apply to an area 204 on the organ or body region in question (e.g., the back) of patient 23, a structured light comprising a large number (e.g., between hundreds and hundreds of thousands) of dots 210 arranged in a suitable pattern. This pattern serves as an artificial texture for identifying positions on large anatomical structures lacking fine details of their own (e.g., skin 208 and the surface of vertebrae 206 but the edge thereof).

In some embodiments, using a pseudo random pattern of dots 210, clusters can be uniquely identified and used for disparity measurements. In some embodiments, the disparity measurements are used for calculating depth, and for enhancing the precision of the 3D imaging of area 204.

In some embodiments, the wavelength of dots 210 may be visible to a human eye (e.g., blue, green, or red color) or invisible (e.g., infrared). In accordance with several embodiments, blue dots may advantageously retain their original shape (e.g., round) and appear sharp on skin 208. In some embodiments, SLP 200 is configured to direct blue laser dots or green laser dots (depending on the quality and other parameters of the laser source and optics) to area 204.

In some embodiments, cameras 25 (e.g., RGB cameras) may be used for producing a 3D image of area 204, and based on the images received from cameras 25, processor 33 is configured to produce the 3D image of area 204.

In some embodiments, an additional depth sensing technique may be implemented in HMD 22. The technique relies on a single camera with a precisely calibrated offset relative to SLP 200. In such embodiments, based on the calibrated offset, processor 33 is configured to produce depth information without the need for stereo cameras. The depth information may be obtained by identifying the relative shift of dot clusters.

Additionally, or alternatively, system 11 may comprise a structured light projector mounted on a wall or on an arm of the operating room. In such embodiments, a calibration process between the structured light projector and the one or more cameras (e.g., cameras 25 on HMD 22, or one or more suitable cameras mounted at any suitable position of the operating room) may be required for obtaining the 3D image based on dots 210 projected on area 204.

In some embodiments, SLP 200 may apply an infrared or any other beam having an invisible wavelength (or range of wavelengths), and one or more cameras, such as camera 16 described in FIG. 1 above, may be used for obtaining the 3D image.

The position of SLP 200 in HMD 22 is selected by way of example, and in some embodiments, SLP 200 may be mounted on HMD 22 (or on any other of the HMDs and HUD described above) at any other suitable position.

Rolling Shutter Example

Figure 17:
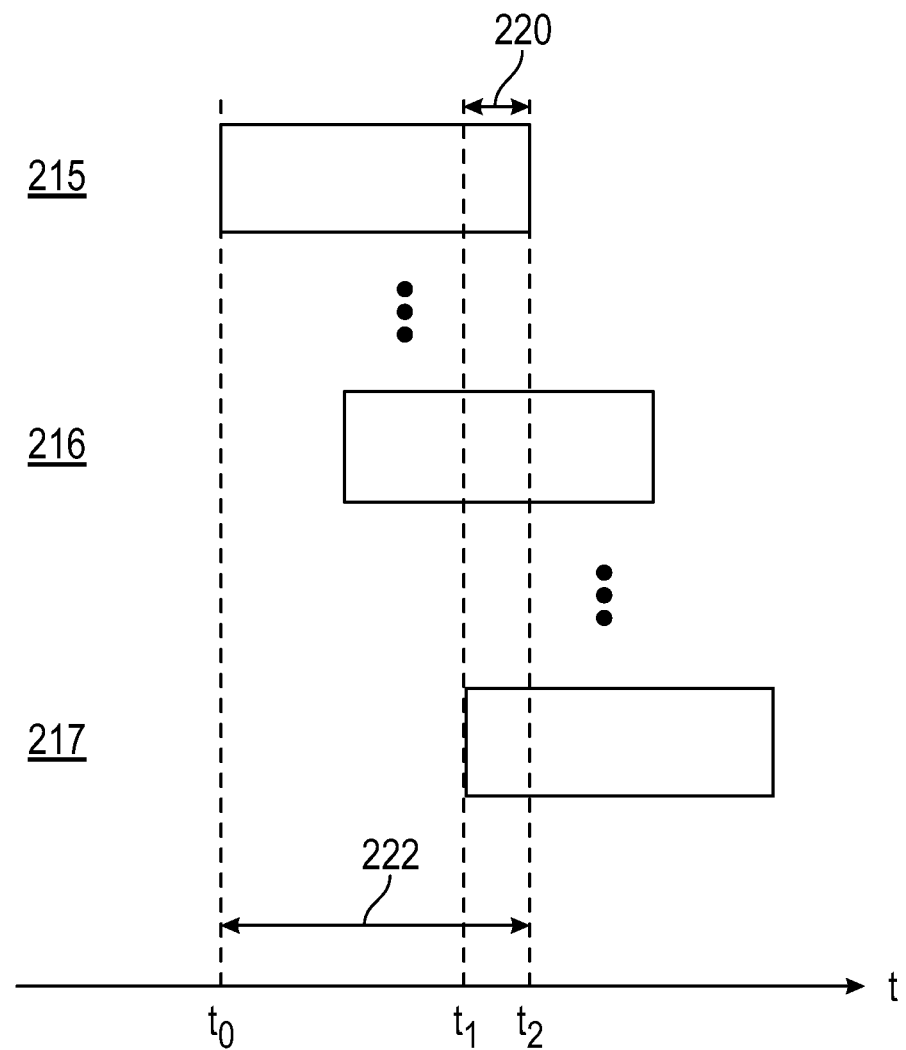
FIG. 17 is a diagram that schematically illustrates a method for generating a synchronously exposed image by applying an illumination strobe to a rolling shutter image sensor within an integration time of the rolling shutter for use in any of the HMDs shown in FIGS. 1, 2A, 2B, 3, 21A-29E, and 31A-32.

FIG. 17 is a diagram that schematically illustrates a method for generating an image by applying a strobe of an infrared (IR) light source to a rolling shutter image sensor within an integration time of the rolling shutter, in accordance with an embodiment.

In some embodiments, an image sensor of camera 16 (which may comprise an IR camera or an RGB camera configured to act as an IR camera) comprises any suitable number of pixels, for example, a 2 Mb sensor comprising about 2 millions of pixels, or a sensor between 0.5 Mb and 10 Mb, between 1 Mb and 5 Mb, between 2 Mb and 10 Mb, overlapping ranges thereof, or any value within the recited ranges.

In some embodiments, each pixel has an integration time, which is a time interval in which the pixel is open for exposure. FIG. 17 shows the integration time of the three pixels along the time scale "t."

In some embodiments, numerals 215, 216 and 217 refer to the integration times of the first pixel, the 1-millionth pixel, and the 2-millionth pixel of the image sensor, respectively. The first pixel is opened at t0 and closes at t2, defining an integration time 222 of the pixel.

In some embodiments, the duration of integration time 222 may be determined using the integral capacitance of each pixel of the image sensor. In some embodiments, at t0 the capacitor of the first pixel is opened for charging by voltage produced by the first pixel in response to sensing photons on the surface of the first pixel. At t2 the charging of the capacitor of the first pixel is stopped, and ready for being read to produce the IR image described in FIG. 1 above.

In some embodiments, the integration time of the first pixel (e.g., between t0 and t2) is between 5 milliseconds and 15 milliseconds (e.g., between 5 milliseconds and 10 milliseconds, between 6 milliseconds and 10 milliseconds, between 8 milliseconds and 15 milliseconds, overlapping ranges thereof, about 8 milliseconds, or any value within the recited ranges. Similarly, as shown in the row having numeral 217, the integration time of the 2-millionth pixel starts at t1 (about 7 ms after t0) and lasts for an integration time of between 5 milliseconds and 15 milliseconds (e.g., between 5 milliseconds and 10 milliseconds, between 6 milliseconds and 10 milliseconds, between 8 milliseconds and 15 milliseconds, overlapping ranges thereof, about 8 milliseconds, or any value within the recited ranges. Note that within between 5 milliseconds and 15 milliseconds (e.g., between 5 milliseconds and 10 milliseconds, between 6 milliseconds and 10 milliseconds, between 8 milliseconds and 15 milliseconds, overlapping ranges thereof, about 8 milliseconds, or any value within the recited ranges (e.g., between t0 and t2) all the pixels of the image sensor have been opened. Moreover, at a time interval 220 between t1 and t2 (e.g., about 1 ms) all the pixels of the image sensor are open at the same time.

In some embodiments, at time interval 220, processor 33 (or any other processor or controller of system 11) controls (e.g., via a driver) IR projectors 17 to direct a strobe of an IR beam, referred to herein as an IR strobe, to the area being operated in the body of patient 23. Moreover, during the same time interval 220, processor 33 (or any other processor or controller of system 11) controls camera 16 to acquire the IR image from the area being operated.

In accordance with several embodiments, camera 16 comprises a rolling shutter, which performs the reading time of each pixel sequentially. In some embodiments, the rolling shutter of camera 16 is operated in a global-shutter mode by implementing sufficiently-long pixel integration time 222 and directing the IR strobe at time interval 220 in which all the pixels (e.g., 2 million pixels) of the image sensor are opened.

In such embodiments, artifacts related to rolling shutters, such as but not limited to shifting of objects in the image due to the serial reading time of the pixels, are reduced or eliminated.

Example Pairing Subsystem

Figure 18:
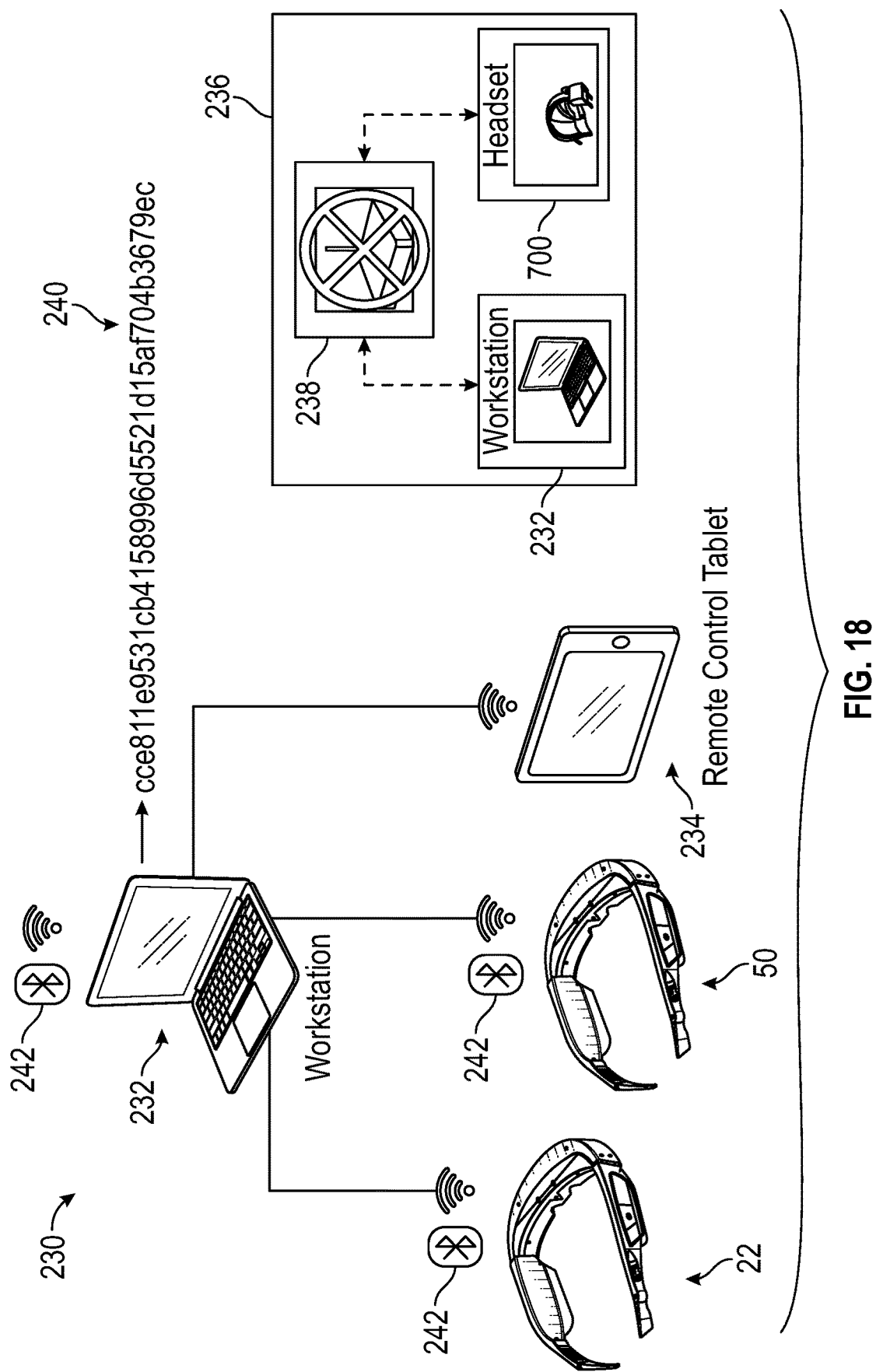
FIG. 18 is a schematic pictorial illustration of a direct pairing system for directly pairing between a workstation (WS) and any of the HMDs shown in FIGS. 1, 2A, 2B, 3, 21A-29E, and 31A-32.

FIG. 18 is a schematic pictorial illustration of a direct pairing subsystem 230 for directly pairing between a workstation (WS) 232 and HMDs 22 and 50, in accordance with an embodiment.

In some embodiments, subsystem 230 is a communication subsystem of system 11 shown in FIG. 1 above. In accordance with several embodiments, subsystem 230 is configured to connect between WS 232 and any sort of one or more HMDs and HUD (including any of the HMDs or HUDs disclosed herein), in addition to or instead of HMDs 22 and 50.

In some embodiments, WS 232 serves as a Wi-Fi hotspot device and the devices of system 11 (e.g., HMDs) are typically connected to WS 232 of subsystem 230. The pairing process between the devices is referred to herein as "hopping" and two operational modes of the pairing. The hopping and pairing are described hereinafter, and also in connection with FIG. 19 below.

Reference is now made to an inset 236 showing another configuration of a communication subsystem. In the example of inset 236 the subsystem comprises: (i) WS 232, (ii) HUD 700 (and/or other suitable HMDs described herein), and (iii) a wireless router 238. Router 238 may be hacked, and for cybersecurity reasons, there may be a motivation to exclude a router (such as router 238) from the configuration of the communication subsystem.

Reference is now made back to the general view of FIG. 18. In some embodiments, subsystem 230 comprises a remote control station (e.g., a tablet) 234 intended to be used by the medical staff in preparing for the surgical procedure, and during the surgical or other interventional procedure (in addition to the HMD).

In some embodiments, WS 232, HMDs 22 and 50 and tablet 234 are connected wirelessly using a service set identifier (SSID), which is a sequence of characters that uniquely names a wireless local area network (WLAN) comprising WS 232, HMDs 22 and 50, tablet 234 and optionally additional devices. The SSID may be configured to allow stations of subsystem 230 to connect to the desired network when multiple independent networks operate in the same physical area. Moreover, WS 232 may be configured to generate a password, such as password 240, and the password may be sent to HMDs 22 and 50 to enable a secured connection using a key exchange process described herein. This additional security layer may be used for improving the cybersecurity of the network of subsystem 230.

In some embodiments, in the example configuration of FIG. 18, WS 232 serves as a client and the HMD(s) intended to be connected serve(s) as a server. Embodiments related to the pairing process are described in connection with FIG. 19 below.

In some embodiments, the communication technique may comprise Wi-Fi, which is a family of network protocols, based on the IEEE 802.11 family of standards, which may be used in wireless local area networking (LAN) applications.

In some embodiments, WS 232 and HMDs 22 and 50 comprise Bluetooth (BT) adapters and the key exchange process is carried out using BT technology, which is a short-range wireless technology standard that is used for exchanging data between fixed devices (e.g., WS 232 implemented in a desktop or a laptop computer) and mobile devices (such as but not limited to HMDs 22 and 50) over short distances using ultra-high frequency (UHF) radio waves in the industrial, scientific and medical (ISM) bands (e.g., between 2.402 GHz and 2.48 GHz).

In some embodiments, WS 232 (and optionally other WSs located at the same medical center or facility) comprise an additional Wi-Fi adapter, also referred to herein as a second Wi-Fi adapter (not shown). In such embodiments, the key exchange process is carried out using a peer2peer (P2P) connection. In such embodiments, WS 232 is using two Wi-Fi connections: a first Wi-Fi connection for hotspot connection, and a second Wi-Fi connection for the key exchange process using the second Wi-Fi adapter.

In some embodiments, WS 232 is configured to encode the hotspot key (e.g., password 240) into an optical code or other machine-readable code such as a barcode or a quick response (QR) code, generated using a suitable software or online tools and displayed over the display of WS 232 or on any other suitable display. In such embodiments, the HMD intended to be paired with WS 232 is configured to scan the optical code or machine-readable code (e.g., barcode or QR code) and decipher the key for performing the key exchange process and the pairing.

In some embodiments, the optical code or machine-readable code (e.g., barcode or QR code) scanning may be carried out using one or more additional cameras 25 (e.g., RGB cameras), or using camera 16 configured to capture a monochromatic image instead of an IR image (e.g., RGB camera that can also function as an IR camera).

This particular configuration of subsystem 230 is shown by way of example, in order to illustrate certain problems related to connectivity and cyber security that are addressed by embodiments of the disclosure, and to demonstrate the application of these embodiments in enhancing the performance of such a communication subsystem. Embodiments of the disclosure, however, are by no means limited to this specific sort of example communication subsystem, and the principles described herein may similarly be applied to other sorts of communication subsystems used in suitable types of AR-based image-guided surgical systems.

Figure 19:
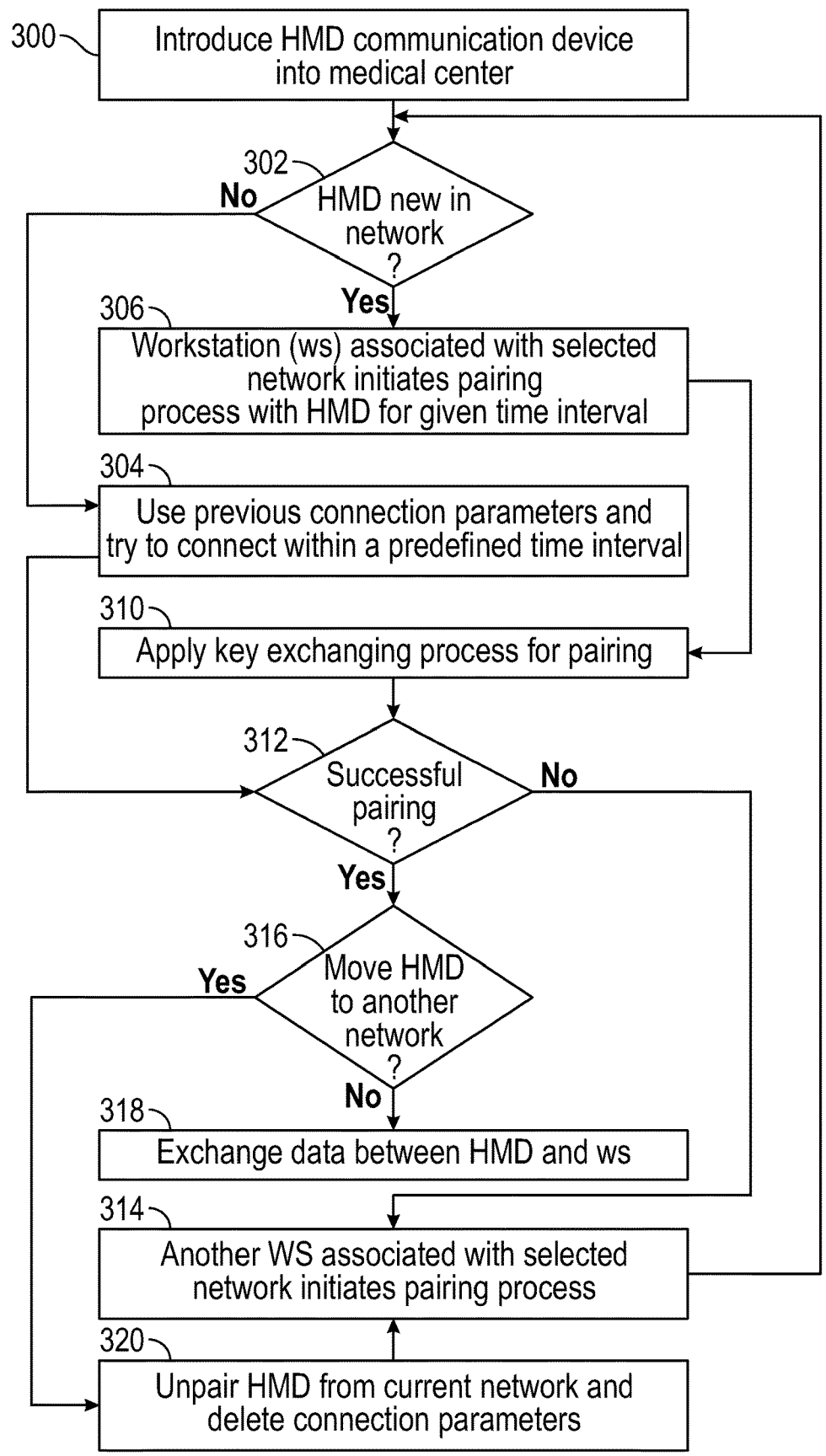
FIG. 19 is a flow chart that schematically illustrates a method for directly pairing between the WS of FIG. 17 and multiple HMDs selected from any of the HMDs shown in FIGS. 1, 2A, 2B, 3, 21A-29E, and 31A-32.

FIG. 19 is a flow chart that schematically illustrates a method for directly pairing between WS 232 and HMD 22, in accordance with various embodiments.

The flow chart may also be applicable, mutatis mutandis, for connecting between WS 232 and one or more of HMDs 50, 188, and 189 of FIGS. 3, 15B and 15C, respectively, and for connecting between WS 232 and HUD 700 of FIG. 2B, HMD 2122 of FIG. 21A and/or HMD 2922 of FIG. 29A.

Moreover, the method is applicable for connecting between any workstation and any suitable device configured to display information, such as but not limited to images and markers, over the organ being operated using augmented reality techniques or any suitable technique other than augmented reality.

The method begins at a scanning step 300, with processor 33 introducing a communication device of HMD 22 into a medical center.

At a first decision step 302, the method differentiates between a first use case in which HMD 22 is known to the selected network, and a second use case in which HMD 22 is new to the selected network.

In the first use case, the method proceeds to a parameters application step 304, in which processor 33 uses a set of parameters, typically parameters used in the previous connection (also referred to herein as previous parameters) that are known based on the previous connection between HMD 22 and WS 232. Note that in this use case, the paring process has a predefined time limit and is performed automatically, so that the method proceeds to check whether the pairing is successful (shown in a step 312 described hereinafter)

In the second use case, the method proceeds to a pairing initiation step 306, in which the workstation (e.g., WS 232) initiated the pairing process with HMD 22 for a given time interval. Note that the time intervals (also referred to herein as time limits) of steps 304 and 306 are determined by a user or an administrator of the system. Therefore, the time intervals of steps 304 and 306 may be similar to one another, or may differ from one another.

In some embodiments, the pairing process described below has a predefined time interval (e.g., about 15 seconds, about 20 seconds, about 30 seconds), also referred to herein as a time limit. The implications of the time limit are described in more detail below.

At a key exchange process step 310, the key exchange process is performed for pairing between HMD 22 and WS 232. The key exchange process may be based on Bluetooth, P2P, QR code or any other communication technique and protocols, as described in detail in connection with FIG. 18 above. In accordance with several embodiments, password 400 and the SSID of the network are stored in HMD 22 (or in any other HMD introduced into the medical center as described in step 300 above) in advance (e.g., typically before step 300).

At a second decision step 312, processor 33 of HMD 22 (and optionally the processor of WS 232) check whether the pairing was performed successfully. Note that, in accordance with several embodiments, the pairing process has to be successful within the time limits described in steps 304 and 306 above for the two respective use cases.

As described above, in the first use case (e.g., HMD 22 has already been paired with the selected network), the method proceeds from step 304 directly to step 312 for checking whether or not the pairing has been successful.

In case the pairing fails and/or is not completed successfully within the predefined time limit, the method proceeds to an alternative WS pairing initiation step 314 in which a processor of another workstation (e.g., other than WS 232) associated with the selected network initiates the pairing process. Subsequently the method loops back to step 302 described above.

In case pairing is successful within the time limit, the method proceeds to a third decision step 316, in which the user of subsystem 230 (e.g., surgeon 26) and/or processor 33 check whether to move HMD 22 to another network. The decision to move HMD to another network may be performed based on operational considerations, clinical consideration, technical (e.g., communication) considerations, or any other suitable consideration.

In case there is no need to move HMD 22 to another network, the method proceeds to a data exchanging step 318 in which HMD 22 and WS 232 exchange data during surgical operations or between surgical operations, as described above.

In case HMD 22 is moved to another network, the method proceeds to an unpairing step 320 in which HMD 22 is unpaired from WS 232, and the connection parameters for connecting with WS 232 are deleted from the storage of HMD 22. After unpairing between HMD 22 and WS 232, the method loops back to step 314 and further to step 306 as described above.

The method of FIG. 19 is provided by way of example in order to illustrate embodiments related to secure communication performed directly between a workstation and an HMD without having a router or any other sort of intermediate communication device. As described in connection with FIG. 18 above and in accordance with several embodiments, the elimination of the router is particularly advantageous for complying with cybersecurity requirements in communicating between HMD 22 and WS 232 or between any other two or more suitable medical and communication devices.

The method is simplified for the sake of conceptual clarity and relies on the description of the hardware of FIG. 18 above. In some embodiments, the method may be implemented, mutatis mutandis, on any other suitable hardware comprising any suitable type of medical devices and/or communication devices.

Example Electronic Subsystem

Figure 20:
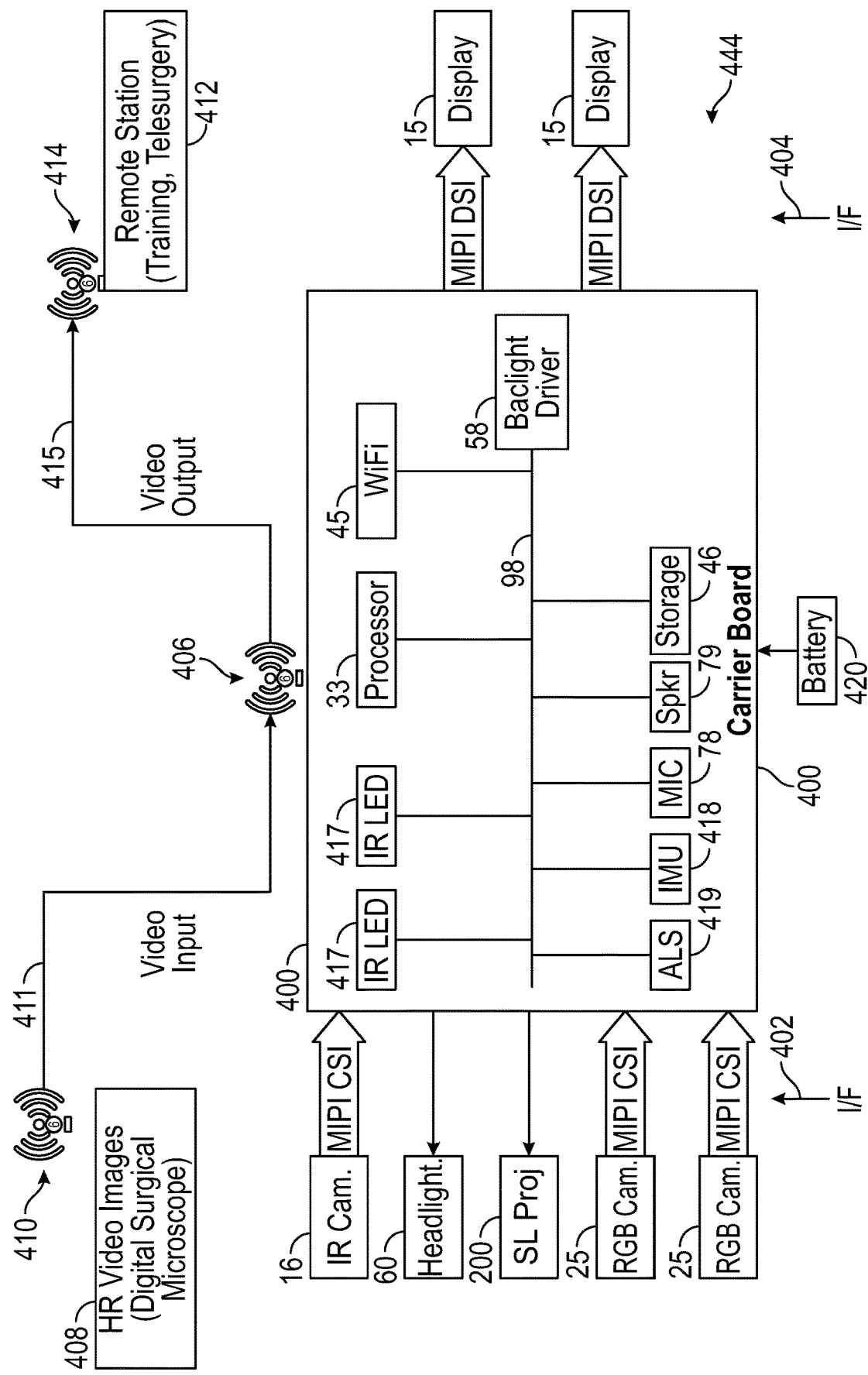
FIG. 20 is a block diagram that schematically illustrates an implementation of an electronic architecture of the system of FIG. 1.

FIG. 20 is a block diagram that schematically illustrates an implementation of an architecture of an electronic subsystem (ES) 444 of system 11, in accordance with an embodiment of the disclosure.

In some embodiments, ES 444 may be implemented, mutatis mutandis, in any of the HMDs and HUD described above or below.

In some embodiments, ES 444 comprises a carrier board (CB) 400 made from a suitable PCB or any other suitable substrate having traces for exchanging signals between components described herein.

In some embodiments, ES 444 comprises a battery pack, referred to herein as a battery 420, or any other suitable power source configured to supply electrical power to ES 444. As described above, ES 444 may comprise a supercapacitor or ultracapacitor (not shown) connected to CB 400 in parallel with battery 420 and configured to be used for eliminating lengthy boot-up when changing battery 420 of HMD 22 (or any other HMD or HUD described above or below).

In some embodiments, ES 444 comprises processor 33, wireless communication device 45 (e.g., a Wi-Fi-6 transceiver connected to a Wi-Fi-6 antenna 406), and storage device 46, which are mounted on CB 400.

In some embodiments, ES 444 comprises a system-on-chip (SOC) device or a system-on-module (SOM) device comprising processor 33, wireless communication device 45, storage device 46, a graphic processing unit (GPU) (not shown), an artificial intelligence (AI) accelerator (not shown), image signal processors (ISPs) and/or other components. For example but not by way of limitation, the SOC device may comprise any suitable SOC device selected from the Snapdragon family produced by Qualcomm (San Diego, CA).

In some embodiments, ES 444 comprises controllers 417 configured to control and drive IR LED projectors 17 described in FIG. 1 above, an IMU controller 418 configured to drive IMU 18 described in FIG. 1 above, and an ambient light sensor (ALS) controller 419 of light sensor 19 described in FIG. 1 above. Controllers 417 and 418 are mounted on CB 400. In some embodiments, IMU 18 may comprise both the sensing device and the drive circuitry. Similarly, ALS controller 419 may be integrated with sensor 19, and controller 417 may be integrated with LED projectors 17.

In some embodiments, ES 444 comprises backlight driver 58, which is described with reference to FIG. 3 above and is configured to drive and adjust the current supplier to display 15.

In some embodiments, ES 444 comprises a microphone assembly (MA) 78 comprising a microphone and electronic circuitry thereof, and a speaker assembly (SA) 79 comprising a speaker and electronic circuitry thereof. MA 78 and SA 79 are mounted on CB 400.

In some embodiments, ES 444 comprises a bus 98 configured to conduct power signals and data signals between the aforementioned devices mounted on CB 400, and also to conduct power signals and data signals between CB 400 and external entities described herein.

In some embodiments, ES 444 comprises an interface 402 configured to exchange power signals and data signals between CB 400 and: (i) camera 16, (ii) HA 60 (or any other headlight assembly described above), (iii) SLP 200, and (iv) additional cameras 25 (e.g., RGB cameras).

In some embodiments, interface 402 comprises a Camera Serial Interface (CSI), which is a specification of the Mobile Industry Processor Interface (MIPI) Alliance, referred to herein as MIPI CSI, configured to conduct, between (i) cameras 16 and 25 and (ii) CB 400 the signals for producing the IR images and the RGB images, respectively.

In some embodiments, ES 444 comprises an interface 404 configured to output signals indicative of the AR images (described above) between CB 400 and the displays of the HMD. In some embodiments, the displays comprise display 15 associated with OE 42 (shown and described in FIG. 2A above). In some embodiments, the display 15 may comprise displays 49a and 49b of HMD 50 shown and described in FIG. 3 above.

In some embodiments, interface 404 comprises a MIPI Display Serial Interface (MPI DSI), which is a high-speed interface that is used in various types of consumer devices.

In some embodiments, ES 444 is configured to exchange video signals with external entities. In some embodiments, ES 444 is configured to transmit video of the scene captured by RGB cameras 25 together with the rendered augmented reality images.

In some embodiments, the transmission may be carried out using Wi-Fi-6 (an IEEE standard for wireless local-area networks) for obtaining low-latency and high-speed transmission of the signals.

The transmission technique is not limited to Wi-Fi-6 and may also be carried out over the (fifth generation) 5G cellular network or other communications networks.

In some embodiments, these communication techniques may be used for operating room staff to observe exactly what the surgeon (e.g., surgeon 26) sees, and for training and/or telesurgery applications.

In some embodiments, surgeon 26 performs the surgery or other medical intervention in the operating room shown in FIG. 1, and receives feedback/comments/instructions on how to proceed with the surgical or other interventional procedure, from remote surgeons or other professionals located at a remote station 412 having a suitable communication assembly 414 (e.g., Wi-Fi-6) configured to receive signals of a video output 415.

In some embodiments, the signals of video output 415 may be recorded for documenting the surgical or other interventional procedure in medical records.

In some embodiments, ES 444 is configured to receive and display input signals of video, and more specifically of high-resolution (HR) video images also referred to herein as video input 411, received from an external source 408 having a suitable communication assembly 410 (e.g., Wi-Fi-6) configured to receive signals of video input 411.

In some embodiments, ES 444 is configured to receive input video 411 from a digital surgical microscope, and to display the received video signals using the aforementioned digital loupe techniques that are described, for example, in U.S. Provisional Patent Application 63/234,272, and in PCT Publication No. WO2023/021450, the disclosure of both of which are incorporated herein by reference. Note that in this use case, displaying such HR images received from the digital surgical microscope may provide surgeon 26 HR images rendered in augmented reality.

In some embodiments, ES 444 is configured to receive and display input signals of input video 411 comprising endoscopic video received from an endoscopy system. This use case allows surgeon 26 to perform various types of endoscopic or laparoscopic surgical procedures without diverting the gaze to a remote monitor.

In some embodiments, external source 408 may comprise any other suitable video source(s) configured to produce any suitable type of HR video images. In such embodiments, processor 33 is configured to receive video input 411 comprising these HR video images, and to display the images over displays 15 (or any other suitable type of display) using the AR techniques described above or any other presentation technique. Moreover, processor 33 is configured to present any other types of patient information received from external source 408.

In some embodiments, the GPU and the AI accelerator of ES 444 may be used together with processor 33 for controlling system 11 (of FIG. 1 above) using voice commands. For example, the GPU and the AI accelerator of ES 444 may be used together with processor 33 for voice and/or command recognition, using any suitable type of artificial intelligence techniques.

This particular configuration of ES 444, external source 408 and remote station 412 is shown by way of example, in order to illustrate certain problems that are addressed by embodiments of the disclosure and to demonstrate the application of these embodiments in enhancing the performance of system 11 and similar types of image-guided surgical systems. Embodiments of the disclosure, however, are by no means limited to this specific sort of example electronic architecture, and the principles described herein may similarly be applied to other sorts of HMDs and hardware used in suitable types of AR-based image-guided surgical systems and other sorts of image-guided surgical systems. Although medical applications are well-suited for several embodiments, non-medical applications also benefit from many embodiments described herein. For example, non-medical applications may involve consumer or commercial applications such as athletics and fitness, gaming, driving, product design, navigation, manufacturing, logistics, shopping and commerce, educational training, remote collaboration, etc.

Additional Example Head-Mounted Display

FIGS. 21A-21D illustrate another example embodiment of a head-mounted display 2122. The head-mounted display 2122 has many similarities to other head-mounted displays disclosed herein, including, for example, head-mounted display 22 of FIG. 2A, head-mounted display 50 of FIG. 3, and head-mounted display 700 of FIG. 2B, discussed above, and the same or similar reference numbers are used to refer to the same or similar components. Accordingly, the present description of head-mounted display 2122 focuses on differences from the head-mounted displays 22, 50, and 700. Any elements or features discussed herein with reference to other head-mounted displays, such as head-mounted display 22, 50, or 700, may be incorporated into head-mounted display 2122, and likewise any elements or features discussed herein with reference to head-mounted display 2122 may be incorporated into other head-mounted displays discussed herein, such as head-mounted displays 22, 50, or 700.

Some benefits of the design of the head-mounted display 2122 are related to ergonomics, comfort, and/or the ability to enable a user, such as surgeon 26, to utilize the system for relatively long periods of time, such as for four hours or more, without unnecessary fatigue and/or other negative consequences. For example, in some embodiments, a head-mounted display like the head-mounted display 22 of FIG. 2A may weigh approximately 260 g, and such a design may transfer roughly 200 g of that weight to the user's nose through the nose pad 28. While this may be acceptable in some situations, in some situations, such as during longer operations, it may be desirable to reduce the load on the user's nose to, for example, 90 g or less. A design such as the head-mounted display 2122 shown in FIG. 21A can accomplish such a benefit. For example, the head-mounted display 2122 can distribute weight around the wearer's head, including to the wearer's forehead and the back of the wearer's head, to reduce at least some of the weight applied to the wearer's nose. Such a configuration can also reduce pressure on the wearer's temples which can be another relatively weight-sensitive area, in addition to the nose. Stated another way, such a head-mounted display can more widely distribute pressure over larger and/or less sensitive areas, such as the forehead and the back of the head.

The head-mounted display 2122 combines certain features of other head-mounted displays disclosed herein, including the head-mounted display 22, head-mounted display 50, and head-mounted display 700. For example, as discussed in greater detail below, the head-mounted display 2122 includes left and right temple housings that have some similarities to the left and right temple arms of head-mounted display 22, but that are not in contact with and/or being supported by the wearer's temples or ears. As another example, as discussed in greater detail below, the head-mounted display 2122 includes a rear pad and adjustable strap mechanism that can be similar to those used in the head-mounted display 700. Additionally, some embodiments can include an optional upper or top strap that can further distribute weight over the top of a wearer's head.

Another advantage of a design that distributes weight to less sensitive areas of a wearer's head, such as the design of the head-mounted display 2122, is that additional weight may be added to the head-mounted display without significantly increasing the pressure on the wearer's head in any particular spot or in a sensitive area. For example, a flashlight assembly may be attached to the head-mounted display without significantly increasing the pressure on the wearer's head in any particular spot or in a sensitive area.

Figure 21B:
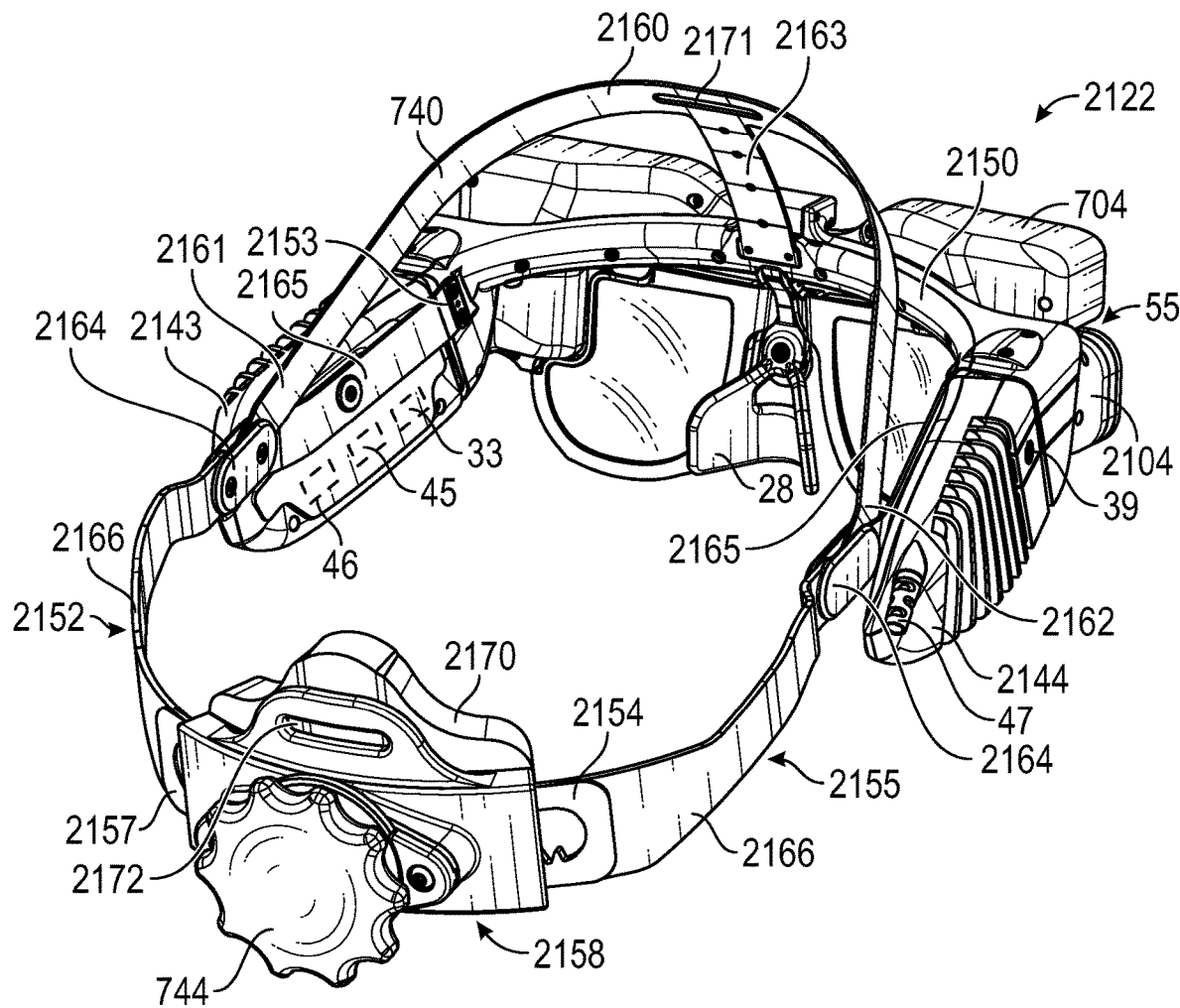
Figure 21C:
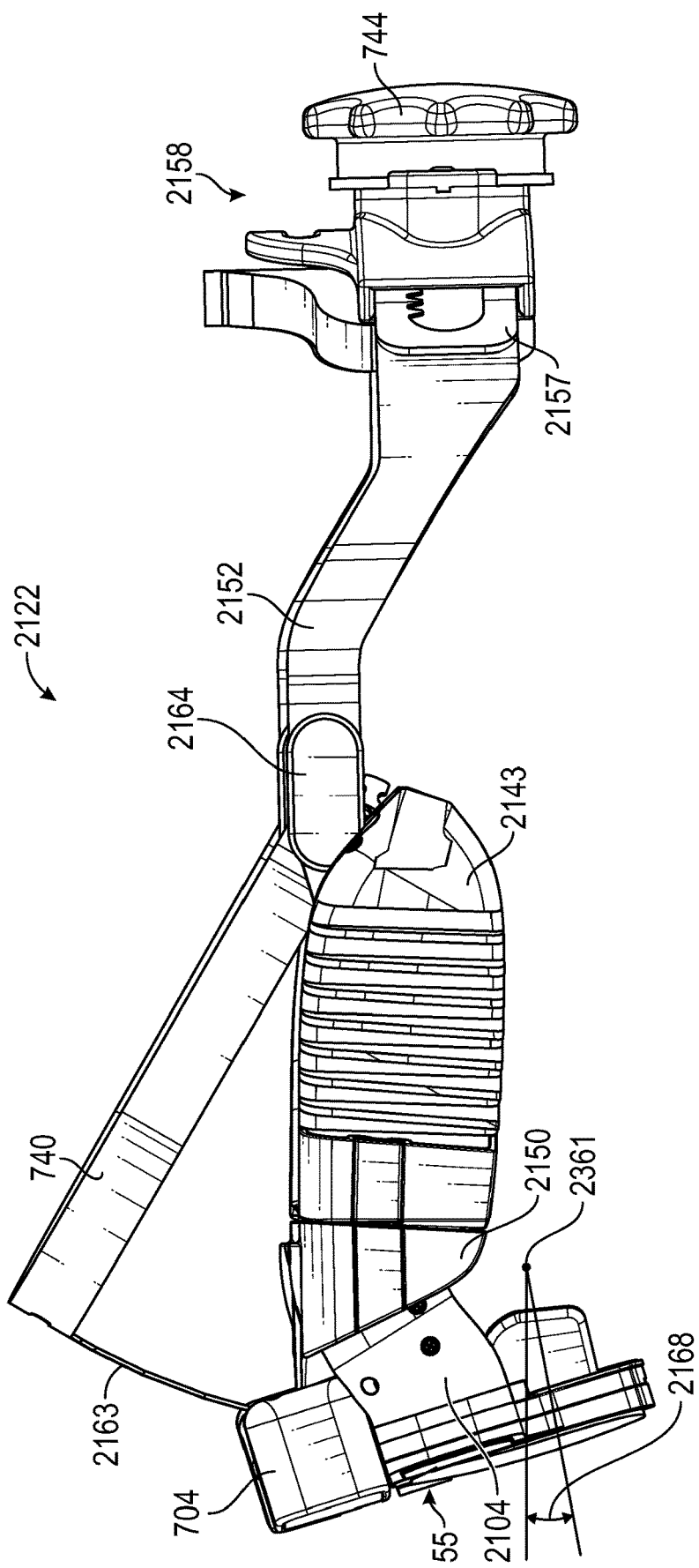
Figure 21D:
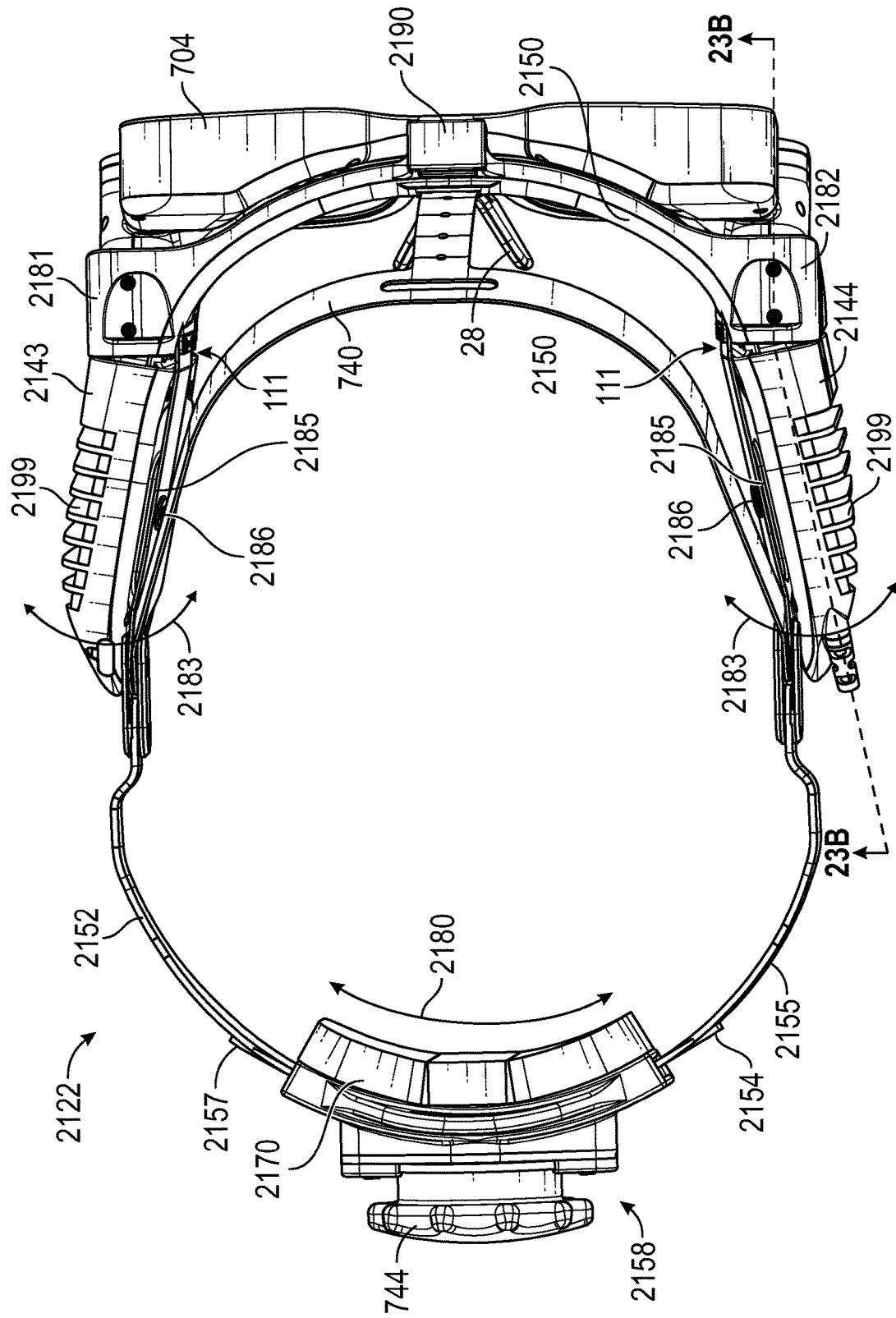

FIG. 21A is a front perspective view of the head-mounted display 2122, FIG. 21B is a rear perspective view of the head-mounted display 2122, FIG. 21C is a left side view of the head-mounted display 2122, and FIG. 21D is a top view of the head-mounted display 2122. Some similarities of the head-mounted display 2122 to other head-mounted displays disclosed herein include, for example, a head strap 740 and knob 744 for adjusting the head strap 740, similar to in the head-mounted display 700 of FIG. 2B. The head strap 740 can have some additional features, however, in order to accommodate certain differences in the head-mounted display 2122, described in greater detail below.

Other similarities of the head-mounted display 2122 to other head-mounted displays disclosed herein include, for example, an optics housing 704 that comprises one or more cameras 708 and infrared projectors 716 (see FIG. 21A), one or more processors 33, wireless communication devices 45, and/or storage devices 46 (see FIG. 21B), an optical engine 55 that can include the same or similar components as optical engine 55 discussed above with reference to FIG. 3, a plurality of AR displays 49*a*, 49*b* similar to as discussed above with reference to FIG. 3, and an adjustable nose pad 28 similar to as discussed above with reference to FIG. 12. In this embodiment, the optical engine is housed within an optical engine housing or frame 2104. In some embodiments, the optics housing 704 and optical engine housing 2104 are part of the same frame or housing, and in some embodiments, the optics housing 704 and optical engine housing 2104 are separate components. In this embodiment, the optics housing 704 and optical engine housing 2104 are configured to tilt together (see FIG. 23B), but some embodiments may allow the optical engine housing 2104 to tilt or otherwise move with respect to optics housing 704. The optics housing 704, optical engine housing 2104, and the components housed within or attached to those housings (such as, but not limited to, displays 49*a*, 49*b*, and optical engine 55) may be collectively referred to as a see-through display assembly 2349. Further, in any embodiment disclosed herein that includes one or more displays that are configured to tilt using a pantoscopic tilting assembly (PTA), the displays and any other components, frames, and/or housings that tilt along with the displays can be collectively referred to as a see-through display assembly. In some embodiments, optical engine housing or frame 2104 includes some or all of the features of display assembly frame 41 of FIG. 3.

One difference in the head-mounted display 2122 from the head-mounted display 22 of FIG. 2A is that the head-mounted display 2122 comprises a left temple housing 2143 and a right temple housing 2144 instead of a left temple arm 43 and a right temple arm 44. The left and right temple housings 2143, 2144 may incorporate some or all of the same features as left and right temple arms 43, 44 of the head-mounted display 22 of FIG. 2A, such as including an on/off button 39, housing one or more processors 33, wireless communication devices 45, and/or storage devices 46, including a strain relief 47 for a cable, and/or the like. The head-mounted display 2122 is configured to mount to the user's head (e.g., to surgeon 26) differently, however, and the left and right temple housings 2143, 2144 accordingly do not include rocker arms like the head-mounted display 22. Specifically, the head-mounted display 2122 is configured to attach to a user's head using head strap 740. Head strap 740 has similarities to the head strap 740 of head-mounted display 700 of FIG. 2B, but also has some differences, described below.

With reference to FIG. 21B, the head strap 740 of head-mounted display 2122 comprises or consists essentially of a first or left side strap 2152 and a right or second side strap 2155. The left side strap 2152 comprises a first end 2153 that is affixed to a first or left end of a frame 2150, and the right side strap 2155 comprises a first end 2156 that is affixed to a second or right end of the frame 2150 (see FIG. 21A). The first or left end 2150 is configured to be positioned adjacent a first or left temple of a user (e.g., surgeon 26), and the second or right end 2150 is configured to be positioned adjacent a second or right temple of a user (e.g., surgeon 26). The left side strap 2152 further comprises a second end 2154, and the right side strap 2155 further comprises a second end 2157. As discussed in greater detail below, an adjustment mechanism 2158 can be used to adjust the relative positions of the second ends 2154, 2157, in order to adjust a circumferential size of the head strap 740. The adjustment mechanism 2158 and head strap 740 can together be referred to as an adjustable strap assembly.

With further reference to FIG. 21B, the head strap 740 further comprises a forehead support 2160 that comprises a strap extending from a first end 2161 that is pivotably coupled to the left side strap 2152 to a second end 2162 that is pivotably coupled to the right side strap 2155. The forehead support 2160 further comprises a central support 2163 extending down from the main strap and affixed to a middle or central location of the frame 2150. Although not shown in these figures, cushioning or padding may be added to any portion of the head strap 740, including to the forehead support 2160 and elsewhere. An example of such cushioning or padding is discussed below with reference to FIGS. 25 and 26A-26C.

With continued reference to FIG. 21B, in this embodiment, the left and right side straps 2152, 2155 each comprise a front portion 2165 that is pivotably coupled to a rear portion 2166 by a connector 2164. Further, in this embodiment, the front portions 2165 are pivotably connected at the same pivotal connection as the first and second ends 2161, 2162 of the forehead support 2160 strap. Such a configuration is not required, however, and various other embodiments may include more or fewer pivotal connections, or may not include pivotal connections. The pivotal configuration shown in FIG. 21B has been found to be desirable, however, in order to accommodate various users (e.g., surgeons 26) while comfortably and securely maintaining the head-mounted display 2122 on the user's head.

The head strap 740 also desirably comprises a pad or cushion 2170 attached to the adjustment mechanism 2158 that can engage the back of the user's head. Further, the head strap 740 in this embodiment also comprises a front slot 2171 and a rear slot 2172 that can be used to attach an optional upper or top strap, as described in more detail below with reference to FIGS. 24A-24B.

With reference to FIG. 21C, this figure illustrates that the optical engine housing 2104 and optics housing 704 can desirably pivot or tilt with respect to the frame 2150, in order to adjust pantoscopic tilt angle 2168. Additional details of the mechanism used for adjusting the pantoscopic tilt angle 2168 in head-mounted display 2122 are provided below with reference to FIG. 23B. Additionally or alternatively, the same or similar tilting mechanism may be used as described above, such as with reference to FIGS. 13 and 14.

With reference to FIG. 21D, this top view of the head-mounted display 2122 helps to show certain adjustability produced by the adjustment mechanism 2158. Specifically, the adjustment mechanism 2158 desirably adjusts a circumferential size defined essentially by the left side strap 2152, the right side strap 2155, and the frame 2150. For example, if the adjustment mechanism 2158 causes the ends 2154, 2157 to become closer together, then the circumferential size will increase, and if the adjustment mechanism 2158 causes the ends 2154, 2157 to become further part, then the circumferential size will decrease. Arrow 2180 represents this increasing or decreasing in circumferential size.

With continued reference to FIG. 21D, this figure also shows that the left temple housing 2143 and right temple housing 2144 can desirably move or pivot inward and outward with respect to the ends 2181, 2182 of the frame 2150. This movement or pivoting is indicated by arrows 2183. The movement 2183 of the temple housings 2143, 2144 can be a result of a combination of adjustments to the circumferential size of the head strap 740 and flexing of the head strap 740 as a user installs the head-mounted display 2122 onto their head or removes the head-mounted display 2122 from their head. The movement or pivoting may be facilitated by the same or similar tilting assembly 111, as discussed above with reference to FIG. 9.

In order to assist with the adjustability of the head-mounted display 2122 and its head strap 740, the left and right temple housings 2143, 2144 can also desirably be movably coupled to a portion of the head strap 740. For example, in this embodiment, the left temple housing 2143 is slidably coupled to the left side strap 2152, and the right temple housing 2144 is slidably coupled to the right side strap 2155. More specifically, each of the temple housings 2143, 2144 desirably comprises or consists essentially of a follower 2185 that is slidable forward and backward, and that is affixed to the left or right side strap 2152, 2155 by one or more fasteners, such as fastener 2186. Further details of this structure are described below with reference to FIGS. 23A-23D.

FIGS. 21A and 21D also show that the head-mounted display 2122 comprises a cover 2190 that is removably coupled to the frame 2150. Desirably, this cover 2190 may be removed and replaced with a detachable flashlight assembly, such as is described in greater detail below, with reference to FIGS. 27A-27D and 28A-28F.

With reference to FIG. 21D, this figure also shows that each of the temple housings 2143, 2144 can comprise a plurality of fins 2199 (e.g., heat-dissipation fins) which can, for example, help with heat dissipation. Various other heat dissipation features may also or alternatively be used, including vents, heatsinks, fins, protrusions, active and/or passive cooling, and/or the like. Such features may be desirable, such as to dissipate heat generated by, for example, one or more processors 33 located within one or both of the temple housings 2143, 2144.

This particular configuration of HMD 2122 is shown by way of example, in order to illustrate certain problems that are addressed by certain embodiments and to demonstrate the application of these embodiments in enhancing the performance of such a system. Embodiments of the disclosure, however, are by no means limited to this specific sort of example HMD configuration, and the principles described herein may similarly be applied to other sorts of HMDs and HUDs used in any suitable types of near-eye display AR-based image-guided surgical systems. HMD 2122 may be used in non-medical applications. For example, non-medical applications may involve consumer or commercial applications such as athletics and fitness, gaming, driving, product design, navigation, manufacturing, logistics, shopping and commerce, educational training, remote collaboration, etc.

Example Adjustment Mechanism Details

Figure 22A:
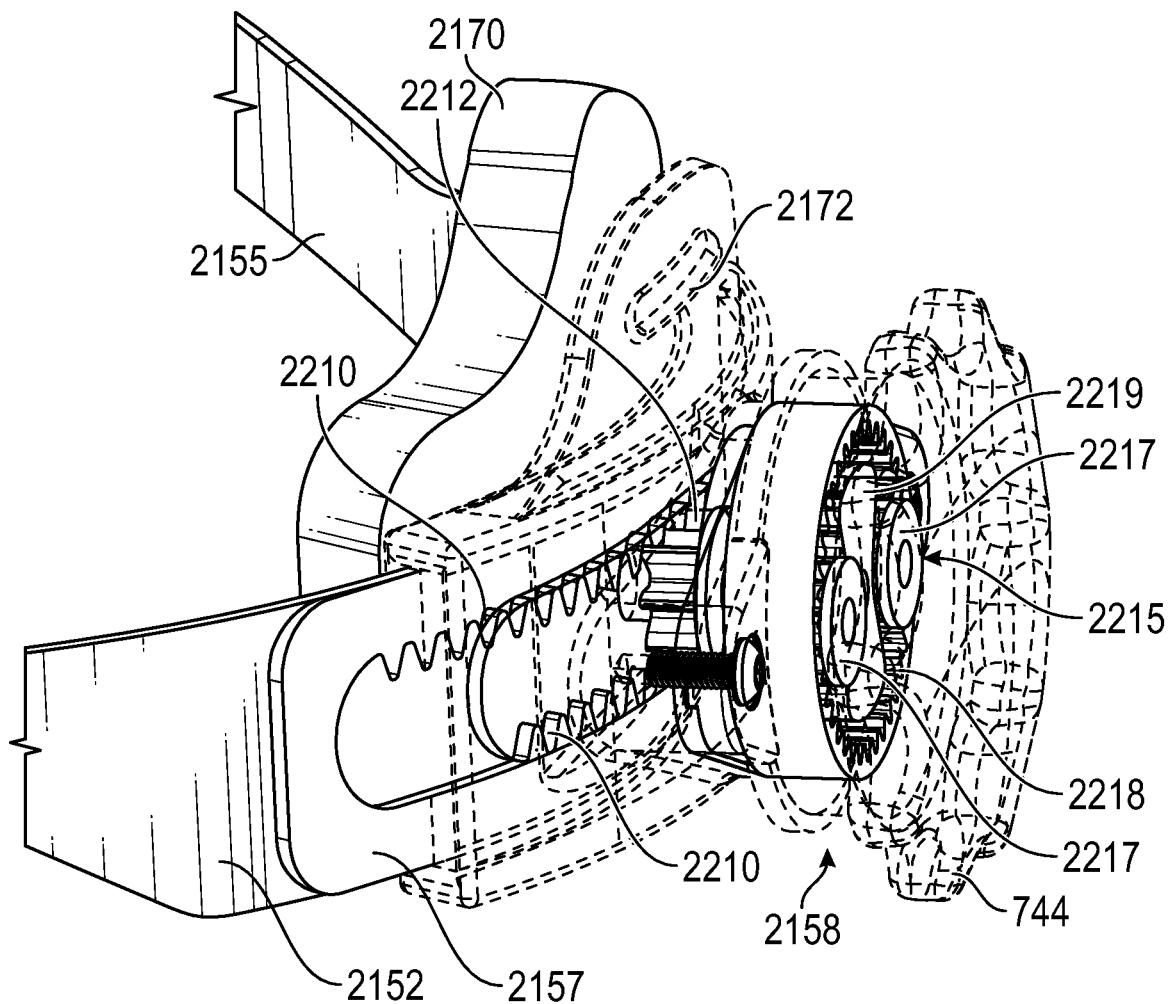
FIGS. 22A-22B and 23A-23D illustrate additional details of adjustment mechanisms of the head-mounted display of FIG. 21A.
Figure 22B:
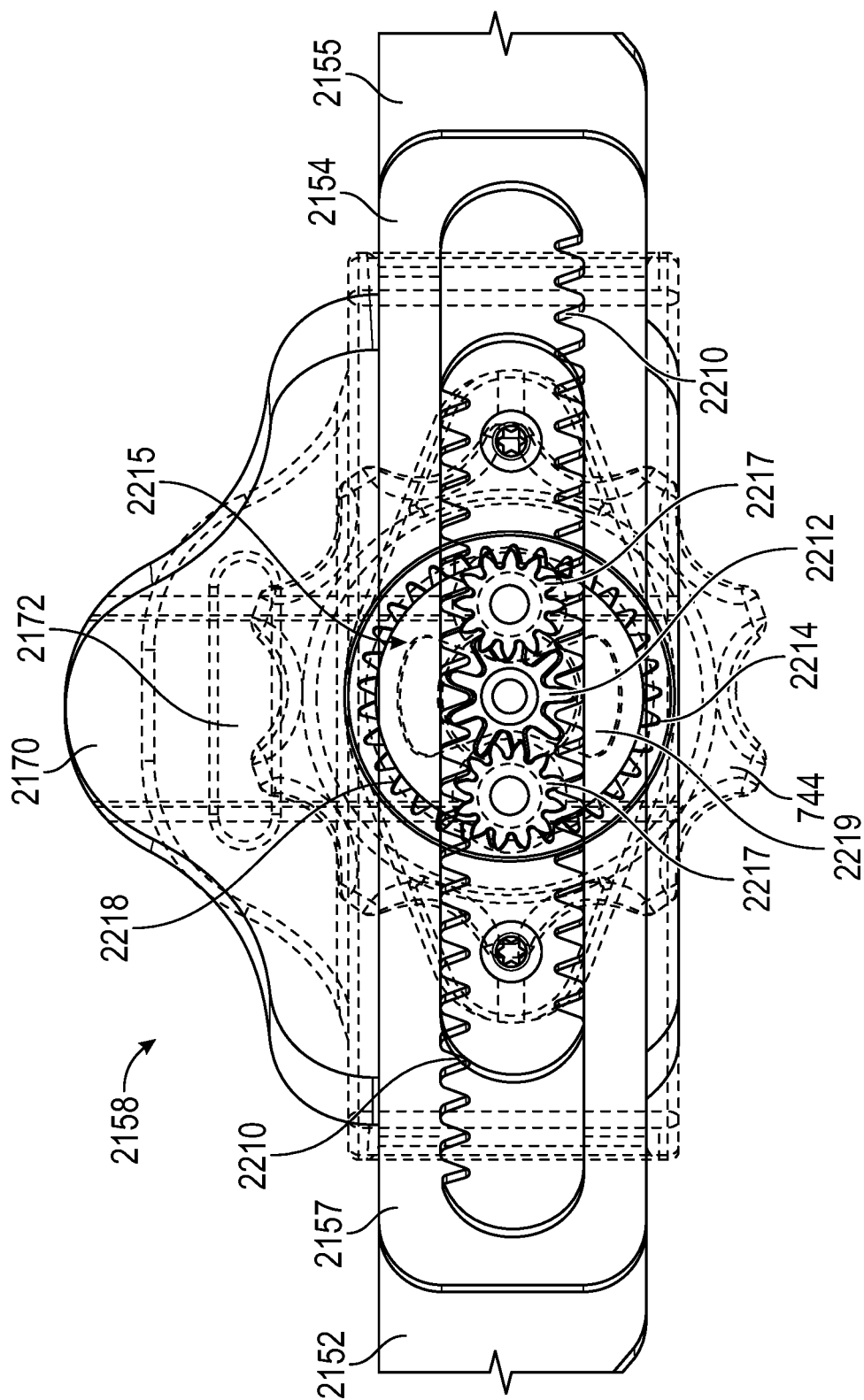

FIGS. 22A and 22B illustrates additional detail of the adjustment mechanism 2158 that can be used to adjust a size of the head strap 740 of head-mounted display 2122. Additionally, FIGS. 23A-23D illustrate additional details of the follower mechanism that assists in controlling the inward and outward pivoting 2183 of the left and right temple housings 2143, 2144 (see FIG. 21D). These figures also illustrate additional details of the pantoscopic tilting mechanics.

As discussed above, the head-mounted display 2122 can desirably be configured to be usable by users (e.g., surgeons 26) having a variety of head sizes and/or shapes. Accordingly, the head strap 740 can desirably be adjustable, such as to adjust a circumferential size of the head strap 740 to accommodate heads of the users having various shapes and sizes. In order to make the head-mounted display 2122 more comfortable for a user and to better accommodate users having differently sized and/or shaped heads, in addition to adjusting the circumferential size of the head strap 740, the left and right temple housings 2143, 2144 can desirably be movably or pivotably coupled to a frame 2150 (as discussed above with reference to FIG. 21D). Accordingly, when the head strap 740 is adjusted to be smaller (e.g. by using knob 744 to reduce the circumferential size of the head strap 740) the left and right temple housings 2143, 2144 can desirably pivot inward (e.g., in a direction towards the user's head) with respect to the frame 2150. Likewise, when the head strap 740 is adjusted to be larger (e.g., by using knob 744 to increase the circumferential size of the head strap 740) the left and right temple housings 2143, 2144 can desirably pivot outward (e.g., in a direction away from the user's head) with respect to the frame 2150. Such pivoting may also occur as a user installs or removes the head-mounted display 2122.

FIGS. 22A and 22B illustrate additional details of how the knob 744 of the adjustment mechanism 2158 causes the change in circumferential size of the head strap 740 (see, e.g., adjustment 2180 of FIG. 21D). Specifically, in this embodiment, each of the side straps 2152, 2155 comprises a rack 2210 that engages a pinion or pinion gear 2212. In this embodiment, there is a single pinion gear 2212 that rotates with the knob 744 and that engages both of the racks 2210. In some embodiments, however, there may be separate pinion gears, with each pinion gear engaging one of the racks 2210. Rotation of the knob 744, and thus the pinion gear 2212, desirably causes the ends of the straps 2157, 2154 to move closer together or further apart, thus changing the circumferential size of the head strap.

In order to maintain the circumferential size of the head strap in a particular configuration, the adjustment mechanism 2158 further comprises a tension mechanism (e.g., stop mechanism) 2215. The tension mechanism 2215 is configured to maintain the knob 744 in a particular position until, for example, a user overcomes a threshold force of the tension mechanism 2215 in order to rotate the knob 744. For example, the tension mechanism 2215 shown in FIGS. 22A and 22B comprises a gear 2218 on an inside surface of the knob 744, with the gear 2218 engaging two other gears 2217. Further, a tension member 2219 is positioned between the gears 2217 and applies friction to the gears 2217 in order to inhibit or restrict their rotation until a threshold force is overcome. It should be noted that the tension mechanism 2215 shown in FIGS. 22A and 22B is merely one example, and various other techniques may be used to maintain the adjustment mechanism 2158 in a particular configuration until a user wishes to adjust the configuration. For example, other ways to generate friction may be used, a separate locking mechanism may be used, a gearing assembly that includes a mechanical advantage that is configured to be self-locking may be used, and/or the like.

It should be noted that this is merely one example of how an adjustment mechanism can work, and various other ways of adjusting the size of the head strap 740 may be used. For example, the left and right side straps 2152, 2155 may be adjusted and then held in place with respect to each other using a different type of geartrain or gearing mechanism, friction, and/or the like.

Figure 23A:
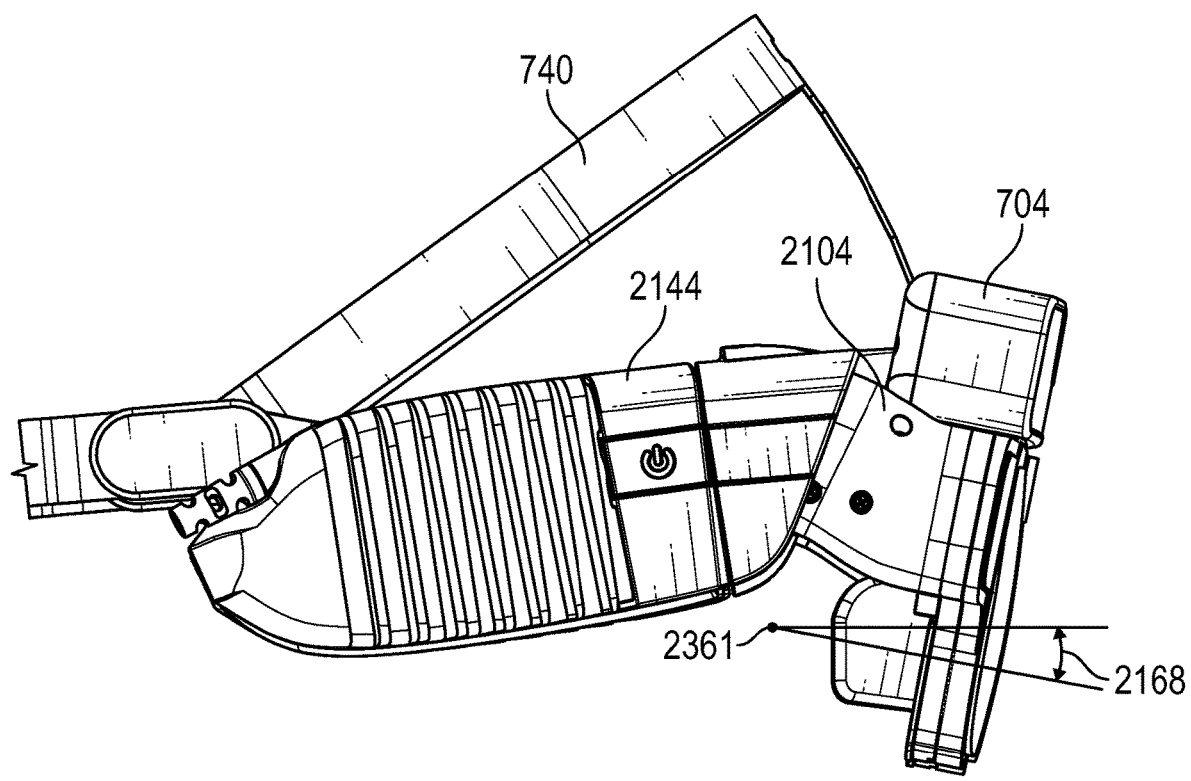
Figure 23B:
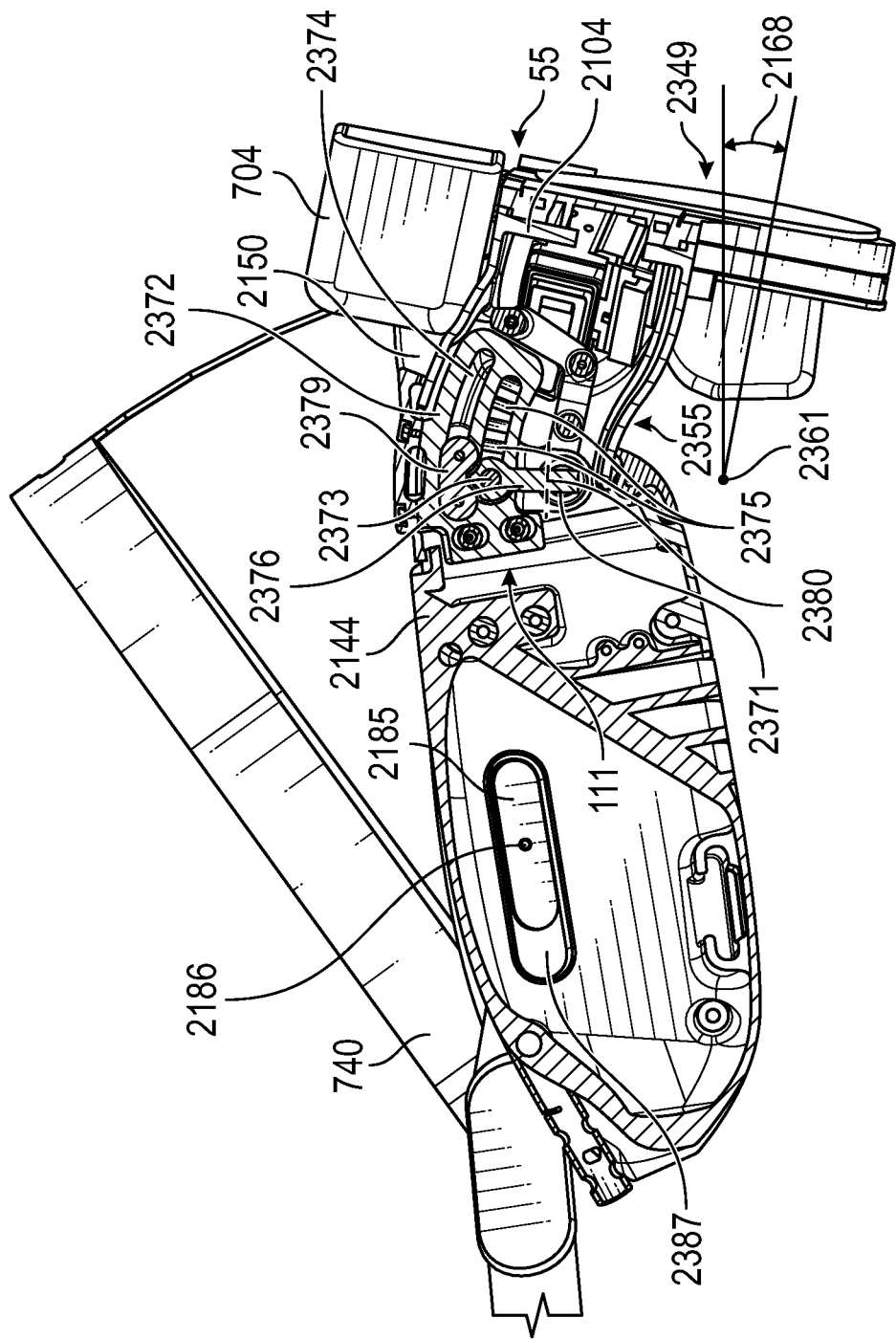

Turning to FIGS. 23A-23D, these figures illustrate additional details of the follower mechanism and tilting mechanism. Specifically, with reference to FIGS. 23B-23D, these figures illustrate additional details of the follower 2185 and fastener 2186 discussed above with reference to FIG. 21D. These figures illustrate the right temple housing 2144, and the same or similar features may be used in the left temple housing 2143. As can be seen in FIG. 23B, the follower 2185 desirably comprises or consists essentially of an elongate protrusion that is slidably coupled to an elongate slot 2387 in a side wall of the temple housing 2144. As discussed above, when the head strap 740 is adjusted and/or flexed, the follower 2185 can desirably slide with respect to the temple housing 2144, thus allowing the temple housing 2144 to move inward or outward with the head strap 740, while still being sufficiently vertically supported by the head strap 740.

Figure 23C:
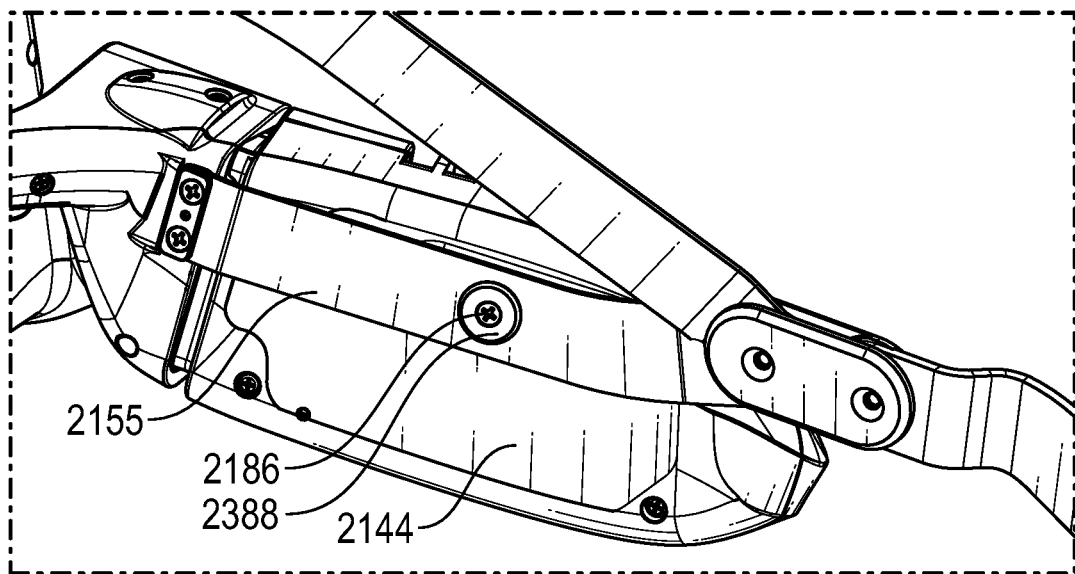
Figure 23D:
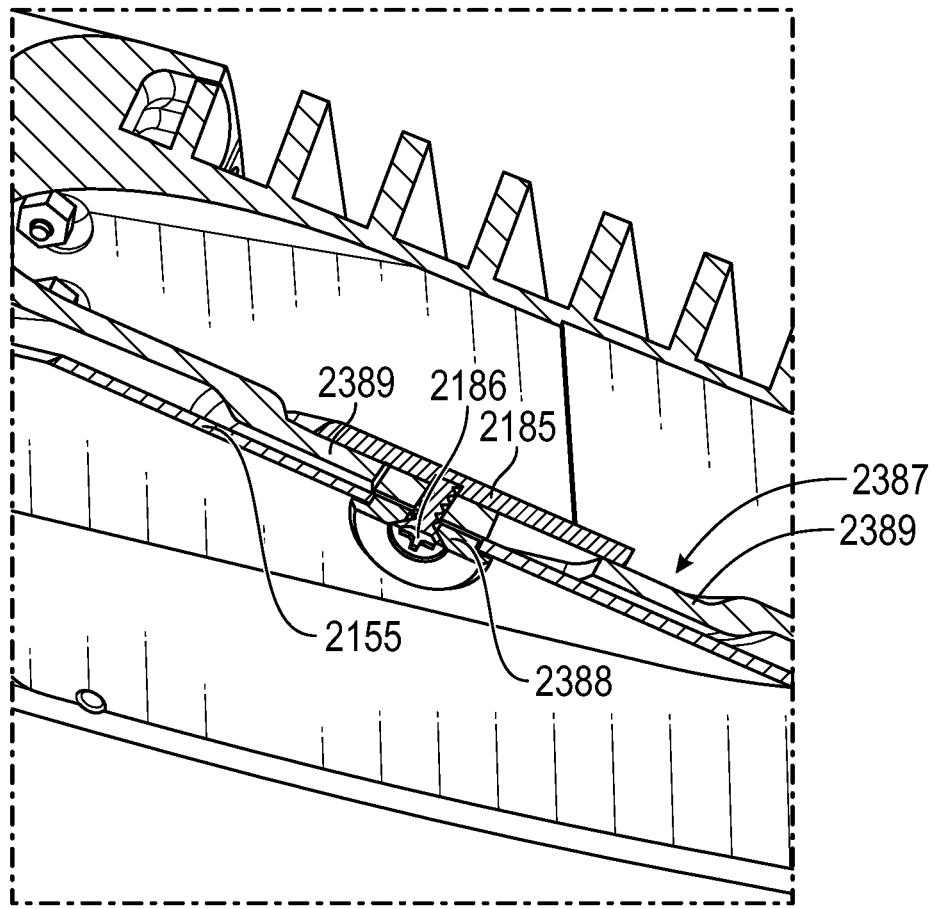

Turning to FIGS. 23C and 23D, these figures show additional details of how the follower 2185 is coupled to the side strap 2155 and temple housing 2144. Specifically, a fastener 2186 and a cap or washer 2388 affix the follower 2185 to the side strap 2155. Further, the wall of the temple housing 2144 desirably comprises a portion 2389 that is positioned between the elongate protrusion of the follower 2185 and the strap 2155, thus retaining the follower 2185 in position with respect to the temple housing 2144.

It should be noted that this is merely one example way of movably or slidably mounting a temple housing to a side strap, and other techniques may also be used. Desirably, the temple housings are supported by the side straps in a generally vertical direction while being free to move in a generally horizontal direction with respect to the side straps. Such a configuration can lead to adequate vertical support of the temple housings by the head strap 740 while allowing adjustments for a comfortable and snug fit on the user's head.

Returning to FIG. 23B, this figure also illustrates additional details of a pantoscopic tilting assembly (PTA) 2355 that enables tilting (e.g., rotating, pivoting, moving, or sliding) of the optical engine housing 2104 and optical housing 704 with respect to the frame 2150. The PTA 2355 performs a similar function to the PTA 155 and PTA 156 discussed above with reference to FIG. 14, and the same or similar reference numbers are used to refer to same or similar components. Further, any of the other PTA's disclosed herein, including but not limited to PTA 156 and PTA 155, may be incorporated into the head-mounted display 2122, and the PTA 2355 of head-mounted display 2122 may be incorporated into any of the other head-mounted displays disclosed herein.

The PTA 2355 comprises or consists essentially of a virtual hinge or axis (represented by point 2361), created by arc-shaped slot 2374 as a radial cam, and rotatable section or guide member 2379 as a follower, about which optical engine housing 2104 and housing 704 can pivot (e.g., tilt, rotate, move, or slide) with respect to the frame 2150, thus causing adjustment to the pantoscopic tilt angle 2168. The center of the virtual hinge or axis 2361 is desirably located at the center of the human eyeball (e.g., eyeball 158 of FIG. 13), so that movements of the portable or movable parts (e.g., of optical engine housing 2104 and housing 704) about or with respect to the stationary parts (e.g., frame 2150 and part 2372 of the frame 2150 that defines the slot 2374) maintain undistorted vision on the optical engine displays (e.g., display 49a of FIG. 21A). In order to maintain the optical engine housing 2104 and housing 704 at a particular tilt angle or position with respect to the frame 2150, the PTA 2355 further comprises a locking element 2373. In this embodiment, the locking element 2373 comprises a spring-loaded ball that can engage any one of a plurality of detents 2375 that are fixed with respect to the frame 2150, in order to maintain the optical engine housing 2104 and housing 704 (and other parts of the see-through display assembly 2349 that tilt along with housing 2104 and housing 704) in any one of a plurality of predefined positions corresponding to the plurality of detents 2375. Specifically, in this embodiment, the ball 2373 is coupled to an arm 2376 that is configured to pivot about axis 2380 (with axis 2380 being parallel to the plane of this drawing, and thus the pivoting action of the arm 2376 being into or out of the page). Further, the arm 2376, and thus also the ball 2373, is spring-loaded about the axis 2380 using, for example, a spring 2371 (positioned underneath a lower end of the arm 2376 in this cross-sectional view). When a user (such as surgeon 26) wishes to rotate the optical engine housing 2104 and optical housing 704 with respect to the frame 2150, the user may apply a force to the optical engine housing 2104 and/or housing 704 that causes the rotatable section 2379 to transfer the force to the locking element 2373 through the arm 2376. Once a sufficient force is applied to overcome a threshold force of the spring-loaded ball, the locking element 2373 may disengage one of the detents 2375 of the frame 2150 and allow the optical engine housing 2104 to pivot about the virtual axis 2361 with respect to the frame 2150. Once the optical engine housing 2104 is at the desired pantoscopic tilt angle 2168, the locking element 2373 can maintain the optical engine housing 2104 at that angle by re-engaging one of the detents 2375. The optical engine housing 2104 will desirably then be maintained at that angle with respect to the frame 2150 until the threshold force of the spring-loaded locking element 2373 is again exceeded. Although FIG. 23B illustrates the PTA 2355 of only the right side of head-mounted display 2122, the same or similar structures may also be used on the left side of head-mounted display 2122.

Various modifications to the pantoscopic tilting assembly 2355 may be made. For example, a spring-loaded pin may be used instead of a spring-loaded ball. As another example, the spring-loaded pin or ball may be spring-loaded by a spring that is directly engaged with and/or in line with the ball instead of engaging a lever arm (e.g., arm 2376) that in turn engages the ball. As another example, friction may be used to maintain the optical engine housing 2104 and optical housing 704 at a particular angle with respect to the frame 2150, instead of or in addition to a detent mechanism. Further, the described mechanism (e.g., PTA 2355) is only one example, which in this embodiment implements a virtual axis 2361 with five detents 2375, providing a range of 20° of adjustability (e.g., from 15° to 35° horizontal tilt), although various embodiments may include other ranges of adjustability, as discussed above with reference to FIGS. 15A-15C. Any other virtual axis mechanism can be implemented, such as using friction instead of detents, and/or a totally positive locking mechanism instead of a "semi positive" locking mechanism (like a spring-loaded ball and detents) that unlocks when a threshold force is exceeded. Additionally, some PTAs may utilize a real, or physical, axis (e.g., an axis created by a mechanical hinge) for pivoting instead of a virtual axis. It can be desirable to use a virtual axis, however, such as to reduce or eliminate side field of view limitations and/or obstacles. For example, with reference to FIG. 23B, if the frame 2150 and housing 2104 included mechanical components extending to point 2361 to form a physical hinge at point 2361 (instead of the current virtual axis or virtual hinge at point 2361), those mechanical components may be visible in the surgeon's peripheral vision, and may thus undesirably block some or all of the surgeon's peripheral vision. That said, the disclosure herein is not limited to PTAs that utilize virtual axes, and some embodiments may utilize a physical hinge to form the axis about which the PTA can rotate.

Example Additional Head Strap Features

Figure 24A:
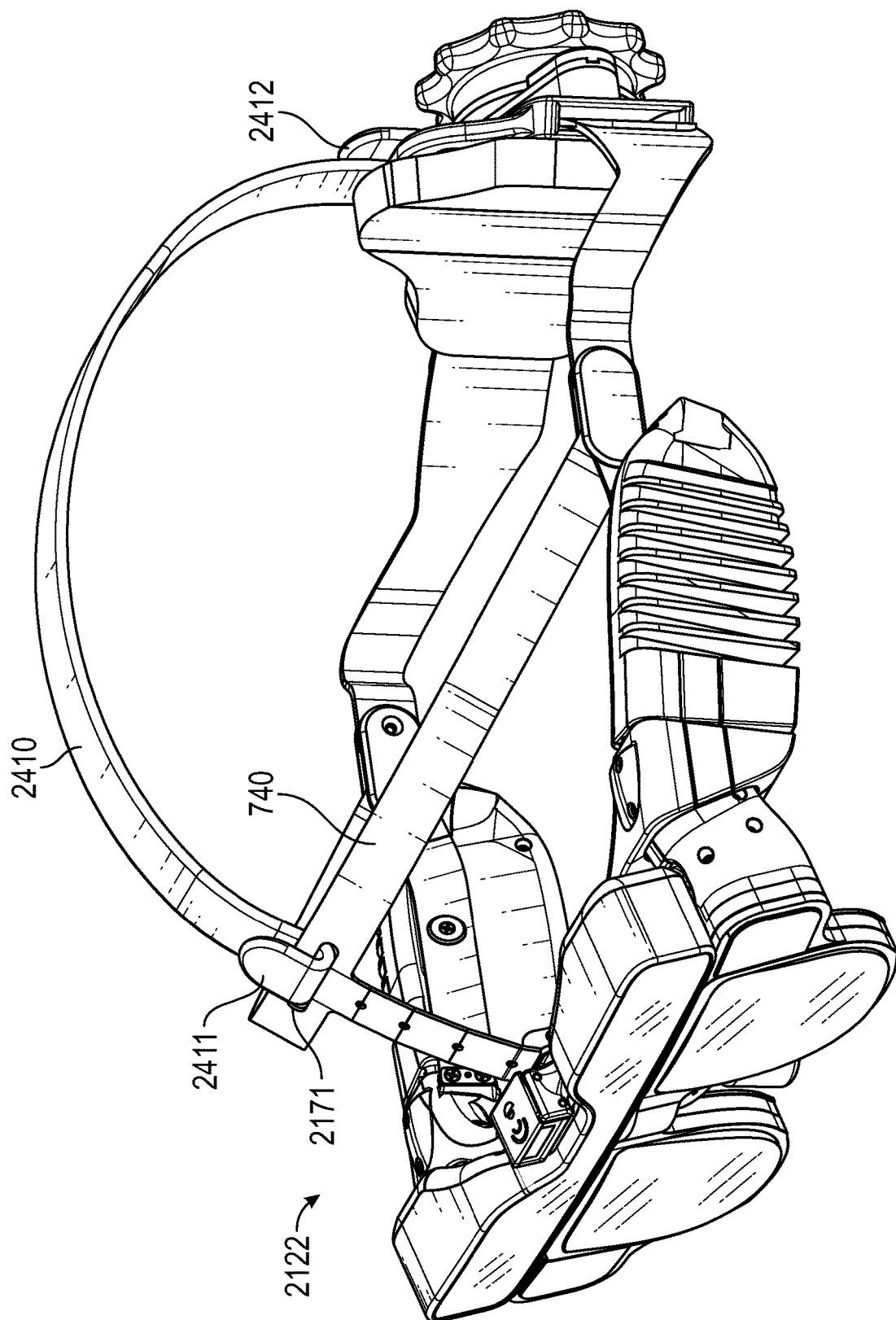
FIGS. 24A-24B, 25, and 26A-26C illustrate embodiments of additional padding and/or straps that may be incorporated into any of the head-mounted displays disclosed herein.
Figure 24B:
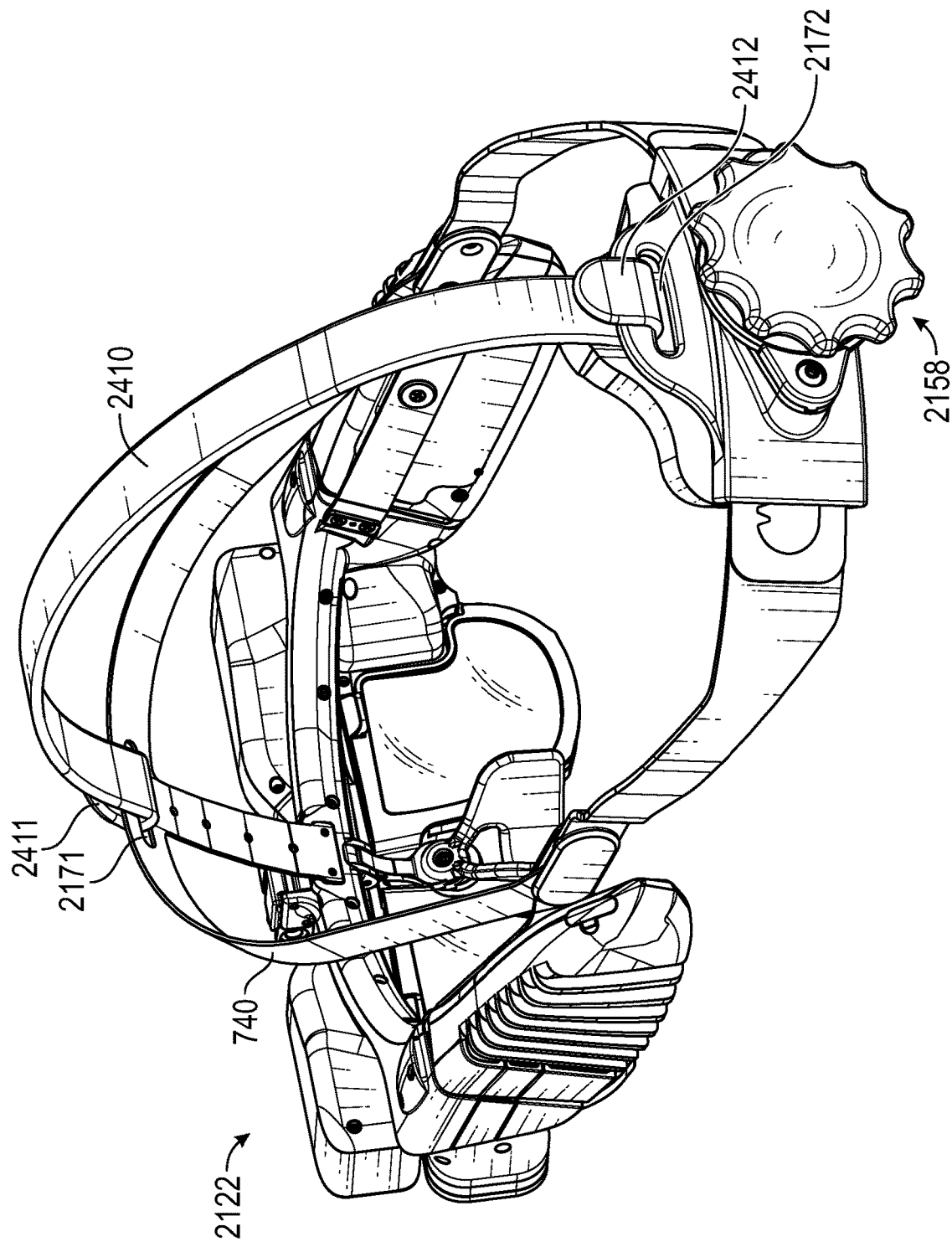

As discussed above with reference to the head-mounted display 2122 shown in FIGS. 21A-21D, the head strap 740 may optionally include a detachable upper or top strap. FIGS. 24A and 24B illustrate the head-mounted display 2122 with such a detachable upper or top strap 2410 coupled thereto. Specifically, the top strap 2410 comprises a first end 2411 that has been passed through slot 2171 and folded back on itself. The first end 2411 may comprise, for example, a hook and loop fastener, a button, and/or the like, that maintains the position of the first end 2411 with respect to the slot 2171. Similarly, the top strap 2410 comprises a second end 2412 that has been passed through slot 2172 and folded back on itself. The second end 2412 may comprise, for example, a hook and loop fastener, a button, and/or the like, that maintains the position of the second end 2412 with respect to the slot 2172.

It can be desirable to have an optional detachable top strap, such as top strap 2410, because some users may prefer to use the head-mounted display 2122 without a top strap, and some users may prefer to use the head-mounted display 2122 with a top strap. That said, some embodiments may include a permanently attached top strap, and some embodiments may not have an option to attach a top strap. It can also be desirable to have the top strap 2410 be adjustable, such as by adjusting a length of the top strap 2410. One way to accomplish this is to allow the amount of the strap at the first and/or second ends 2411, 2412 that is passed through the corresponding slot and folded back on itself to be varied. An additional or alternative way to accomplish this is to include an adjuster in the strap, such as using a buckle, hook and loop fasteners (see, e.g., the description below related to FIGS. 26A-26C), and/or the like. The top strap 2410 may be formed from a variety of materials, such as flexible polymer, fabric, and/or the like. In some embodiments, the top strap 2410 comprises a soft fabric, that can help with comfort, for example.

Figure 25:
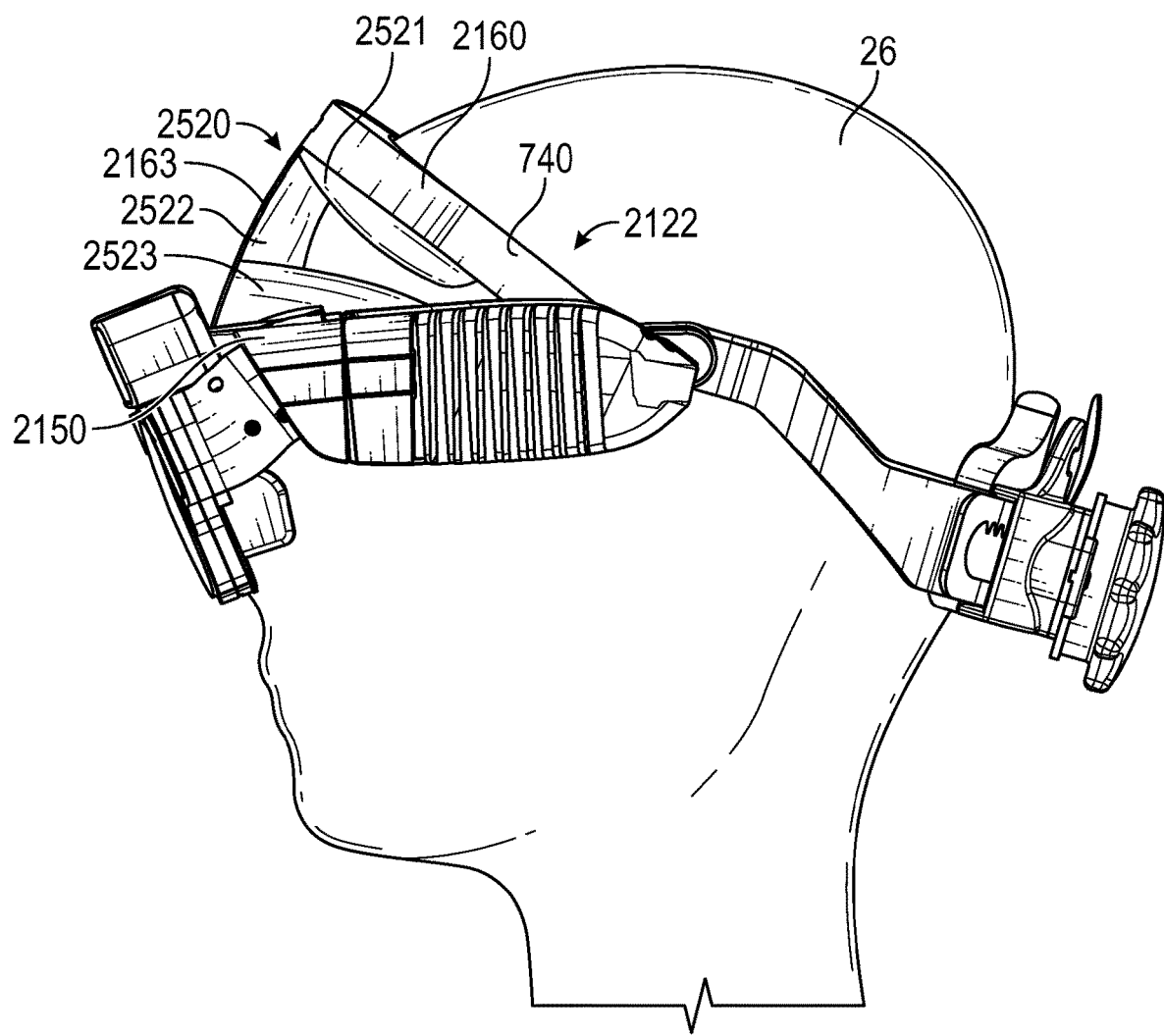

As discussed above, FIGS. 21A-21D illustrate the head strap 740 of head-mounted display 2122 without any padding or cushioning added thereto, other than the rear pad 2170. Turning to FIG. 25, this figure shows an example of the head-mounted display 2122 with a pad 2520 having been added at a front of the head-mounted display 2122, in order to provide some cushion between the head-mounted display 2122 and a forehead of the user (e.g., surgeon 26). Specifically, the pad 2520 in this embodiment includes a first portion 2521 positioned between the main strap of the forehead support 2160 and the surgeon 26, a second portion 2522 positioned between the central support 2163 and the surgeon 26, and a third portion 2523 positioned between the frame 2150 and the surgeon 26.

FIG. 25 illustrates merely one example of cushioning or padding being added to the head-mounted display 2122, and more or less cushioning may be provided, the cushioning may be provided in additional locations, such as along the side straps of the head-mounted display 2122, and/or the like.

Figure 26A:
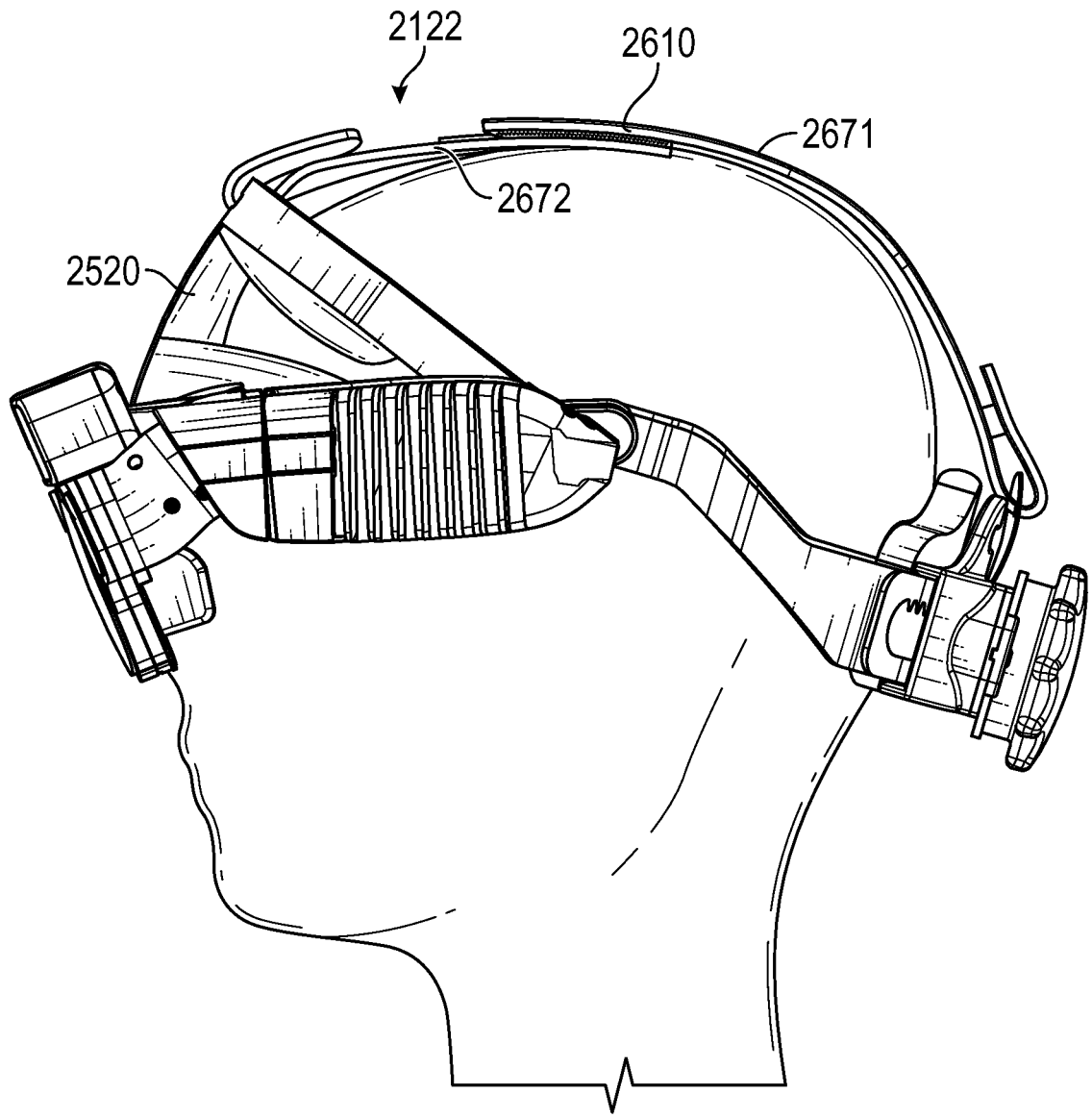
Figure 26B:
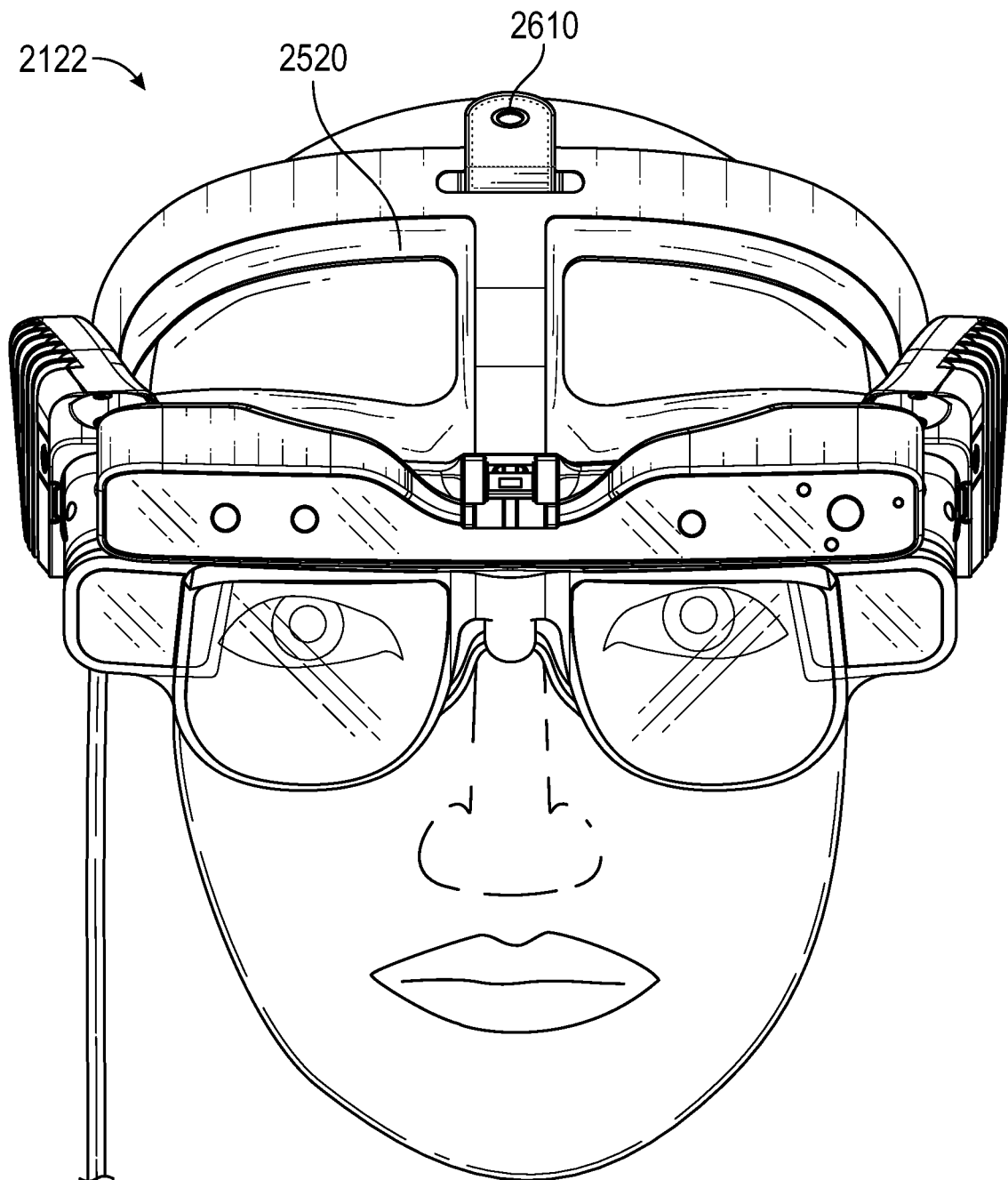
Figure 26C:
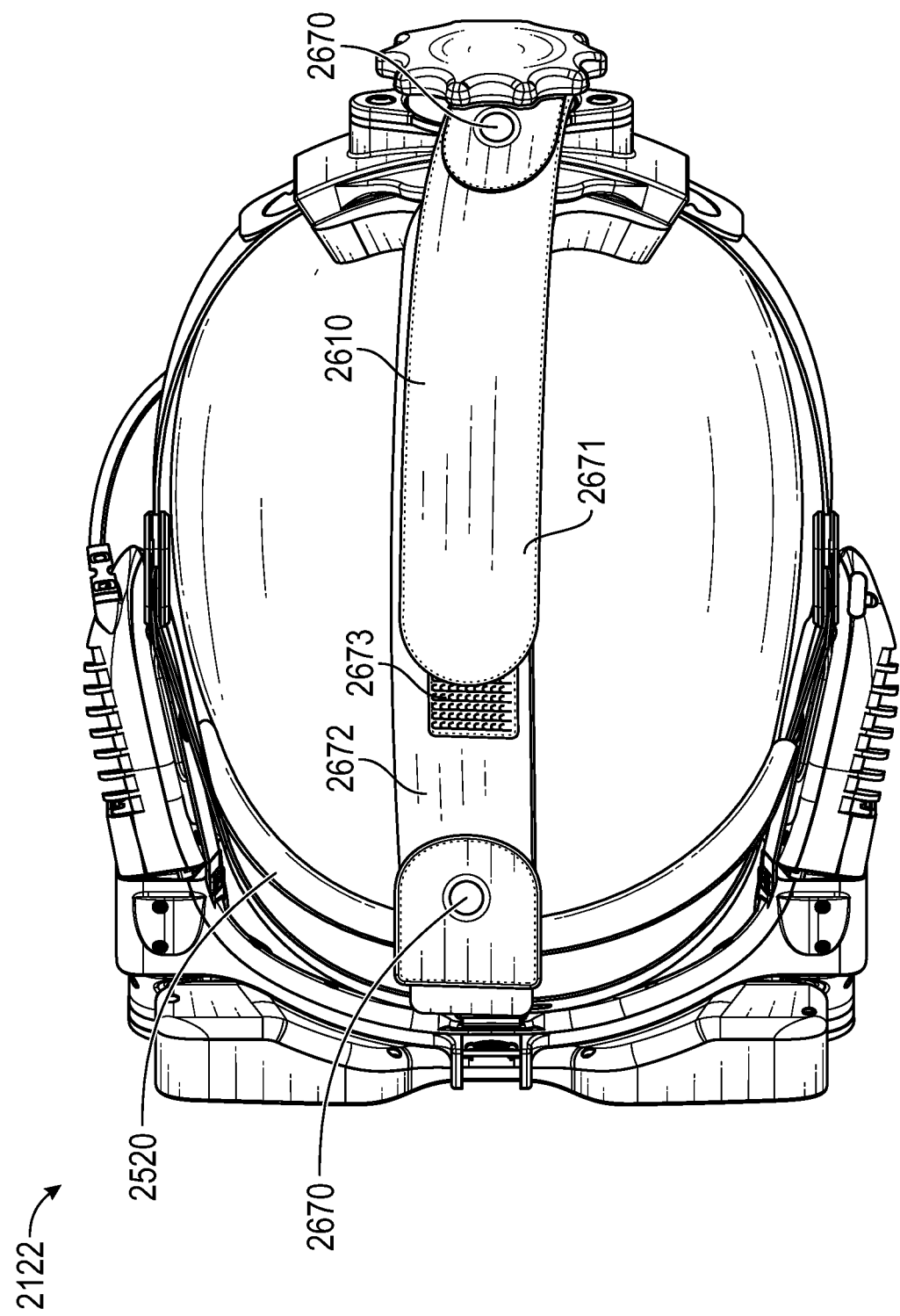

Turning to FIGS. 26A-26C, these figures illustrate the same head-mounted display 2122 of FIG. 25 that has a forehead pad 2520 added, but also has a top strap 2610 added. The top strap 2610 is similar to the top strap 2410 of FIGS. 24A and 24B, except that additional features are shown in FIGS. 26A-26C. Specifically, FIG. 26C shows that each end of the top strap 2610 utilizes a button 2670 to maintain the top strap 2610 in position with respect to the rest of the head-mounted display 2122. Further, FIGS. 26A and 26C show that the top strap 2610 is provided in two parts, namely a rear portion 2671 and a front portion 2672. The rear portion 2671 is laid over the top of the front portion 2672. A hook and loop fastener 2673 desirably maintains the rear portion 2671 in position with respect to the front portion 2672. Such a design can desirably enable the length of the top strap 2610 to be adjusted by, for example, changing the relative position of the rear portion 2671 with respect to the front portion 2672. Although this embodiment desirably uses a hook and loop fastener between the front and rear portions 2672, 2671, other embodiments may use other techniques, such as buttons, a buckle mechanism, elastic, and/or the like.

Additional Example Detachable Lighting Systems

As discussed above, various embodiments of head-mounted displays may include a permanently attached or detachable headlight or lighting system that includes a flashlight, such as to illuminate the area in which a surgical procedure is being performed. Various examples of such lighting systems are described above with reference to, for example, the embodiments of FIGS. 2B, 4, 5, 6, 7, and 8. The head-mounted display 2122 of FIG. 21A, discussed above, may be modified to be used with any of such disclosed lighting systems. Additionally, FIGS. 27A-27D illustrate another example embodiment of a detachable lighting system 2701 in use with the head-mounted display 2122. The detachable lighting system 2701 may also be incorporated into any of the other head-mounted displays disclosed herein.

Figure 27A:
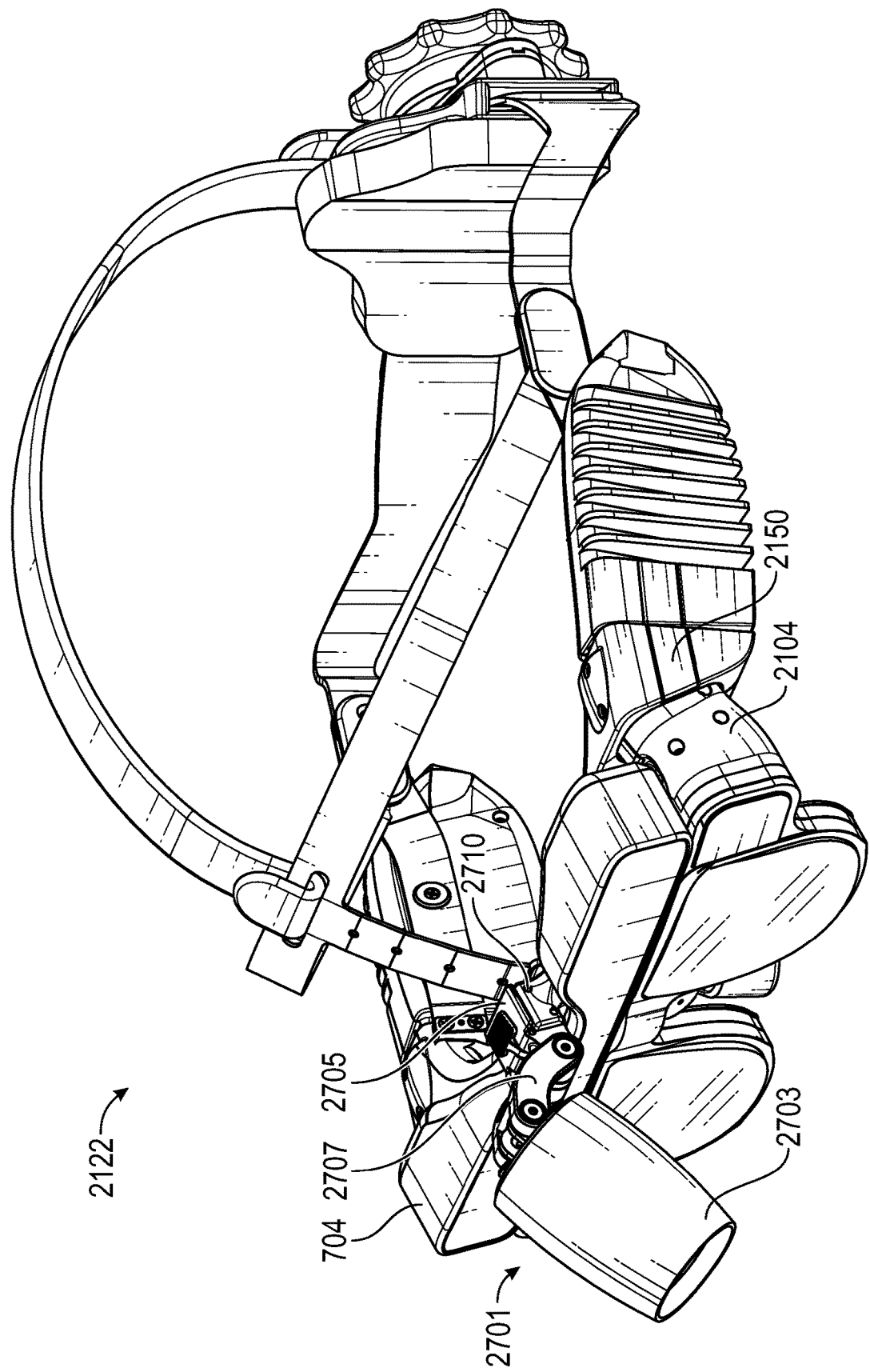
FIGS. 27A-27D illustrate another embodiment of a headlight assembly for use with any of the head-mounted displays disclosed herein.
Figure 27B:
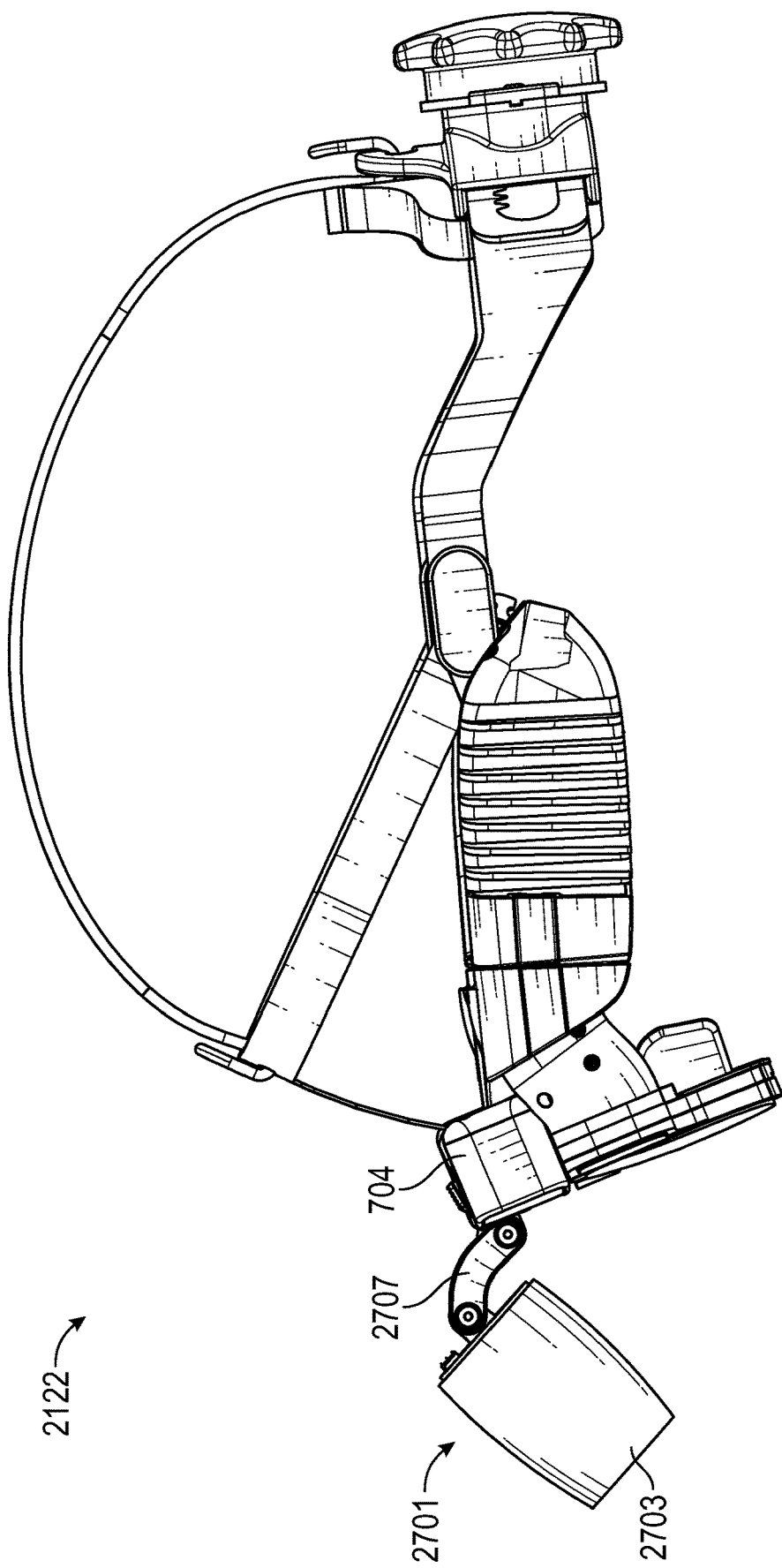

FIGS. 27A and 27B illustrate the detachable lighting system 2701 attached to a mounting socket 2710 of housing 704 of head-mounted display 2122. For example, the removable cover 2190 shown in FIG. 21A has been removed and replaced with mounting base 2705 of lighting system 2701. As can be seen in FIGS. 27A and 27B, the lighting system 2701 comprises or consists essentially of a flashlight 2703 that is pivotably coupled to the mounting base 2705 by an arm 2707. More specifically, the arm 2707 is pivotably coupled at a first end to the flashlight 2703 and at a second end to the mounting base 2705. These pivotal connections desirably allow the flashlight 2703 to be repositioned as needed. For example, in the head-mounted display 2122, the optics housing 704 that incorporates the flashlight mounting socket 2710 will tilt along with the optical engine housing 2104 when the pantoscopic tilt angle of the optical engine housing 2104 is adjusted with respect to the frame 2150. Accordingly, when the pantoscopic tilt angle is adjusted, the orientation of the flashlight 2703 may also change with respect to the frame 2150. In such a case, it may be desirable to reposition the flashlight 2703, such that the flashlight 2703 can be directed toward a same region of interest regardless of the current pantoscopic tilt angle of the optical engine housing 2104. The arm 2707 may be aimed to allow a light beam to be unified with a wearer line of sight for optimal visibility.

Figure 27C:
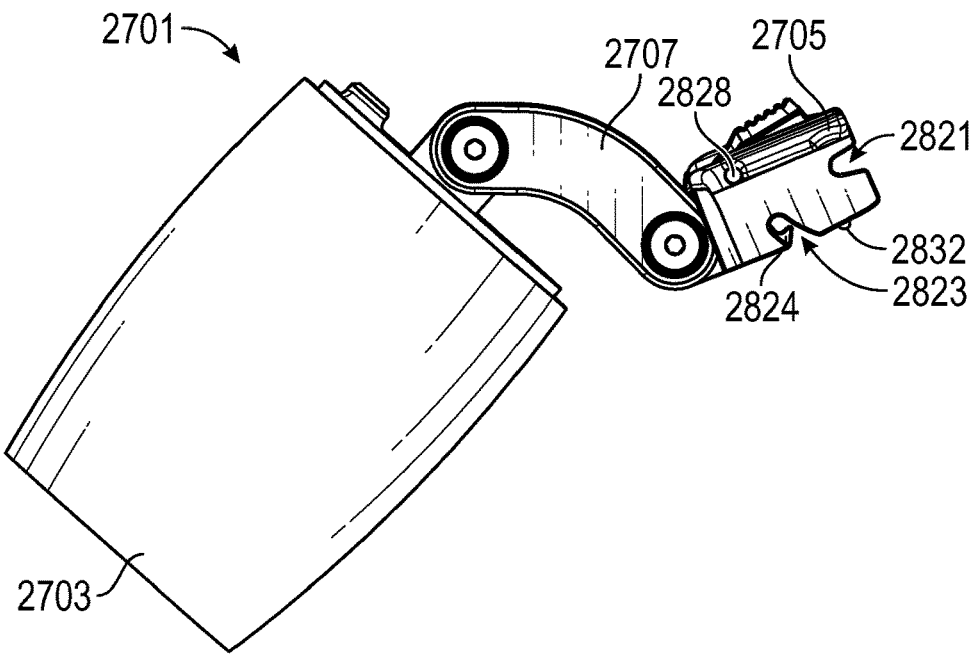
Figure 27D:
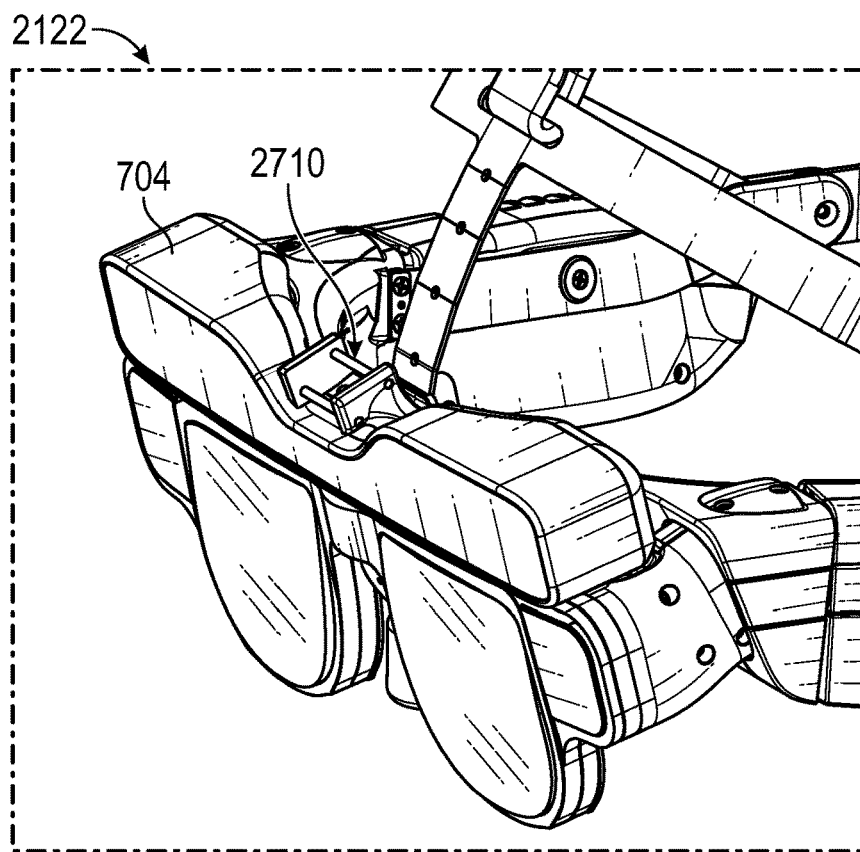

FIG. 27C illustrates a side view of the lighting system 2701 detached from the rest of the head-mounted display. This figure shows more detail of the mounting base 2705, which will be described in further detail below with respect to the embodiment of FIGS. 28A-28F. FIG. 27D illustrates a perspective view of the head-mounted display 2122 with the lighting system 2701 removed. This figure shows more detail of the flashlight mounting socket 2710, which will also be described in further detail below with respect to the embodiment of FIGS. 28A-28F.

Turning to FIGS. 28A-28F, these figures illustrate another embodiment of a lighting system 2801 that can be used with the head-mounted display 2122 (or any other head-mounted displays disclosed herein). The same or similar reference numbers are used as for lighting system 2701 of FIGS. 27A-27D to refer to the same or similar features. The main substantive difference between lighting system 2801 and lighting system 2701 is that lighting system 2801 comprises or consists essentially of two pivotably coupled arms 2707 instead of a single arm 2707. Specifically, with reference to FIG. 28A, the two arms 2707 are pivotably coupled together, with one of the arms 2707 being pivotably coupled to the mounting base 2705, and the other arm 2707 being pivotably coupled to the flashlight 2703. This design can, for example, enable a greater range of adjustability of the position and/or angle of the flashlight 2703 as compared to the lighting system 2701 of FIG. 27A. That said, the single-arm design of lighting system 2701 of FIG. 27A can also be beneficial, particularly if using the single arm 2707 enables a sufficient range of adjustment while reducing weight and/or complexity of the system.

Figure 28A:
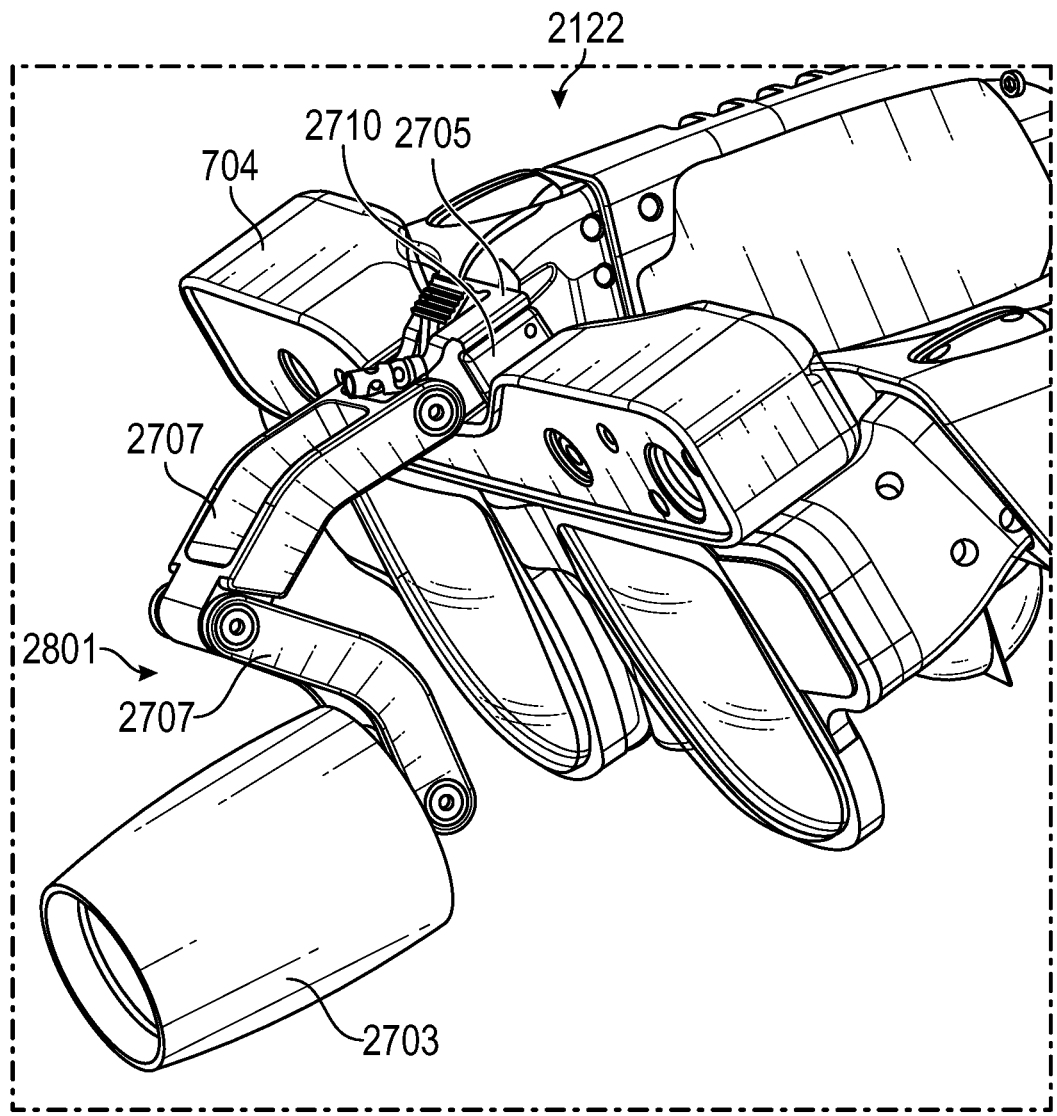
FIGS. 28A-28F illustrate another embodiment of a headlight assembly for use with any of the head-mounted displays disclosed herein.
Figure 28B:
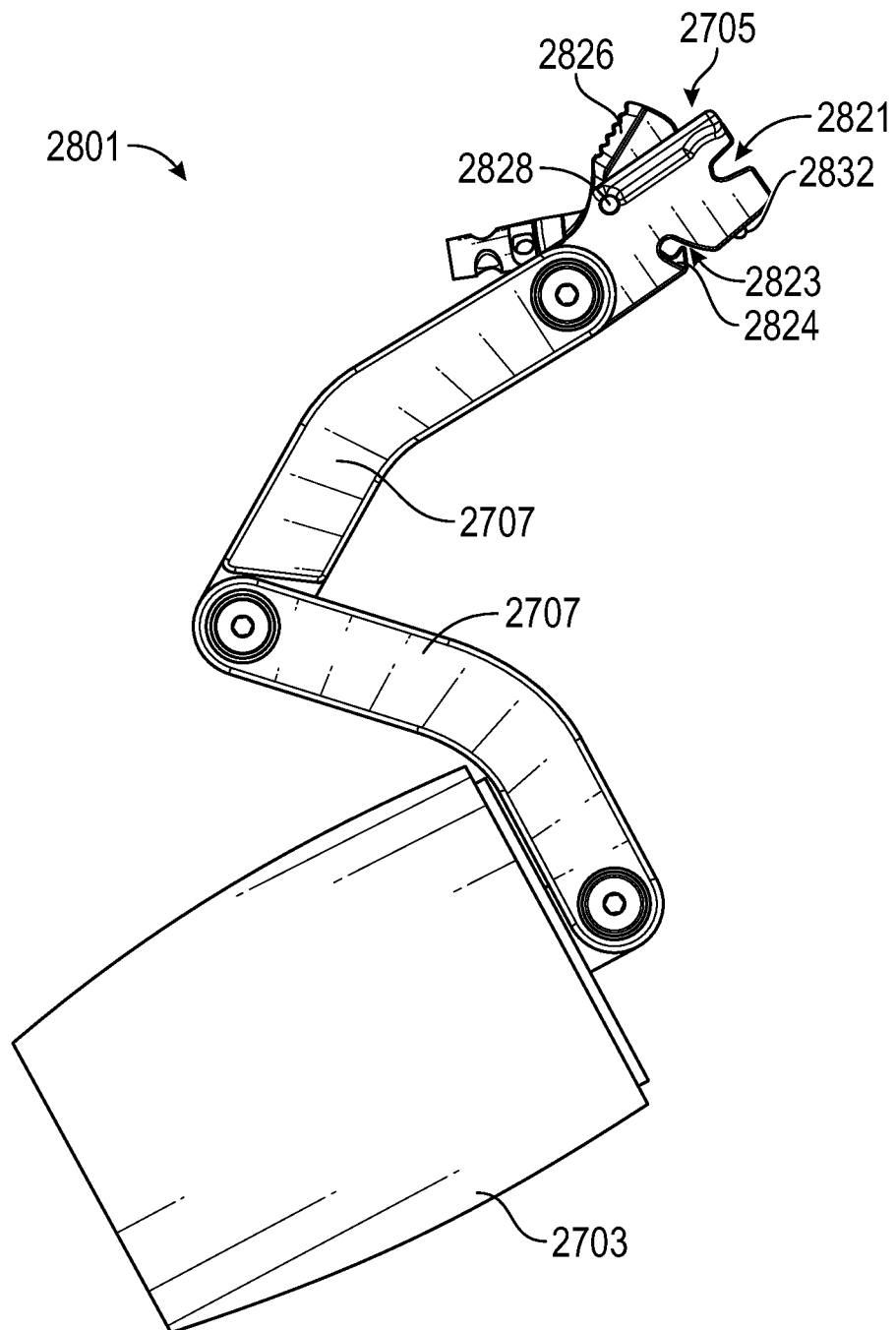
Figure 28C:
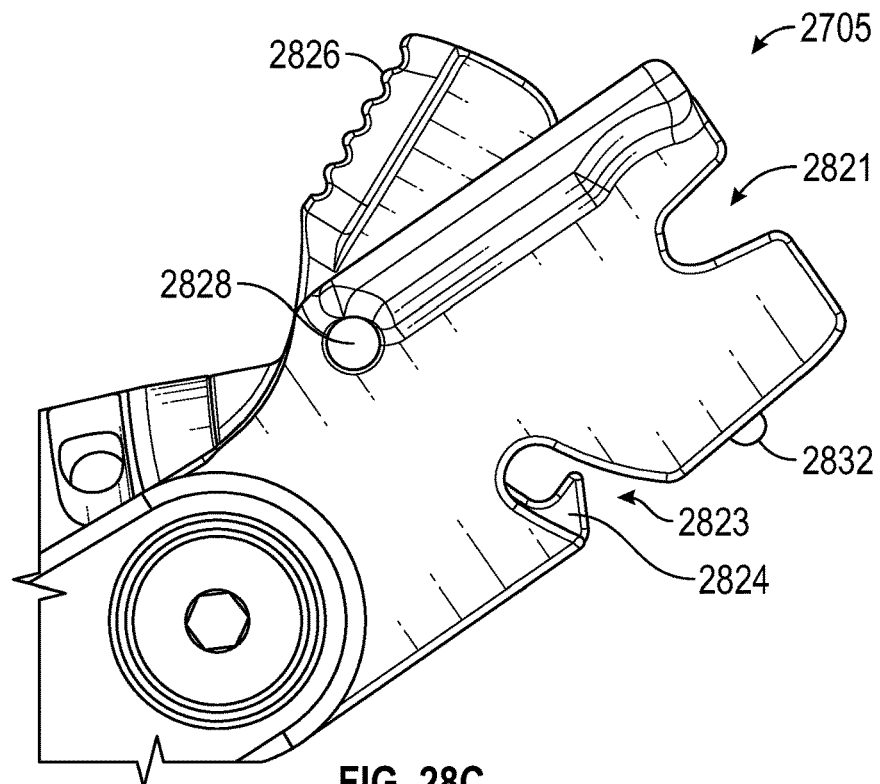
Figure 28D:
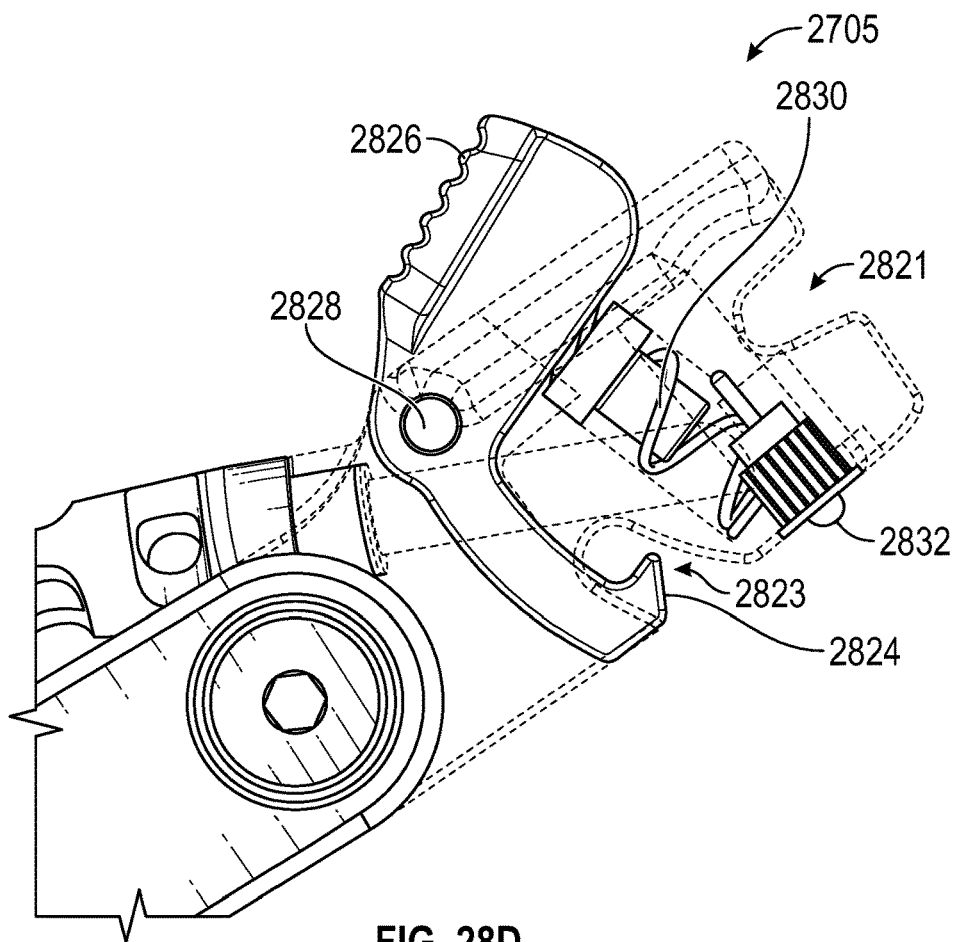
Figure 28E:
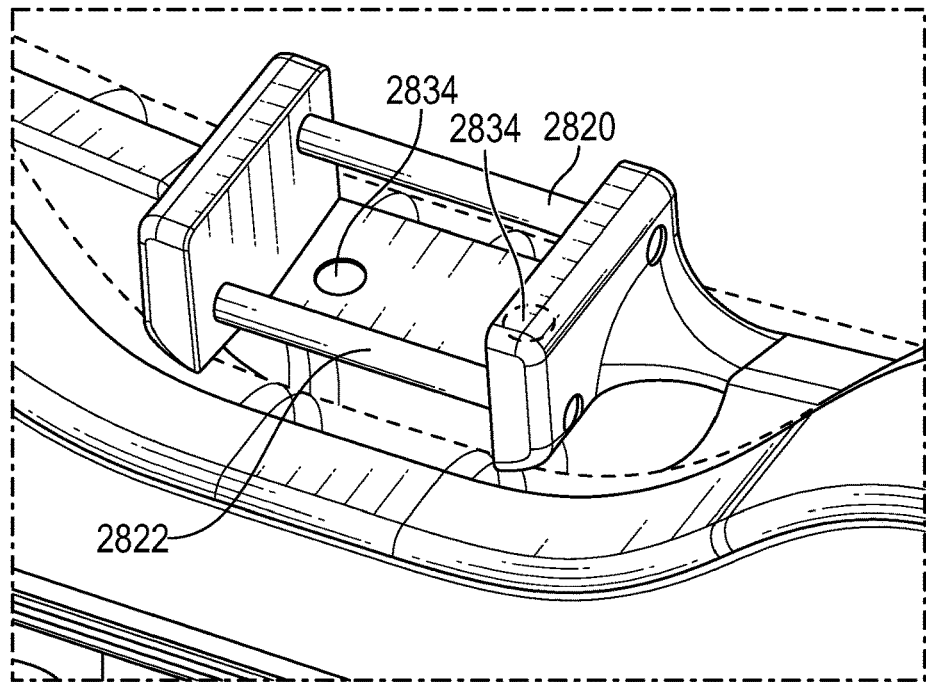

Turning to FIG. 28E, this figure illustrates additional detail of the flashlight mounting socket 2710. Specifically, the flashlight mounting socket 2710 comprises or consists essentially of a first rod 2820 extending generally horizontally, and a second rod 2822 extending generally parallel to the first rod 2020. The flashlight mounting socket 2710 further comprises two electrical contacts 2834 at a base of the socket. The electrical contacts 2834 may, for example, be used to provide power for use by the flashlight 2703. More or fewer electrical contacts may be used (including zero electrical contacts). In some embodiments, one or more electrical contacts may be used for control signals, such as to turn flashlight 2703 on or off, adjust a brightness of flashlight 2703, and/or the like.

Turning to FIGS. 28B-28D, these figures illustrate the lighting system 2801, and enlarged views of the mounting base 2705 of the lighting system 2801, detached from the mounting socket 2710 of the head-mounted display 2122. The mounting base 2705 in this embodiment comprises a first recess 2821 and a second recess 2823. The first recess 2821 is sized and positioned to engage the first rod 2820 of the mounting socket 2710 (see FIG. 28E), and the second recess 2823 is sized and positioned to engage the second rod 2822 of the mounting socket 2710 (see FIG. 28E). For example, in order to attach the mounting base 2705 to the mounting socket 2710, a user may position the first recess 2821 such that it is engaged with the first rod 2820, and the user may then rotate the lighting system 2801 downward (e.g., pivoting about the first rod 2820) until the second recess 2823 has engaged the second rod 2822. As can be seen in FIG. 28C, the first recess 2821 opens in a generally rearward direction, and second recess 2823 opens in a generally downward direction. By having the two recesses open in different directions, this can make it such that, when both recesses 2821, 2823 are engaged with the rods 2820, 2822, respectively, the engagement of second recess 2823 with second rod 2022 will resist recess 2821 from becoming disengaged with first rod 2820.

As can further be seen in FIGS. 28C and 28D, the mounting base 2705 further comprises a movable latch 2824 that can pivot about pivot axis 2828 in order to allow or disallow second rod 2822 from entering and/or exiting the second recess 2823. Accordingly, when the second recess 2823 is fully engaged with the second rod 2822, and the latch 2824 is in the closed position (e.g., the position shown in FIGS. 28C and 28D), the latch 2824 will resist second rod 2822 from becoming disengaged from second recess 2823, thus fully (or at least sufficiently) constraining the location of the lighting system 2801 with respect to the rest of the head-mounted display 2122.

With continued reference to FIG. 28D, the mounting base 2705 further comprises a user interface feature, such as a button 2826, that can be manipulated by a user in order to move the latch 2824 into the open position, thus allowing removal of the mounting base 2705 from the mounting socket 2710. Desirably, the latch 2824 is biased to the closed position by, for example, a spring, such as spring 2830 visible in FIG. 28D. As can also be seen in FIG. 28D, the latch 2824 desirably comprises an angled or tapered outer surface that will engage the second rod 2822 during installation and force the latch 2824 to pivot and allow the second rod 2822 to engage the second recess 2823 without necessarily requiring a user to manipulate the button 2826 during installation. Stated another way, the latch 2824 and button 2826 may be configured such that a user can attach the mounting base 2705 to the mounting socket 2710 without manipulating the button 2826, but may be configured to require the button 2826 to be manipulated in order to remove the mounting base 2705 from the mounting socket 2710.

FIG. 28D also illustrates an electrical contact 2832 extending downward from the bottom of the mounting base 2705. Desirably, the electrical contact 2832 may be spring-loaded and/or elastically bendable such that a sufficiently low resistance electrical connection may be made between the electrical contact 2832 and a corresponding one of the electrical contacts 2834 of the mounting socket 2710 (see FIG. 28E). Although the side view of FIG. 28D only shows one electrical contact 2832, the mounting base 2705 desirably comprises or consists essentially of two electrical contacts 2832, positioned corresponding to the positions of the two electrical contacts 2034 of the mounting socket 2710 shown in FIG. 28E. Only one is visible in FIG. 28D, however, because the second is directly behind the first in this side view orientation. Further, similar to as discussed above with respect to the electrical contacts 2834 of mounting socket 2710, the mounting base 2705 may include more or fewer electrical contacts 2832.

Figure 28F:
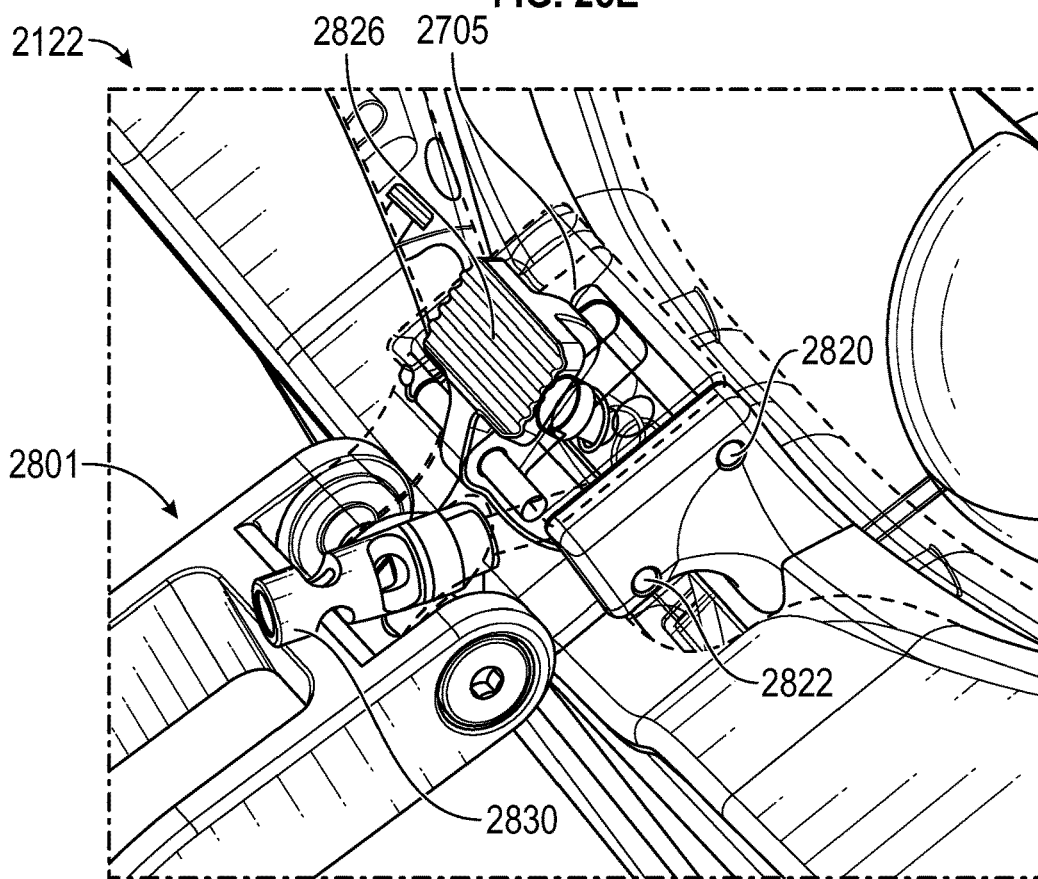

With reference to FIG. 28F, which shows the lighting system 2801 attached to the rest of the head-mounted display 2122, this figure also shows a strain relief member 2830 extending out a front of the mounting base 2705. Although not shown, the strain relief member 2830 may have one or more wires passing therethrough that, for example, transfer electrical power and/or control signals from the electrical contacts 2832 (received from electrical contacts 2834) to the flashlight 2703.

Example Optics Considerations and Clip-On Lens Assemblies

Various users of the head-mounted displays disclosed herein (e.g., surgeon 26) may require prescription lenses for vision correction. For example, at least some of such users may typically wear prescription eyeglasses to correct their vision. Some of the head-mounted displays disclosed herein may be able to fit over such prescription eyeglasses, but such a configuration may not be ideal. As an alternative to a surgeon needing to wear both prescription eyeglasses and a head-mounted display as disclosed herein, various embodiments of the head-mounted displays disclosed herein may be configured to have prescription lenses coupled thereto in order to allow the surgeon to use the head-mounted display with clear vision without needing to wear separate corrective devices, such as eyeglasses, contact lenses, and/or the like.

FIGS. 29A-29E illustrate one embodiment of a head-mounted display 2922 that includes clip-on, snap-on, removable, and/or replaceable prescription lenses, to enable the head-mounted display 2922 to be used by a variety of users (e.g., surgeons 26) with a variety of corrective lens requirements. The head-mounted display 2922 is similar to the head-mounted display 50 described above with reference to FIG. 3, and the same or similar reference numbers are used to refer to the same or similar components. The head-mounted display 2922 depicted in FIG. 29A includes two significant differences from the head-mounted display 50 depicted in FIG. 3. First, left and right temple arms 43, 44 (which may be included in head-mounted display 50, but are not shown in FIG. 3) are shown attached to the display assembly frame 41. The temple arms 43, 44 may be the same or similar to, for example, the left and right temple arms 43, 44 of the head-mounted display 22 of FIG. 2A. Second, the displays 49a, 49b have been modified to utilize posterior lenses 2912 that are part of a detachable lens assembly 2910 (e.g., clip-on lens assembly, snap-on lens assembly, and/or the like) (see FIG. 29B).

Figure 29B:
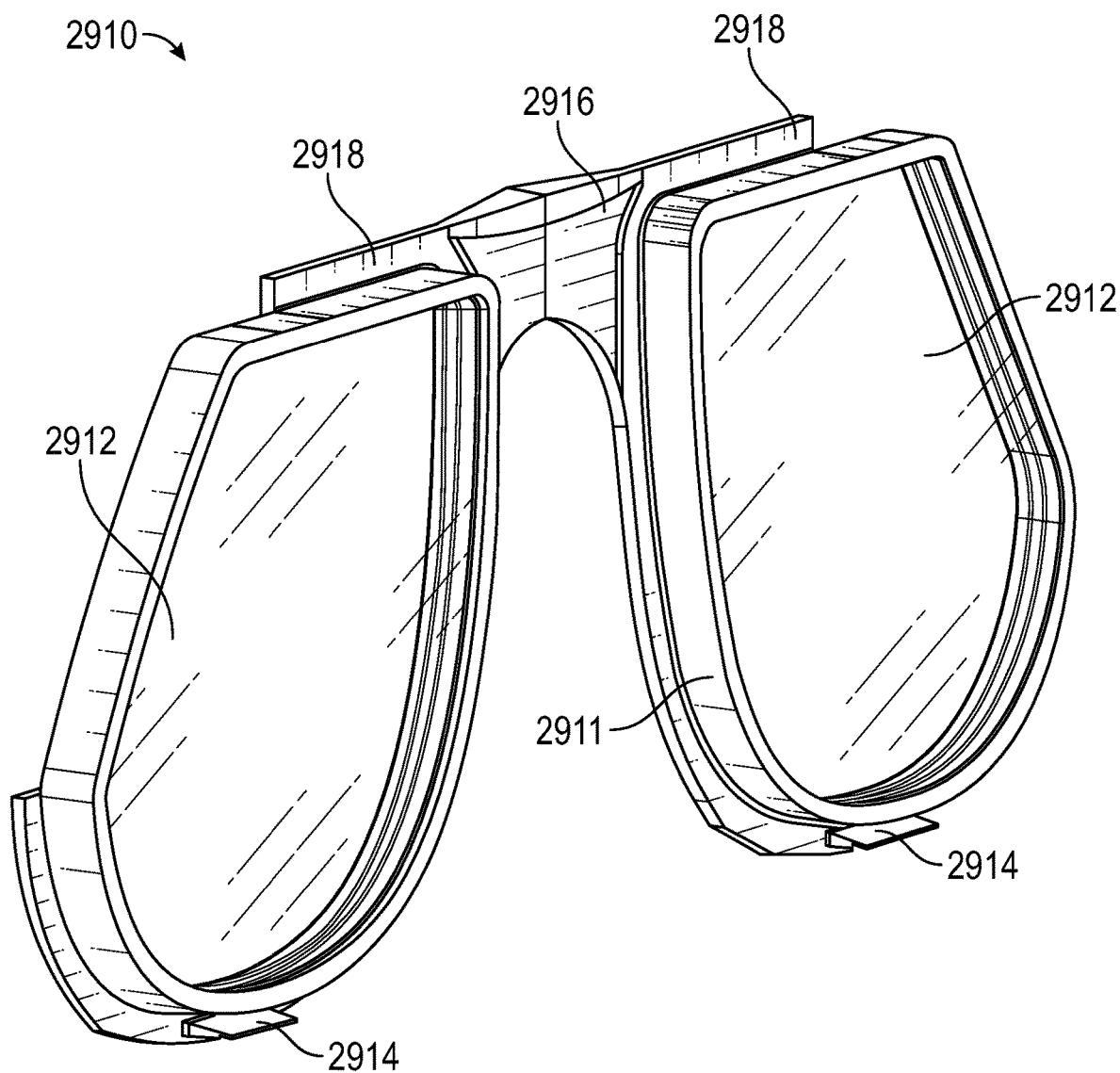
Figure 29C:
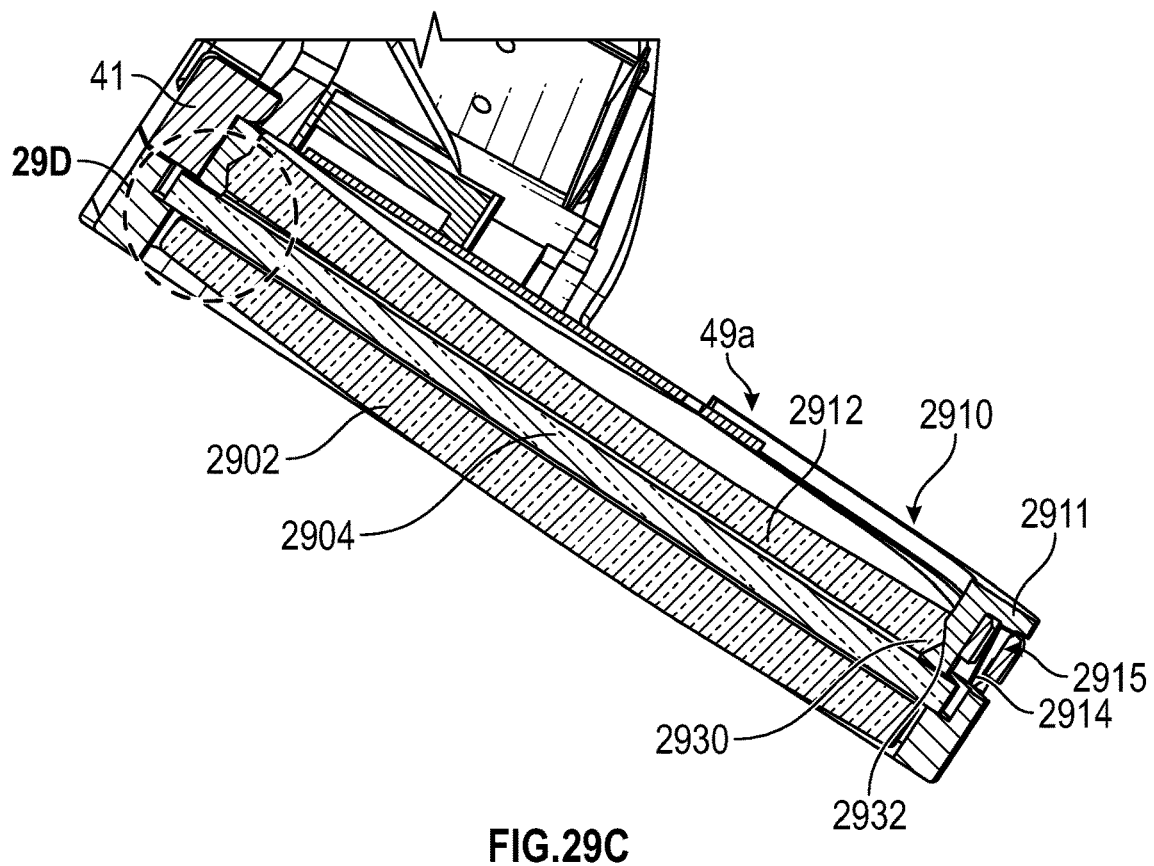

FIG. 29C depicts a cross-section of the right display 49a, with the left display 49b being similar in construction. The display 49a includes an anterior lens 2902 and a posterior lens 2912. Between the anterior lens 2902 and posterior lens 2912 is a reflective waveguide lens 2904, which can be used to display images transmitted from the waveguide 52 (see FIG. 3). For example, the waveguide lens 2904 may be a lens that is embedded with multiple partially reflective mirrors that enable a user to see images transmitted to the waveguide lens 24 by the waveguide 52, while also allowing the user to see through the waveguide lens 2904. In some embodiments, the reflective waveguide lens 2904 comprises a reflective waveguide lens available from Lumus Ltd. (Ness Ziona, Israel). It should be noted that, although the embodiment shown in FIG. 29C includes a detachable lens assembly, the various lenses shown in FIG. 29C may also be used in a similar configuration in embodiments that are not intended to have any of the lenses be detachable. For example, some embodiments may include anterior lens 2902, posterior lens 2912, and reflective waveguide lens 2904 positioned in substantially the same relative positions as shown in FIG. 29C, but all permanently or semi-permanently installed, instead of having the posterior lens 2912 be removable.

In some embodiments, the posterior lens 2912 is by default (e.g., before consideration for a personal prescription compensation) shaped to provide a particular diopter to achieve a focus for an AR image at a particular operational distance. For example, in some embodiments, the posterior lens 2912 is by default shaped to provide −2D diopter compensation to achieve a focus at a 0.5 m (e.g., 50 cm plus or minus 20 cm) operational distance. The anterior lens 2902 may be shaped to compensate for the above-described effect of the posterior lens 2912 (e.g., to reduce or eliminate the effect of the posterior lens 2912 on the view of realty through the display 49a). For example, with the default −2D posterior lens 2912, the anterior lens 2902 may, for example, be shaped to provide a +2D diopter compensation. The considerations for focal distance in the disclosed systems can be different than for normal eyeglasses or other augmented reality systems (such as consumer-focused augmented reality systems). For example, normal eyeglasses or other augmented reality systems (such as consumer-focused augmented reality systems) may be configured to achieve focus at a distance of approximately 3-4 m or greater. When using systems as disclosed herein with surgical or other medical procedures, however, the desired operational or focal distance may be significantly lower, such as approximately 50 cm, within a range of approximately 30 cm to 70 cm, and/or the like. For example, the wearer may be viewing a treatment or diagnostic site from a relatively close range from a standing or sitting position adjacent a patient. That said, the systems disclosed herein may also be used in other applications (e.g., athletics and fitness, gaming, driving, product design, navigation, manufacturing, logistics, shopping and commerce, educational training, remote collaboration, etc.), which each may have longer or shorter desired focal distances, and the diopter compensations in the anterior and posterior lenses may be adjusted accordingly to account for such different focal distances.

With continued reference to FIG. 29C, for a user (e.g., surgeon 26) that does not require vision correction, the default posterior lens 2912 may be acceptable. For a user that requires vision correction, however, it may be desirable to replace the posterior lens 2912 with an alternative lens that changes the compensation in order to correct for that specific user's vision. Accordingly, the posterior lens 2912 in the head-mounted display 2922 is part of a detachable, removable and/or replaceable clip-on lens assembly 2910 that is shown in FIG. 29B. With reference to FIG. 29B, the clip-on lens assembly 2910 comprises or consists essentially of a frame 2911 (e.g., posterior lens frame) that holds left and right posterior lenses 2912, and that includes a bridge portion 2916 that fixes the distance between the two posterior lenses 2912. It should be noted that alternative embodiments could use individual clip-on lenses that, for example, do not have a bridge 2916 coupling them together to form a single clip-on lens assembly.

The frame 2911 of the clip-on lens assembly 2910 further comprises or consists essentially of two protrusions 2918 protruding from a top of the frame 2911. The protrusions 2918 are shaped to fit into corresponding recesses 2919 of frame 41 of the head-mounted display 2922 (see FIG. 29A). Additionally, the frame 2911 includes two clips 2914 protruding from a bottom portion of the frame 2911, and shaped to form a snap fit into a slot 2915 in the frame 41 (see FIG. 29C). In order to install the clip-on lens assembly 2910 onto the frame 41, a user may, for example, insert the protrusions 2918 into the recesses 2919, and then pivot the clip-on lens assembly 2910 into the final position shown in FIGS. 29A and 29C, with the clips 2914 snapped into corresponding slots 2915. Removal may be conducted by doing the opposite process, namely pulling the clips 2914 from the slots 2015, pivoting the bottom of the frame 2911 away from the frame 41, and then removing the protrusions 2918 from the recesses 2919 in the frame 41.

Various other mechanical methods of removably attaching a posterior lens assembly to the frame 41 may also or alternatively be used. For example, more clips 2914 and/or protrusions 2918 may be used, the clips 2914 and/or protrusions 2918 may be replaced by and/or supplemented by magnets, components that form a friction fit, adhesives, screws, other fasteners, and/or the like.

Figure 29D:
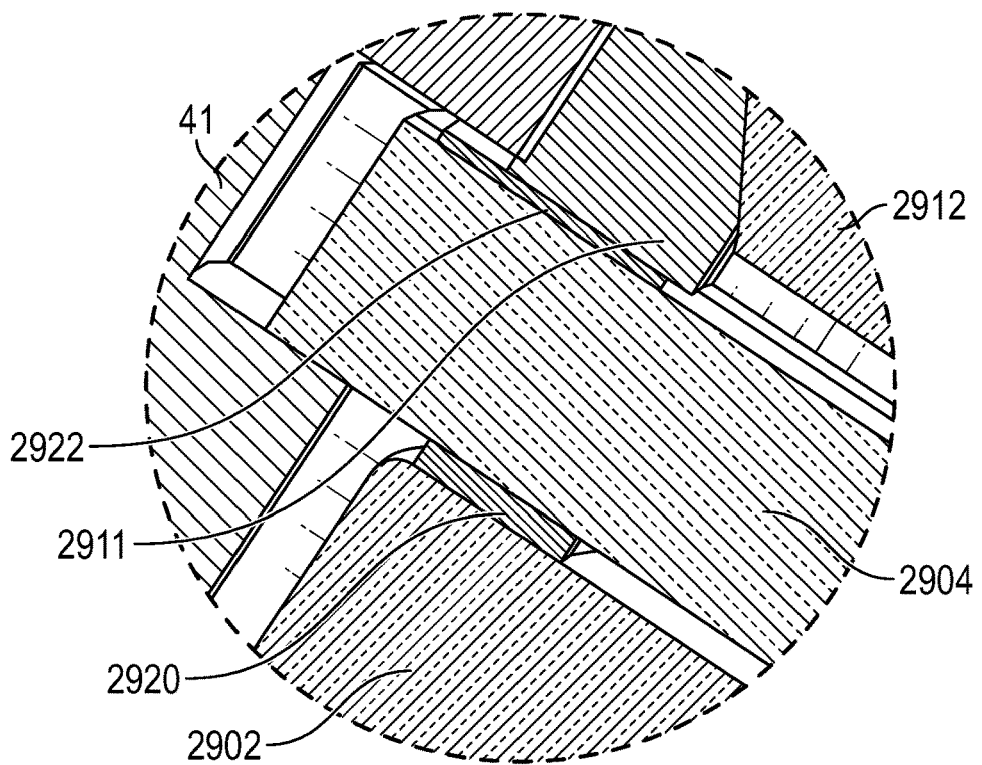
Figure 29E:
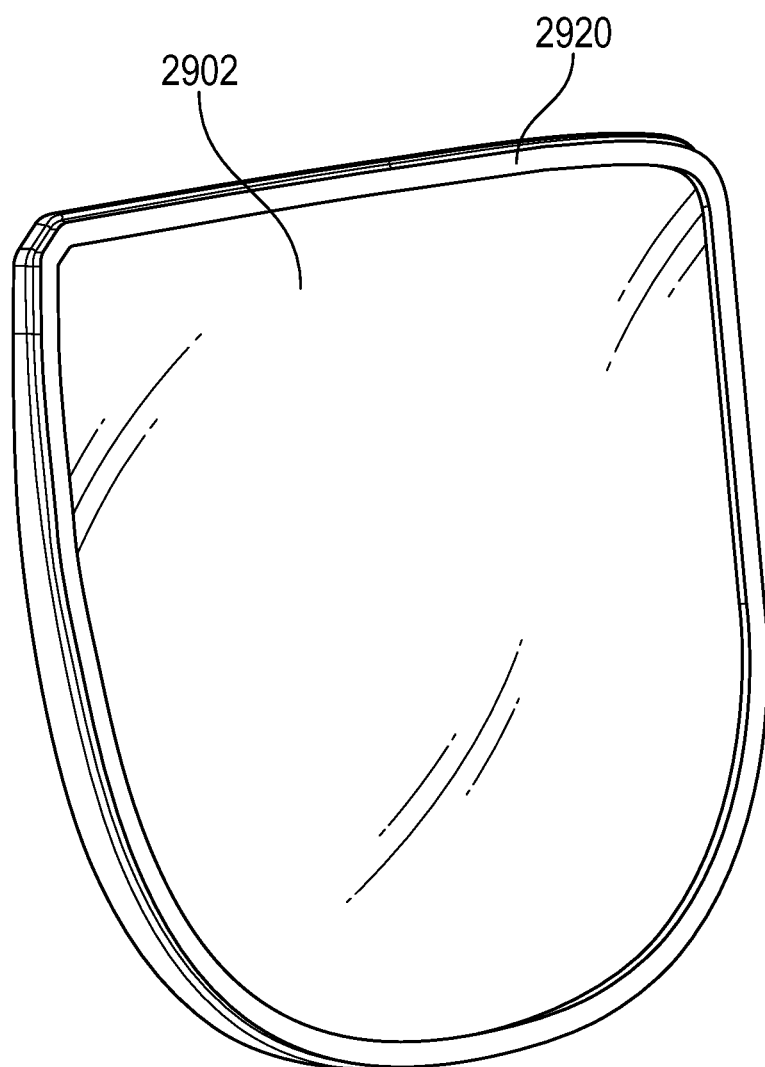

Turning now to FIG. 29D, this figure illustrates additional details of the cross-sectional view of FIG. 29C. Specifically, FIG. 29D illustrates how the lenses 2902 and 2912 can be sealed to the reflective waveguide lens 2904. For example, a first seal 2920 may be positioned about a perimeter of the anterior lens 2902 and seal anterior lens 2902 to a front side of the reflective waveguide lens 2904. FIG. 29E is a perspective view of one of the anterior lenses 2902 that shows an example of the seal 2920 positioned about the perimeter of the anterior lens 2902. In this embodiment, the seal 2920 may comprise double-sided tape, such as a double-sided foam tape that has adhesive on both sides and thus permanently or semi-permanently adheres the anterior lens 2902 to a front side of the reflective waveguide lens 2904.

With continued reference to FIG. 29D, a second seal 2922 is shown between the frame 2911 of the clip-on lens assembly 2910 and a rear side of the reflective waveguide lens 2904. In order to make the clip-on lens assembly 2910 more easily removable and/or replaceable, the seal 2922 may in some embodiments comprise a single-sided tape, such as a foam tape that has adhesive on one side, such as the side connected to the frame 2911. Accordingly, with such a configuration, the frame 2911 may be sealed against the reflective waveguide lens 2904, but may be easily removed and replaced without leaving adhesive residue on the reflective waveguide lens 2904. In some embodiments, one or both of seals 2920 and 2922 may also perform the function of acting as a spacer between the anterior and posterior lenses and the reflective waveguide lens, which can be beneficial in some cases.

In this embodiment, the posterior lens 2912 is desirably affixed to the frame 2911 of the clip-on lens assembly 2910. For example, as can be seen in FIG. 29C, the posterior lens 2912 may comprise a hump or protrusion 2930 that fits into a corresponding groove or depression 2932 in the frame 2911. The fit between the frame 2911 and posterior lens 2912 may desirably be an interference fit that fixedly retains and seals the posterior lens 2912 to the frame 2911. Additionally or alternatively, the perimeter of the posterior lens 2912 may be adhered to the frame 2911 with adhesive.

The design discussed above and shown in FIGS. 29A-29E has a number of beneficial features including, for example, relatively easy tool free installation of custom prescription posterior lenses, maintaining sealing between both the anterior and posterior lenses and the reflective waveguide lens, and the potential for relatively quick production of a customized head-mounted displays. The maintaining of sealing between the anterior and posterior lenses and the reflective waveguide lens can be particularly beneficial in, for example, maintaining ideal transparency of the reflective waveguide lens.

The frame 2911 of the clip-on lens assembly 2910 may be manufactured from a variety of materials. In some embodiments, it may be desirable to manufacture the frame 2911 from PEEK (polyetheretherketone), which may, for example, have a relatively desirable weight to strength ratio and may be suitable for use with a variety of cleaning procedures. In some embodiments, the weight of the frame 2911 may be approximately or no greater than 4 g. In some embodiments, other materials may be used for the frame 2911, such as polycarbonate, which may be a more efficient material to use in some cases.

Figure 30:
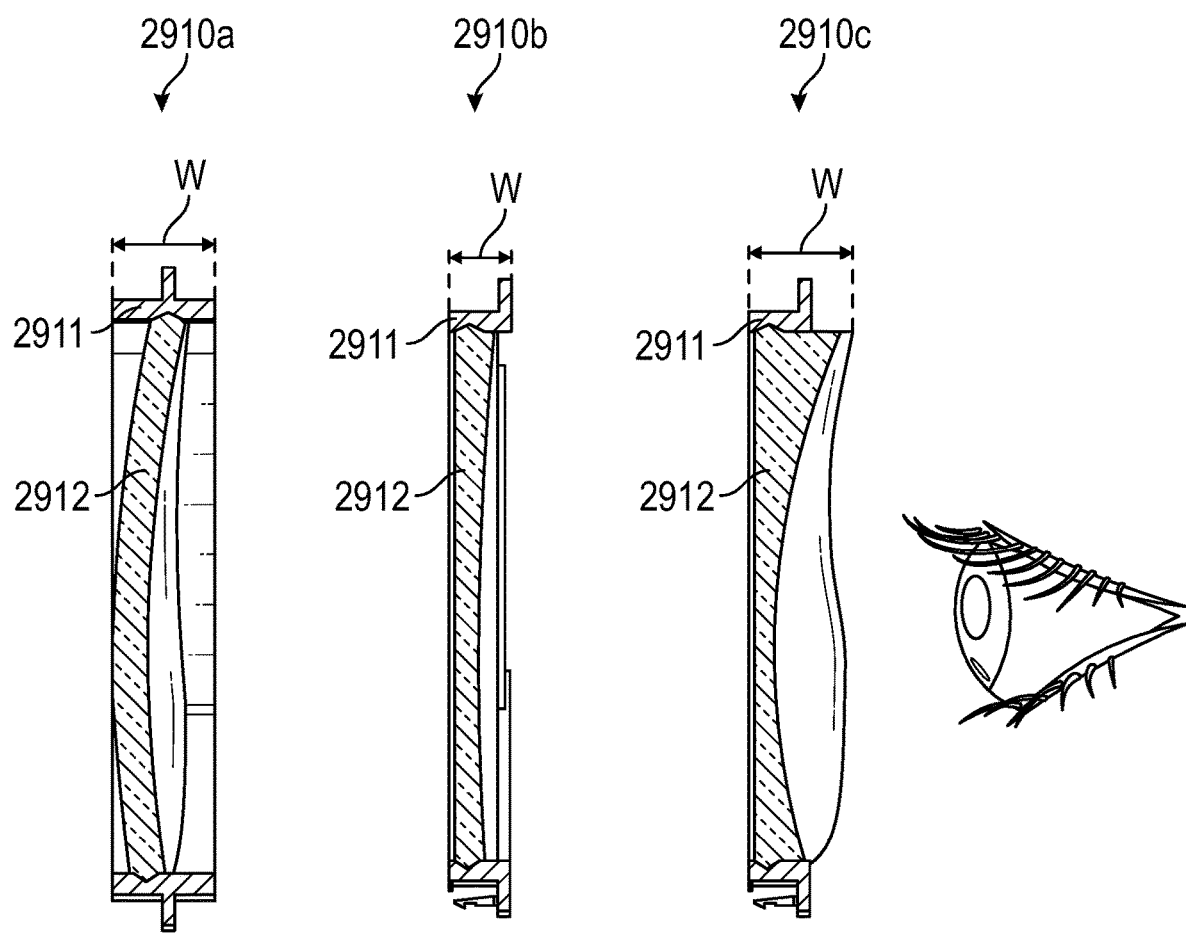
FIG. 30 is a schematic diagram illustrating different lenses and frames for use with the clip-on lens assembly of FIG. 29A.
Figure 31A:
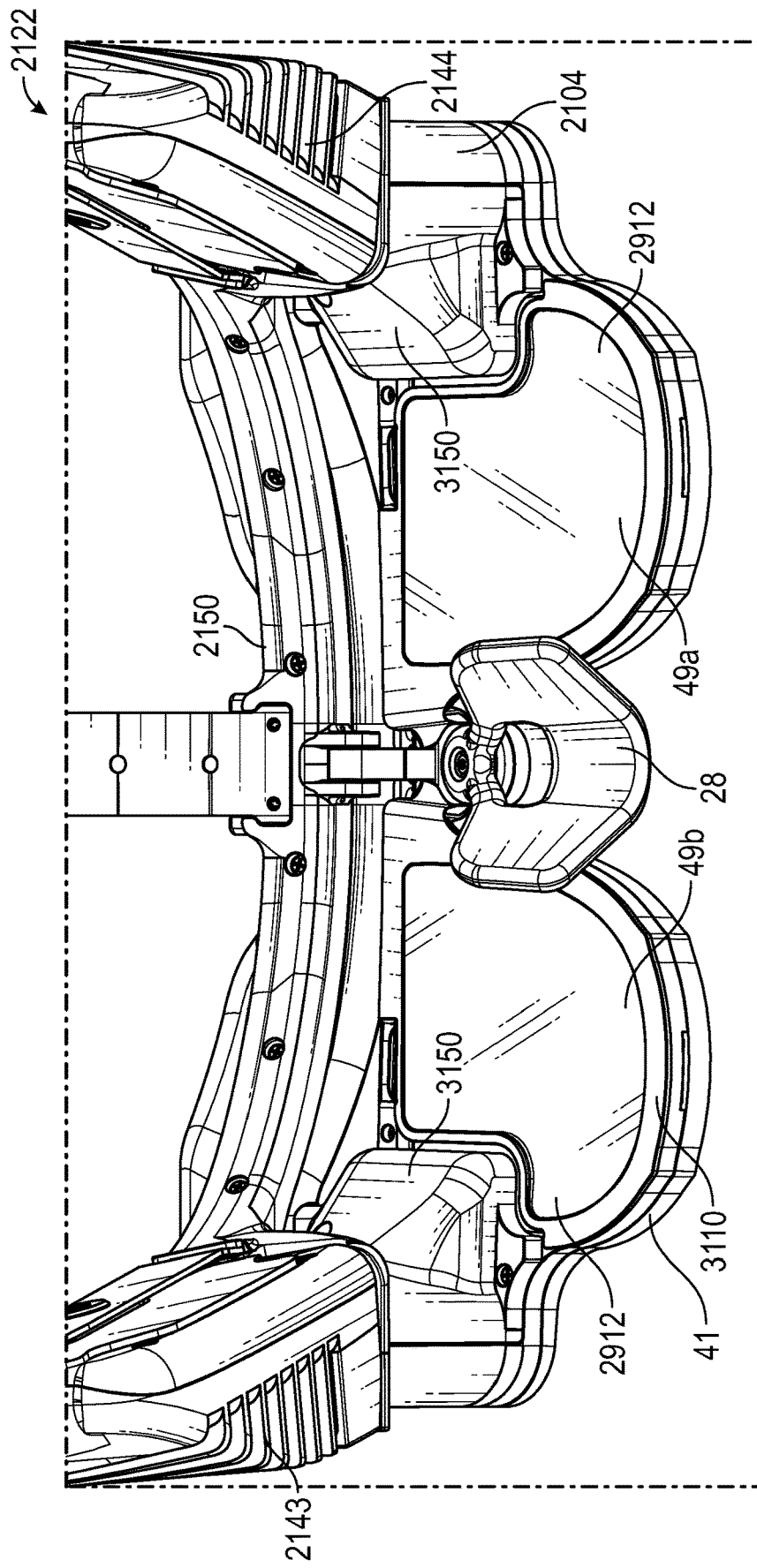
FIGS. 31A-31E illustrate another embodiment of a clip-on lens assembly that can be used with any of the head-mounted displays disclosed herein.
Figure 31B:
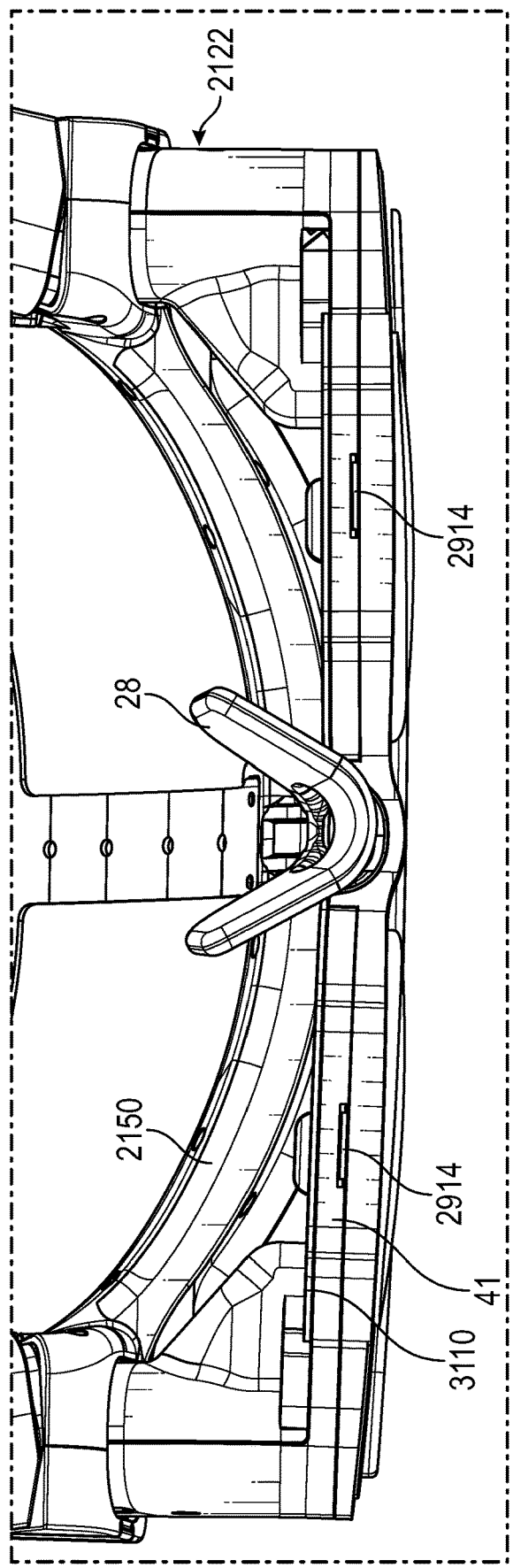
Figure 31C:
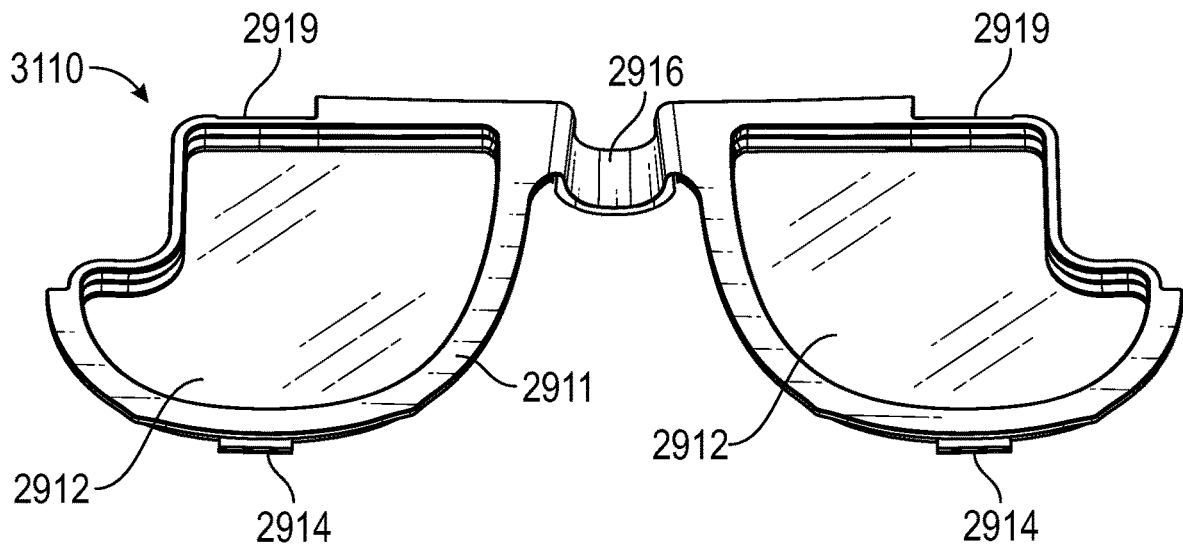
Figure 31D:
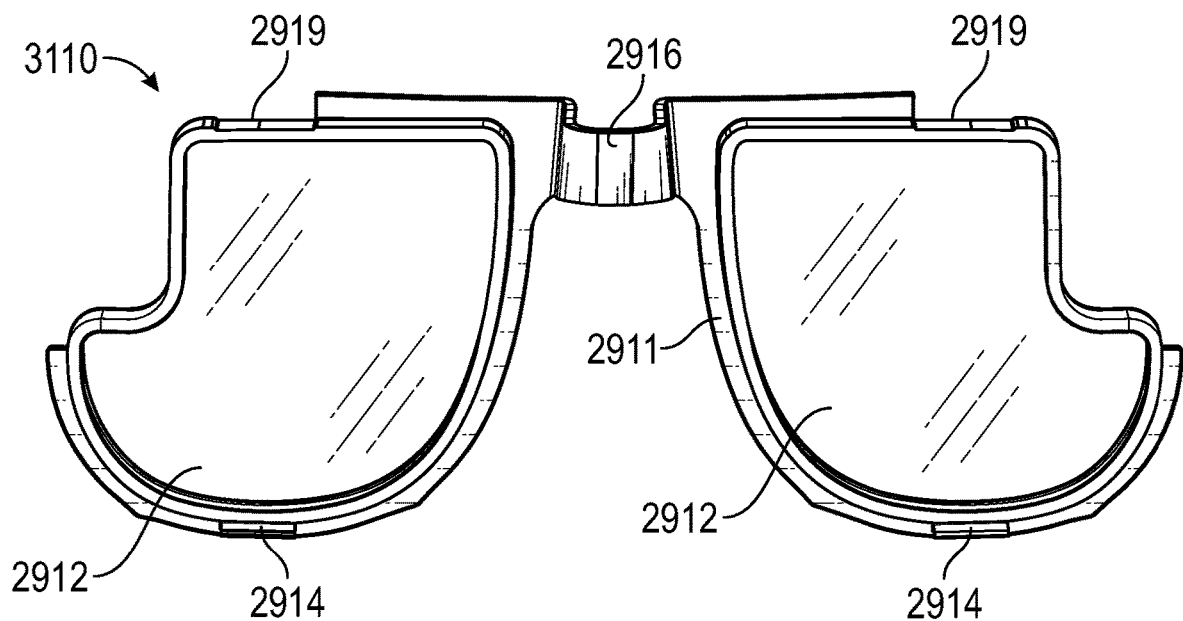
Figure 31E:
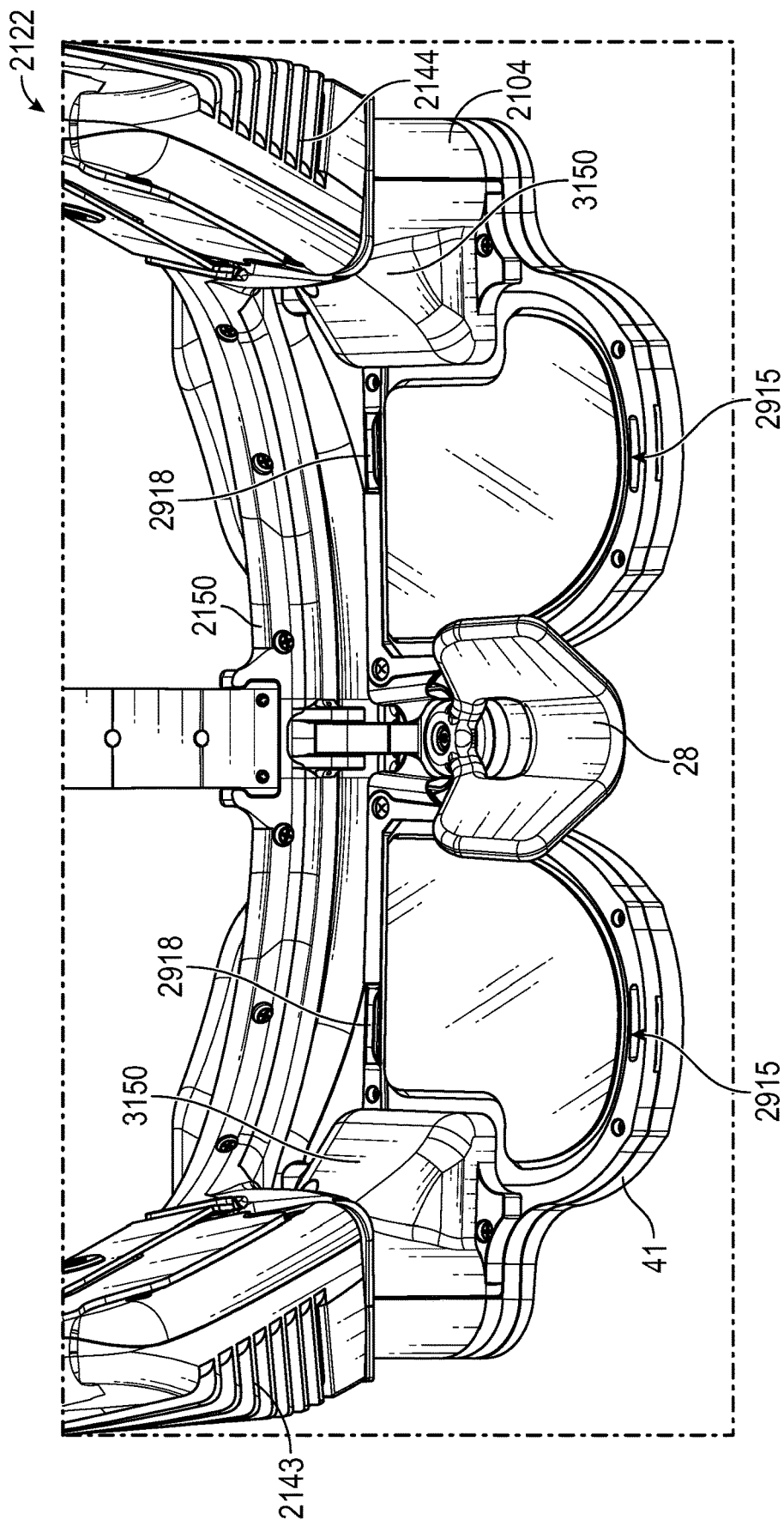

Turning to FIG. 30, this figure illustrates schematically how the cross-sectional profile of the frame 2911 of the clip-on lens assembly 2910 may vary with posterior lenses 2912 having different diopter compensations. Specifically, FIG. 30 illustrates cross-sectional views of three different variations of the clip-on lens assembly 2910, namely clip-on lens assemblies 2910*a*, 2910*b*, and 2910*c*. Each of these variations shows a width W that indicates the overall width of the clip-on lens assembly 2910*a*, 2910*b*, 2910*c*. Clip-on lens assembly 2910*b* illustrates a diopter compensation of zero, and is the narrowest width assembly, with the width W of this assembly being approximately 4.7 mm. Clip-on lens assembly 2910*a* illustrates an example with a posterior lens 2912 having a diopter compensation of +6D, resulting in an assembly width W of approximately 7.7 mm. Finally, clip-on lens assembly 2910*c* illustrates an example with a posterior lens 2912 having a diopter compensation of −6D, resulting in an assembly width of approximately 10.5 mm.

Turning to FIGS. 31A-31E, these figures illustrate additional views and/or portions of the head-mounted display 2122 of FIG. 21A, to show a detachable lens assembly 3110 (e.g., clip-on lens assembly, snap-on lens assembly, and/or the like). The clip-on lens assembly 3110 of head-mounted display 2122 is similar to the clip-on lens assembly 2910 of head-mounted display 2922 discussed above with reference to FIGS. 29A-29E, and the same or similar reference numbers are used to refer to the same or similar features.

One difference in the clip-on lens assembly 3110 of head-mounted display 2122 is that the outer profile shape of the posterior lenses 2912 and the frame 2911 (e.g., posterior lens frame) that the lenses fit within is shaped differently. Specifically, the outer profile comprises a stepped shape in order to provide clearance for portions 3150 of the housing 2104 of optical engine 55 which are shaped somewhat differently than the corresponding portions of head-mounted display 2922. Another difference is that the configurations of protrusions 2918 and recesses 2919 are different. Specifically, the protrusions 2918 are part of housing 2104, and the recesses 2919 are part of the frame 2911, which is the opposite of the configuration discussed above with reference to FIGS. 29A-29E. The clip-on lens assembly 3110 still includes similar clips 2914 as the clip-on lens assembly 2910. Further, the overall cross-sectional construction of the displays 49*a*, 49*b* of head-mounted display 2122 can be functionally similar to the structure discussed above with reference to FIGS. 29C and 29D.

Figure 32:
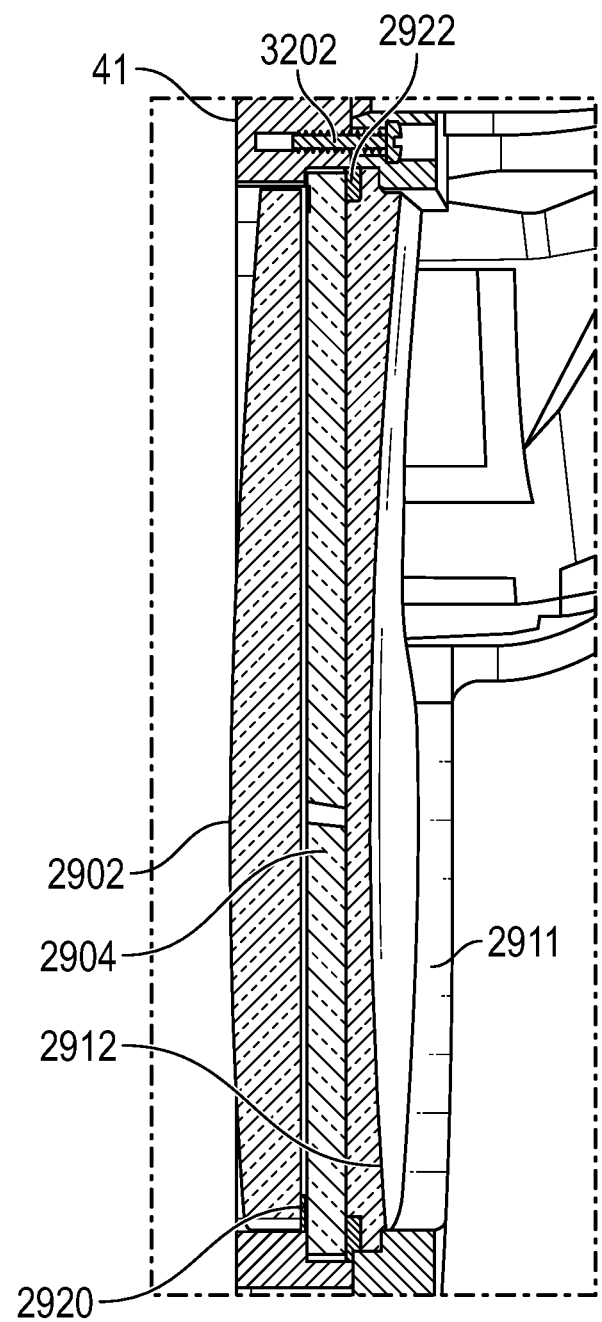
FIG. 32 illustrates an embodiment of an AR display having changeable lenses that can be used with any of the head-mounted displays disclosed herein.

Finally, turning to FIG. 32, this figure illustrates a cross-section similar to the cross-sections of FIGS. 29C and 29D, but depicts an alternative screw-on design instead of clip-on or snap-on design. Specifically, the structure shown in FIG. 32 includes a display assembly frame 41 that has a reflective waveguide lens 2904 coupled thereto, an anterior lens 2902 adhered to the front of the waveguide lens 2904 using seal 2920, and a posterior lens 2912 attached to the back of the waveguide lens 2904, with seal 2922 positioned between the posterior lens 2912 and waveguide lens 2004. Instead of frame 2911 being clipped or snapped on to frame 41, however, frame 2911 is screwed onto frame 41 with one or more screws 3202.

Another difference in the embodiment of FIG. 32 is that the front side of the posterior lens 2912 is shown as being flat or substantially flat. Such a design may help to, for example, save space in the display assembly. On the other hand, having a flat front surface for such an optical corrective lens may be nonstandard in the prescription lens industry, and thus may be more difficult and/or expensive to manufacture. Accordingly, in some embodiments, the front side of the posterior lens 2912 may also be curved, similar to the posterior lenses 2912 of FIG. 29C.

While certain examples of usage of the disclosed embodiments are given with respect to body portions containing spine vertebrae, the principles disclosed may also be used with respect to other bones and/or body portions than spine, including hip bones, pelvic bones, leg bones, arm bones, ankle bones, foot bones, shoulder bones, cranial bones, oral and maxillofacial bones, sacroiliac joints, etc.

The disclosed embodiments are presented with relation to image-guided surgery systems or methods, in general, and accordingly, the disclosed systems and devices should not be considered limited only to surgery or medical applications but for non-medical applications as well. For example, the disclosed embodiments are applicable to consumer or commercial applications such as athletics and fitness, gaming, driving, product design, navigation, manufacturing, logistics, shopping and commerce, educational training, remote collaboration, etc.

The terms "top," "bottom," "first," "second," "upper," "lower," "height," "width," "length," "end," "side," "horizontal," "vertical," and similar terms may be used herein; it should be understood that these terms have reference only to the structures shown in the figures and are utilized only to facilitate describing embodiments of the disclosure. Various embodiments of the disclosure have been presented in a range format. It should be understood that the description in range format is merely for convenience and brevity and should not be construed as an inflexible limitation on the scope of the disclosure. The ranges disclosed herein encompass any and all overlap, sub-ranges, and combinations thereof, as well as individual numerical values within that range. For example, description of a range such as from about 25 to about 45 degrees should be considered to have specifically disclosed subranges such as from 25 to 35 degrees, from 30 to 40 degrees, from 35 to 45 degrees etc., as well as individual numbers within that range (for example, 25, 30, 35, 40, 45, 32, 30.5 and any whole and partial increments therebetween). Language such as "up to," "at least," "greater than," "less than," "between," and the like includes the number recited. Numbers preceded by a term such as "about" or "approximately" include the recited numbers. For example, "approximately 260 g" includes "260 g." The terms "approximately", "about", and "substantially" as used herein represent an amount close to the stated amount that still performs a desired function or achieves a desired result.

Some embodiments comprise various features that are presented as single features (as opposed to multiple features). For example, in one embodiment, a system includes a single HMD, a single camera, a single processor, a single display, a single flashlight, a single PTA, a single PTA detent mechanism, a single head strap adjustment knob, etc. Multiple features or components are provided in alternate embodiments.

In some embodiments, the systems disclosed herein comprise one or more of the following: means for tilting (e.g., a hinge, a virtual hinge, an arc-shaped slot, detents, a strap configured to bend), means for adjusting (e.g., a knob, a rack and pinion), means for imaging (e.g., a camera or fluoroscope or MRI machine or CT machine), means for calibration (e.g., calibration jigs), means for registration (e.g., adapters, markers, objects, cameras), means for biasing (e.g., springs), means for fastening (e.g., anchors, adhesives, clamps, pins), means for segmentation (e.g., one or more neural networks), etc.

The processors described herein may include one or more central processing units (CPUs) or processors or microprocessors. The processors may be communicatively coupled to one or more memory units, such as random-access memory (RAM) for temporary storage of information, one or more read only memory (ROM) for permanent storage of information, and one or more mass storage devices, such as a hard drive, diskette, solid state drive, or optical media storage device. The processors (or memory units communicatively coupled thereto) may include modules comprising program instructions or algorithm steps configured for execution by the processors to perform any of all of the processes or algorithms discussed herein. The processors may be communicatively coupled to external devices (e.g., display devices, data storage devices, databases, servers, etc.) over a network via a network communications interface.

In general, the algorithms or processes described herein can be implemented by logic embodied in hardware or firmware, or by a collection of software instructions, possibly having entry and exit points, written in a programming language, such as, for example, Python, Java, Lua, C, C#, or C++. A software module or product may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the processing system 31, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules but may be represented in hardware or firmware. Generally, any modules or programs or flowcharts described herein may refer to logical modules that may be combined with other modules or divided into sub-modules despite their physical organization or storage.

The various features and processes described above may be used independently of one another or may be combined in various ways. All possible combinations and sub-combinations are intended to fall within the scope of this disclosure. In addition, certain method or process blocks or steps may be omitted in some implementations. The methods and processes described herein are also not limited to any particular sequence, and the blocks, steps, or states relating thereto can be performed in other sequences that are appropriate. For example, described blocks, steps, or states may be performed in an order other than that specifically disclosed, or multiple blocks or states may be combined in a single block or state. The example blocks, steps, or states may be performed in serial, in parallel, or in some other manner. Blocks, steps, or states may be added to or removed from the disclosed example embodiments. The example systems and components described herein may be configured differently than described. For example, elements may be added to, removed from, or rearranged compared to the disclosed example embodiments.

Any process descriptions, elements, or blocks in the flow diagrams described herein and/or depicted in the attached figures should be understood as potentially representing modules, segments, or portions of code which include one or more executable instructions for implementing specific logical functions or steps in the process.

It will be appreciated that the systems and methods of the disclosure each have several innovative aspects, no single one of which is solely responsible or required for the desirable attributes disclosed herein. The various features and processes described above may be used independently of one another or may be combined in various ways. The section headings used herein are merely provided to enhance readability and are not intended to limit the scope of the embodiments disclosed in a particular section to the features or elements disclosed in that section.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

What is claimed is:

1. A head-mounted display device comprising:
   a frame extending from a first end to a second end, the first end configured to be positioned adjacent a first temple of a wearer, and the second end configured to be positioned adjacent a second temple of the wearer;
   a head mounting assembly configured to retain the frame in a position on a head of the wearer, the head mounting assembly comprising at least one of a strap, a temple arm, or a forehead support; and
   a see-through display assembly coupled to the frame, wherein the see-through display assembly comprises:
      a display assembly frame;
      a waveguide lens coupled to the display assembly frame;
      an anterior lens affixed to the waveguide lens or to the display assembly frame in front of the waveguide lens;
      a posterior lens frame detachably coupled to the display assembly frame;
      a posterior lens affixed to the posterior lens frame;
      a first seal between the anterior lens and the waveguide lens; and
      a second seal between the posterior lens frame and the waveguide lens,
   wherein the posterior lens frame comprises a first protrusion at a top of the posterior lens frame that fits into a first corresponding recess of the display assembly frame,
   wherein the posterior lens frame comprises a second protrusion at a bottom of the posterior lens frame that forms a snap fit with a second corresponding recess of the display assembly frame, and
   wherein the see-through display assembly is pivotably coupled to the frame with a pantoscopic tilting assembly such that a pantoscopic tilt angle can be adjusted, the pantoscopic tilting assembly comprising:
      an arc-shaped slot that pivotably couples a portion of the see-through display assembly to a portion of the frame; and
      a detent mechanism comprising a plurality of detents configured to selectively retain the see-through display assembly in any of a plurality of predefined positions with respect to the frame.

2. The head-mounted display device of claim 1, wherein the head mounting assembly comprises the strap, the strap being a first side strap coupled to the first end of the frame, and
   wherein the head mounting assembly further comprises a second side strap coupled to the second end of the frame.

3. The head-mounted display device of claim 1, further comprising:
   a waveguide configured to supply visible light to the waveguide lens; and
   a backlight source configured to supply the visible light to the waveguide.

4. The head-mounted display device of claim 3, wherein the waveguide and the backlight source are positioned within the frame.

5. The head-mounted display device of claim 1, wherein the posterior lens is shaped to achieve a focal distance for an AR image displayed by the waveguide lens within a range of 30 cm to 70 cm.

6. The head-mounted display device of claim 1, wherein the posterior lens is shaped to provide a negative diopter compensation, and the anterior lens is shaped to provide a positive diopter compensation.

7. The head-mounted display device of claim 1, wherein the detent mechanism further comprises a spring-loaded pin or ball.

8. The head-mounted display device of claim 7, wherein the detent mechanism further comprises a guide member slidably engaged with the arc-shaped slot, the guide member configured to apply a force to the spring-loaded pin or ball to move the spring-loaded pin or ball from one of the plurality of detents to another of the plurality of detents.

9. The head-mounted display device of claim 1, wherein the frame further comprises a nose pad configured to engage a nose of the wearer.

10. A head-mounted display device comprising:
    a frame extending from a first end to a second end, the first end configured to be positioned adjacent a first temple of a wearer, and the second end configured to be positioned adjacent a second temple of the wearer;
    a head mounting assembly configured to retain the frame in a position on a head of the wearer, the head mounting assembly comprising at least one of a strap, a temple arm, or a forehead support; and a see-through display assembly coupled to the frame, wherein the see-through display assembly comprises:

a display assembly frame;

a waveguide lens coupled to the display assembly frame;

an anterior lens affixed to the waveguide lens or to the display assembly frame in front of the waveguide lens;

a posterior lens frame detachably coupled to the display assembly frame using at least one of: a snap fit, a friction fit, or a clip;

a posterior lens affixed to the posterior lens frame;

a first seal between the anterior lens and the waveguide lens; and a second seal between the posterior lens frame and the waveguide lens, wherein the see-through display assembly is pivotably coupled to the frame with a pantoscopic tilting assembly such that a pantoscopic tilt angle can be adjusted, the pantoscopic tilting assembly comprising:

an arc-shaped slot that pivotably couples a portion of the see-through display assembly to a portion of the frame; and a detent mechanism comprising a plurality of detents configured to selectively retain the see-through display assembly in any of a plurality of predefined positions with respect to the frame.

11. The head-mounted display device of claim 10, wherein the head mounting assembly comprises the strap, the strap being a first side strap coupled to the first end of the frame, and wherein the head mounting assembly further comprises a second side strap coupled to the second end of the frame.

12. The head-mounted display device of claim 10, further comprising:

a waveguide configured to supply visible light to the waveguide lens; and a backlight source configured to supply the visible light to the waveguide.

13. The head-mounted display device of claim 12, wherein the waveguide and the backlight source are positioned within the frame.

14. The head-mounted display device of claim 10, wherein the posterior lens is shaped to achieve a focal distance for an AR image displayed by the waveguide lens within a range of 30 cm to 70 cm.

15. The head-mounted display device of claim 10, wherein the posterior lens is shaped to provide a negative diopter compensation, and the anterior lens is shaped to provide a positive diopter compensation.

16. The head-mounted display device of claim 10, wherein the posterior lens frame comprises a first protrusion that fits into a first corresponding recess of the display assembly frame.

17. The head-mounted display device of claim 16, wherein the first protrusion is at a top of the posterior lens frame, and wherein the posterior lens frame comprises a second protrusion at a bottom of the posterior lens frame that fits into a second corresponding recess of the display assembly frame.

18. The head-mounted display device of claim 17, wherein the second protrusion forms a snap fit with the second corresponding recess of the display assembly frame.

19. The head-mounted display device of claim 10, wherein the detent mechanism further comprises a spring-loaded pin or ball.

20. The head-mounted display device of claim 19, wherein the detent mechanism further comprises a guide member slidably engaged with the arc-shaped slot, the guide member configured to apply a force to the spring-loaded pin or ball to move the spring-loaded pin or ball from one of the plurality of detents to another of the plurality of detents.

* * * * *